United States Patent
Cunningham et al.

Patent Number: 5,807,905
Date of Patent: Sep. 15, 1998

[54] BORATE PHOTOINITIATORS FROM POLYBORANES

[75] Inventors: Allan Francis Cunningham, Marly, Switzerland; Martin Kunz, Efringen-Kirchen, Germany; Hisatoshi Kura, Obayashi, Japan

[73] Assignee: Ciba Specialty Chemicals Corporation, Tarrytown, N.Y.

[21] Appl. No.: 754,708

[22] Filed: Nov. 21, 1996

[30] Foreign Application Priority Data

Nov. 24, 1995 [CH] Switzerland ............ 03341/95

[51] Int. Cl.⁶ ............ C08F 2/48; C08F 2/50; C08F 4/52; C07F 5/02
[52] U.S. Cl. ............ 522/25; 522/6; 522/12; 522/30; 522/26; 522/49; 522/50; 522/53; 522/57; 522/58; 522/59; 522/63; 522/64; 522/65; 522/66; 522/67; 522/68; 522/70; 522/96; 522/121; 568/3; 568/4; 568/5; 528/4; 528/5; 528/6; 528/7
[58] Field of Search ............ 568/3, 4, 5; 522/6, 522/12, 30, 49, 50, 53, 57, 58, 59, 63, 64, 65, 66, 67, 68, 70, 25, 26

[56] References Cited

U.S. PATENT DOCUMENTS

| | | | |
|---|---|---|---|
| 3,311,662 | 3/1967 | Washburn et al. | 260/606.5 |
| 4,772,530 | 9/1988 | Gottschalk et al. | 430/138 |
| 4,772,541 | 9/1988 | Gottschalk et al. | 430/339 |
| 4,833,263 | 5/1989 | Akasaki et al. | 558/384 |
| 4,954,414 | 9/1990 | Adair et al. | 430/138 |
| 5,053,546 | 10/1991 | Kaufman | 568/4 |
| 5,055,372 | 10/1991 | Shamklin et al. | 430/138 |
| 5,151,520 | 9/1992 | Gottschalk et al. | 548/110 |

FOREIGN PATENT DOCUMENTS

| | | |
|---|---|---|
| 0223587 | 5/1987 | European Pat. Off. |
| 0368629 | 5/1990 | European Pat. Off. |

OTHER PUBLICATIONS

Zeitschrift für Chemie, H. Holsapfel et al, seite 34–35 (1966).

Okada et al, "Synthesis and Properties of 1,3,5–Tris(dimesitylboryl)benzene and 1,3–Bis(dimesitylboryl)benzene)", J. Chem. Soc., Chem. Commun. pp. 74–75, Apr. 1992.

Baxter et al, "Dimesitylboryl Compounds. Part 10. Dynamic N.m.r. Studies of Selenium Derivatives", J. Chem. Research (S). pp. 94–95, Dec. 1983.

Elschenbroich et al "Arylborane als Sandwichliganden: . . .", Chem. ber. 129, pp. 871–878, Dec. 1996.

*Primary Examiner*—Susan W. Berman
*Attorney, Agent, or Firm*—David R. Crichton; Luther A. R. Hall

[57] ABSTRACT

Compounds of the formula I

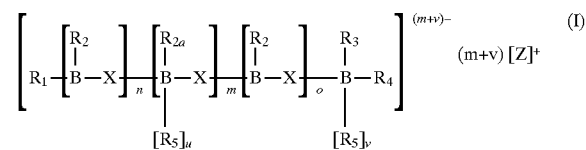

in which n and o are a number from 0 to 50, m is a number from 1 to 50, u and v are 0 or 1, and at least one of the indices u and v is 1, $R_1$, $R_2$, $R_{2a}$, $R_3$ and $R_4$ independently of one another are, for example, aromatic hydrocarbons, $R_5$, if n and o are 0, is for example $C_1$–$C_{12}$alkyl and, if n and/or o are greater than 0, or if n and o are 0 and at the same time only one index u or v is 1, $R_5$ may additionally, for example, be an aromatic hydrocarbon, at least one of the radicals $R_1$, $R_2$, $R_{2a}$, $R_3$, $R_4$ and $R_5$ being an aromatic hydrocarbon radical which is sterically hindered ortho to the boron atom, X is, for example, $C_1$–$C_{20}$alkylene, phenylene, biphenylene, etc., and Z is a radical which is able to form positive ions, are suitable as photoinitiators, both the compounds per se and their combination with dyes or other electron acceptors. Furthermore, the polyborane precursors of these borates possess, together with borate salts, photoinitiating properties.

27 Claims, No Drawings

BORATE PHOTOINITIATORS FROM POLYBORANES

The invention relates to mono- and polyborate compounds derived from polyboranes, to their use as photoinitiators, alone and in combination with coinitiators or electron acceptors respectively, to the use of polyboranes in combination with coinitiators or electron donors as photoinitiators, and to photopolymerizable compositions comprising the novel photoinitiators.

Monoborate compounds in association with ionic dyes have been described in the prior art as photoinitiators. For example, U.S. Pat. Nos. 4,772,530, 4,772,541 and 5,151,520 disclose monocyclic triaryl alkyl borate anions with catonic dyes, for example cyanines, rhodamines, etc., as counterions. These compounds are employed as photoinitiators. In U.S. Pat. No. 4,954,414, cationic transition metal complexes are used together with triaryl alkyl borate anions in photopolymerizable compositions. From U.S. Pat. No. 5,055,372 it is also known to use quaternary ammonium compounds, for example tetramethylammonium, pyridinium, cetylpyridinium, etc., as cationic counterions to the triaryl alkyl borate. In this publication, the borates are employed in association with aromatic ketone initiator compounds in photocurable materials. In Z. Chem. 6 (1966), 34, H. Holzapfel, P. Nenning and O. Wildner describe the preparation of the sodium phenyl borate of 1,4-bis(diphenylboryl)benzene. In Z. Chem. 6 (1966), 435, H. Holzapfel, P. Nenning and H. Stirn disclose the preparation of the corresponding bisphenyl borates and the corresponding naphthyl-substituted compounds. U.S. Pat. No. 3,311,662 describes polyborates which are employed as fungicides and bactericides. None of these documents discloses polyborate compounds as photoinitiators.

For the extensive range of applications of photoinitiators, there is a need in industry for reactive compounds. In the photocuring techniques which employ borate compounds and have been disclosed to date, in the prior art, the addition of dyes or coinitiators is an absolute necessity. However, there is particular interest in compounds which are suitable alone as such initiators, with the result that the addition of coinitiators is not absolutely necessary.

It has now surprisingly been found that compounds of the formula I

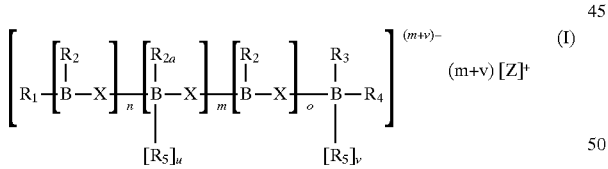

in which n and o are each a number from 0 to 50;

m is a number from 1 to 50;

u and v are 0 or 1, and at least one of the indices u and v is 1;

$R_1$, $R_2$, $R_{2a}$, $R_3$ and $R_4$ independently of one another are phenyl or another aromatic hydrocarbon, which radicals are unsubstituted or are substituted by unsubstituted or halo-, $OR_6$— and/or $NR_8R_9$-substituted $C_1$–$C_6$alkyl, $OR_6$, $S(O)_pR_7$, $OS(O)_2R_7$, $NR_8R_9$, $C(O)OR_6$, $C(O)NR_8R_9$, $C(O)R_{10}$, $SiR_{11}R_{12}R_{13}$, $BR_{14}R_{15}$, $P(O)_qR_{16}R_{17}$ or halogen;

p is 0, 1 or 2;

q is 0 or 1;

$R_5$, is $C_1$–$C_{12}$alkyl, $C_3$–$C_{12}$cycloalkyl, $C_2$–$C_8$alkenyl, phenyl-$C_1$–$C_6$alkyl or naphthyl-$C_1$–$C_3$alkyl, the radicals $C_1$–$C_{12}$alkyl, $C_3$–$C_{12}$cycloalkyl, $C_2$–$C_8$alkenyl, phenyl-$C_1$–$C_6$alkyl or naphthyl being unsubstituted or substituted by $OR_6$, $S(O)_pR_7$, $OS(O)_2R_7$, $NR_8R_9$, $C(O)OR_6$, $C(O)NR_8R_9$, $C(O)OR_{10}$,

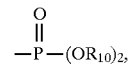

$SiR_{11}R_{12}R_{13}$, $BR_{14}R_{15}$ or halogen, or $R_5$ is phenyl or another aromatic hydrocarbon radical, which radicals are unsubstituted or substituted by $C_1$–$C_6$alkyl, $OR_6$, $S(O)_pR_7$, $OS(O)_2R_7$, $NR_8R_9$, $C(O)OR_6$, $C(O)NR_8R_9$, $C(O)R_{10}$, $SiR_{11}R_{12}R_{13}$, $BR_{14}R_{15}$ or halogen, at least one of the radicals $R_1$, $R_2$, $R_{2a}$, $R_3$, $R_4$ and $R_5$ being a phenyl radical which is substituted ortho to the bond to the boron atom, or being another aromatic hydrocarbon radical which is sterically hindered ortho to the boron atom;

$R_6$ and $R_7$ are unsubstituted or $COOR_{7a}$, OH, $C_1$–$C_{12}$alkoxy- or halo-substituted $C_1$–$C_{12}$alkyl, unsubstituted or mono- to penta-$C_1$–$C_6$alkyl-, -$C_1$–$C_{12}$alkoxy- or -halo-substituted phenyl, or unsubstituted or mono- to penta-$C_1$–$C_6$alkyl-, -$C_1$–$C_{12}$alkoxy- or -halo-substituted phenyl-$C_1$–$C_6$alkyl;

$R_{7a}$ is $C_1$–$C_{12}$alkyl $R_8$, $R_9$, $R_{10}$, $R_{11}$, $R_{12}$, $R_{13}$, $R_{14}$ and $R_{15}$ independently of one another are as defined for $R_6$ or are $C_3$–$C_{12}$cycloalkyl, or $R_8$ and $R_9$, together with the N atom to which they are attached, form a 5- or 6-membered ring which may additionally contain O or S atoms, or $R_{14}$ and $R_{15}$, together with the B atom to which they are attached, form a 5- or 6-membered ring;

X is $C_1$–$C_{20}$alkylene which is unsubstituted or substituted by $OR_6$, $S(O)_pR_7$, $OS(O)_2R_7$, $NR_8R_9$, $C(O)OR_6$, $C(O)NR_8R_9$, $C(O)R_{10}$, $SiR_{11}R_{12}R_{13}$, $BR_{14}R_{15}$, halogen or $P(O)_qR_{16}R_{17}$, or X is $C_3$–$C_{12}$cycloalkylene or $C_2$–$C_8$alkenylene, each of which is unsubstituted or substituted by $OR_6$, $S(O)_pR_7$, $OS(O)_2R_7$, $NR_8R_9$, $C(O)OR_6$, $C(O)NR_8R_9$, $C(O)R_{10}$, $Sir_{11}R_{12}R_{13}$, $BR_{14}R_{15}$ or halogen, or where these radicals are interrupted by one or more groups —O—, —S(O)$_p$— or —NR$_{18}$—, or X is a divalent aromatic hydrocarbon radical which is unsubstituted or substituted by $C_1$–$C_6$alkyl, $OR_6$, $S(O)_pR_7$, $OS(O)_2R_7$, $NR_8R_9$, $C(O)OR_6$, $C(O)NR_8R_9$, $C(O)R_{10}$, $SiR_{11}R_{12}R_{13}$, $BR_{14}R_{15}$ or halogen, or X is $C_1$–$C_{20}$alkylene which is interrupted by one or more groups —O—, —S(O)$_p$— or —NR$_{18}$—, or X is a radical of the formula II or III

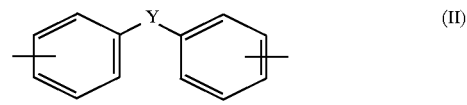

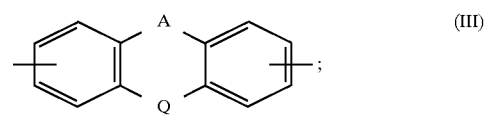

$R_{16}$ and $R_{17}$ independently of one another are as defined for $R_6$ or are $C_3$–$C_{12}$cycloalkyl, $R_{18}$ is as defined for $R_6$ or is hydrogen;

Y is —(CH$_2$)$_r$—, —C(O)—, —NR$_{18}$—, —O—, —S(O)$_p$—, —CR$_{19}$R$_{20}$—,

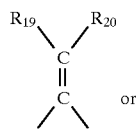

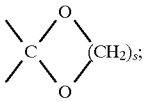

r is 1, 2 or 3;
s is 2 or 3;
$R_{19}$ and $R_{20}$ are $C_1$–$C_6$alkyl or phenyl, or $R_{19}$ and $R_{20}$, together with the C atom to which they are attached, form a 5- or 6-membered ring;
A and Q independently of one another are a direct bond, —$(CH_2)_r$—, —CH=CH—, —C(O)—, —$NR_{18}$—, —$S(O)_p$—, —$CR_{19}R_{20}$—,

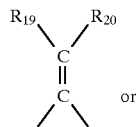

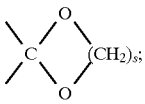

or the radicals $R_1$, $R_2$, $R_3$, $R_4$ and X form bridges to produce radicals of the formula (IV) or (V)

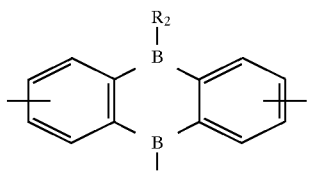

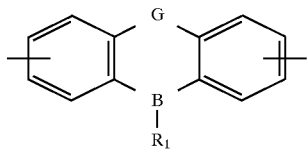

G is —$(CH_2)_t$—, —CHCH—, —C(O)—, —$NR_{18}$—, —O—, —$S(O)_p$—, —$CR_{19}R_{20}$—,

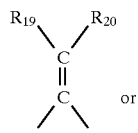

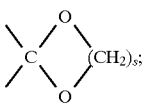

t is 0, 1 or 2;
the radicals of the formulae (II), (III), (IV) and (V) being unsubstituted or being substituted on the aromatic rings by $OR_6$, $S(O)_pR_7$, $OS(O)_2R_7$, $NR_8R_9$, $C(O)OR_6$, $C(O)NR_8R_9$, $C(O)R_{10}$, $SiR_{11}R_{12}R_{13}$, $BR_{14}R_{15}$ or halogen and where additional phenyl rings may be fused to the phenyl rings of the formulae (II), (III), (IV) and (V); provided that $R_1$, $R_{2a}$, $R_3$ and $R_4$ are not simultaneously α-naphthyl, if X is phenylene or 4,4'-biphenylene; and Z is a radical which is able to form positive ions, especially alkali metals, ammonium or tetraalkylammonium, sulfonium- or phosphomium radicals, are suitable as photoinitiators for the photopolymerization of compounds containing ethylenically unsaturated double bonds. The compounds of the formula I are per se surprisingly effective as photoinitiators even without additional coinitiators.

In the borate compounds of the formula I, at least one of the radicals $R_1$–$R_5$ is a phenyl ring which is substituted ortho to the bond to the boron atom or is another aromatic hydrocarbon radical which is sterically hindered ortho to the boron atom. Ortho-substitution here is generally understood to mean a bond in the o position of the aryl ring with respect to the boron central atom, thus including, for example, a fused-on ring. In accordance with this definition, therefore, some polycyclic aromatic hydrocarbons, for example naphthyl, are also rings (ring systems) which are substituted ortho to the bond to the boron central atom.

Aromatic hydrocarbons as may be present in the novel compounds may, for example, contain one or more, especially 1 or 2, heteroatoms. Examples of suitable heteroatoms are N, P, O and S, preferably N or O. Examples of aromatic hydrocarbon radicals are phenyl, α- and β-naphthyl, stilbenyl, biphenyl, o-, m-, p-terphenyl, triphenylphenyl, binaphthyl, anthracyl, phenanthryl, pyrenyl, furan-2-yl or furan-3-yl, thiophen-2-yl or thiophen-3-yl, pyridin-2-yl or pyridin-3-yl, quinolyl or isoquinolyl.

Also suitable are aromatic hydrocarbon radicals of the formula

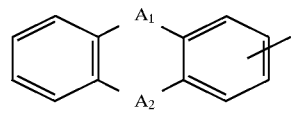

in which $A_1$ and $A_2$ independently of one another are a direct bond, —$(CH_2)_r$—, —CH=CH—, —C(O)—, $NR_{18}$, $S(O)_p$, —$CR_{19}R_{20}$,

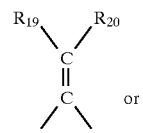

where r, s, p, $R_{19}$ and $R_{20}$ are as defined above. Examples of these are anthracyl, fluorenyl, thianthryl, xanthyl, acridinyl, phenazinyl, phenothiazinyl, phenoxathiinyl and phenoxazinyl.

Stilbenyl is 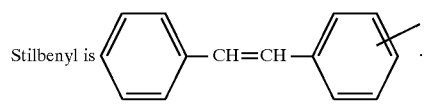
Biphenyl is 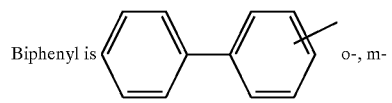 o-, m-
or p-terphenyl are 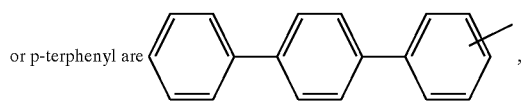,
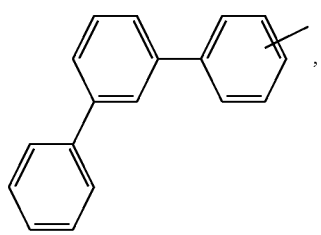,
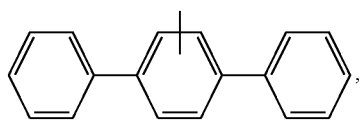,
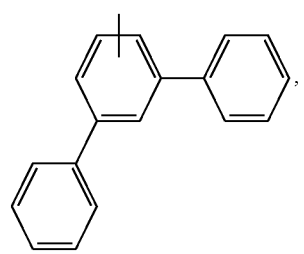,
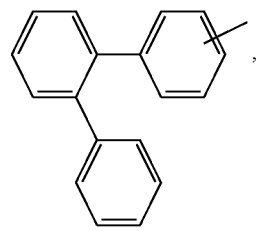,
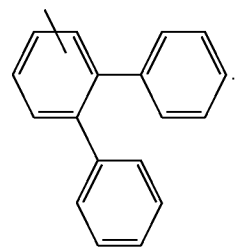
Triphenylphenyl is  or
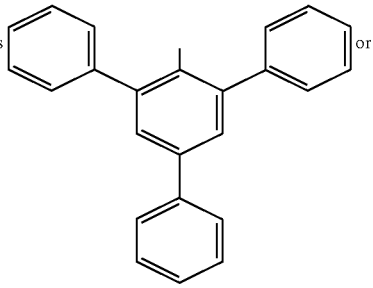.
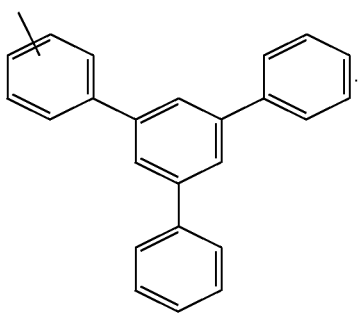
Binaphthyl is 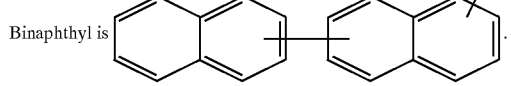.
Anthracyl is 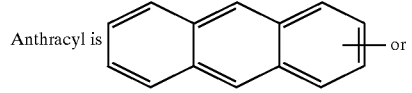 or
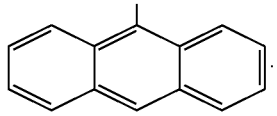.
Phenanthryl is 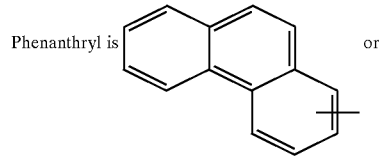 or
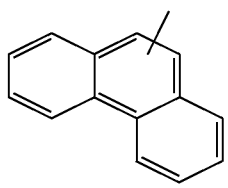.
Pyrenyl is 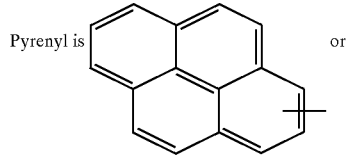 or

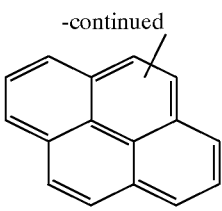

Furanyl is furan-2-yl or furan-3-yl.

Thiophenyl is thiophen-2-yl or thiophen-3-yl.

Pyridinyl is pyridin-2-yl, pyridin-3-yl or pyridin-4-yl.

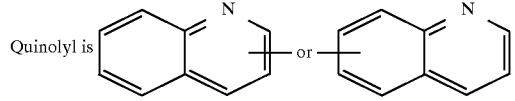

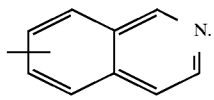

Substituted radicals phenyl, stilbenyl, biphenyl, o-, m- and p-terphenyl, triphenylphenyl, naphthyl, binaphthyl, anthracyl, phenanthryl, pyrenyl, ferrocenyl, furanyl, thiophenyl, pyridinyl, quinolinyl or isoquinolinyl are substituted one to four times, for example one, two or three times, especially two or three times. Substituents on the phenyl ring are preferably in positions 2 or in 2,6 or 2,4,6 configuration on the phenyl ring.

$C_1$–$C_{12}$Alkyl is linear or branched and is, for example, $C_{1-C8}$-, $C_1$–$C_6$- or $C_1$–$C_4$alkyl. Examples are methyl, ethyl, propyl, isopropyl, n-butyl, sec-butyl, isobutyl, tert-butyl, pentyl, hexyl, heptyl, 2,4,4-trimethylpentyl, 2-ethylhexyl, octyl, nonyl, decyl and dodecyl. $R_5$–$R_{15}$ are, for example, $C_1$–$C_8$alkyl, especially $C_1$–$C_6$alkyl, preferably $C_1$–$C_4$alkyl.

$C_3$–$C_{12}$Cycloalkyl is for example cyclopropyl, cyclopentyl, cyclohexyl, cyclooctyl, cyclododecyl, especially cyclopentyl and cyclohexyl, preferably cyclohexyl.

$C_2$–$C_8$Alkenyl radicals may be mono or polyunsaturated and are for example allyl, methallyl, 1,1-dimethylallyl, 1-butenyl, 3-butenyl, 2-butenyl, 1,3-pentadienyl, 5-hexenyl or 7-octenyl, especially allyl.

Phenyl-$C_1$–$C_6$alkyl is for example benzyl, phenylethyl, α-methylbenzyl, phenylpentyl, phenylhexyl or α,α-dimethylbenzyl, especially benzyl. Substituted phenyl-$C_1$–$C_5$alkyl is substituted one to four times, for example once, twice or three times, especially twice or three times, on the phenyl ring.

Naphthyl-$C_1$–$C_3$alkyl is for example naphthylmethyl, naphthylethyl, naphthylpropyl or naphthyl-1-methylethyl, especially naphthylmethyl. The alkyl unit can be either in position 1 or in position 2 on the naphthyl ring system. Substituted naphthyl-$C_1$–$C_3$alkyl is substituted one to four times, for example once, twice or three times, especially twice or three times, on the aromatic rings.

$C_1$–$C_{12}$Alkoxy is a linear or branched radical and is, for example, methoxy, ethoxy, propoxy, isopropoxy, n-butyloxy, sec-butyloxy, isobutyloxy, tert-butyloxy, pentyloxy, hexyloxy, heptyloxy, 2,4,4-trimethylpentyloxy, 2-ethylhexyloxy, octyloxy, nonyloxy, decyloxy or dodecyloxy, especially methoxy, ethoxy, propoxy, isopropoxy, n-butyloxy, sec-butyloxy, isobutyloxy or tert-butyloxy, preferably methoxy.

Halogen is fluorine, chlorine, bromine and iodine, especially fluorine, chlorine and bromine, preferably fluorine and chlorine. If $C_1$–$C_{12}$Alkyl is substituted one or more times by halogen, then there are for example 1 to 3 or 1 or 2 halogen substituents on the alkyl radical.

X as $C_1$–$C_{20}$alkylene is linear or branched alkylene, for example methylene, ethylene, propylene, 1-methylethylene 1,1-dimethylethylene, butylene, 1-methylpropylene, 2-methylpropylene, pentylene, hexylene, heptylene, octylene, nonylene, decylene, dodecylene, tetradecylene, hexadecylene or octadecylene. In particular, X is $C_1$–$C_{12}$alkylene, for example ethylene, decylene,

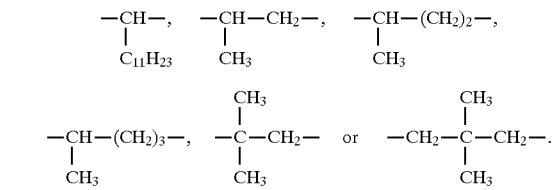

X as $C_2$–$C_{20}$ alkylene which is interrupted one or more times by —O—, —S(O)$_p$— or —NR$_{18}$— is, for example, interrupted 1–9 times, for example 1–7 times or once or twice by —O—, —S(O)$_p$— or —NR$_{18}$—. This produces structural units such as, for example, —CH$_2$—O—CH$_2$—, —CH$_2$—S—CH$_2$—, —CH$_2$—N(CH$_3$)—CH$_2$—, —CH$_2$CH$_2$—O—CH$_2$CH$_2$—, —[CH$_2$CH$_2$O]$_y$—,—[CH$_2$CH$_2$O]$_y$—CH$_2$—, where y=1–9, —(CH$_2$CH$_2$O)$_7$CH$_2$CH$_2$—, —CH$_2$—CH(CH$_3$)—O—CH$_2$—CH(CH$_3$)— or —CH$_2$—CH(CH$_3$)—O—CH$_2$—CH$_2$CH$_2$—. —OR$_6$-substituted $C_1$–$C_{20}$alkylene is, for example,

$C_3$–$C_{12}$Cycloalkylene is, for example, cyclopropylene, cyclopentylene, cyclohexylene, cyclooctylene, cyclododecylene, especially cyclopentylene and cyclohexylene, preferably cyclohexylene. $C_3$–$C_{12}$Cycloalkylene is also, however, for example, structural units such as

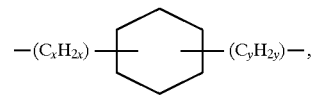

in which x and y independently of one another are 0–6 and the sum of x+y is $\leq 6$, or

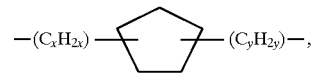

in which x and y independently of one another are 0–7 and the sum of x+y is $\leq 7$.

$C_2$–$C_8$Alkenylene can be mono- or polyunsaturated and is, for example, ethenylene, 1-propenylene, 1-butenylene, 3-butenylene, 2-butenylene, 1,3-pentadienylene, 5-hexenylene or 7-octenylene.

Examples of divalent aromatic hydrocarbon radicals are phenylene, stilbenylene, biphenylene, o-, m- and p-terphenylene, triphenylphenylene, naphthylene, binaphthylene, anthracenylene, phenanthrylene, pyrenylene, ferrocenylene, furanylene, thiophenylene, pyridinylene, quinolinylene or isoquinolinylene.

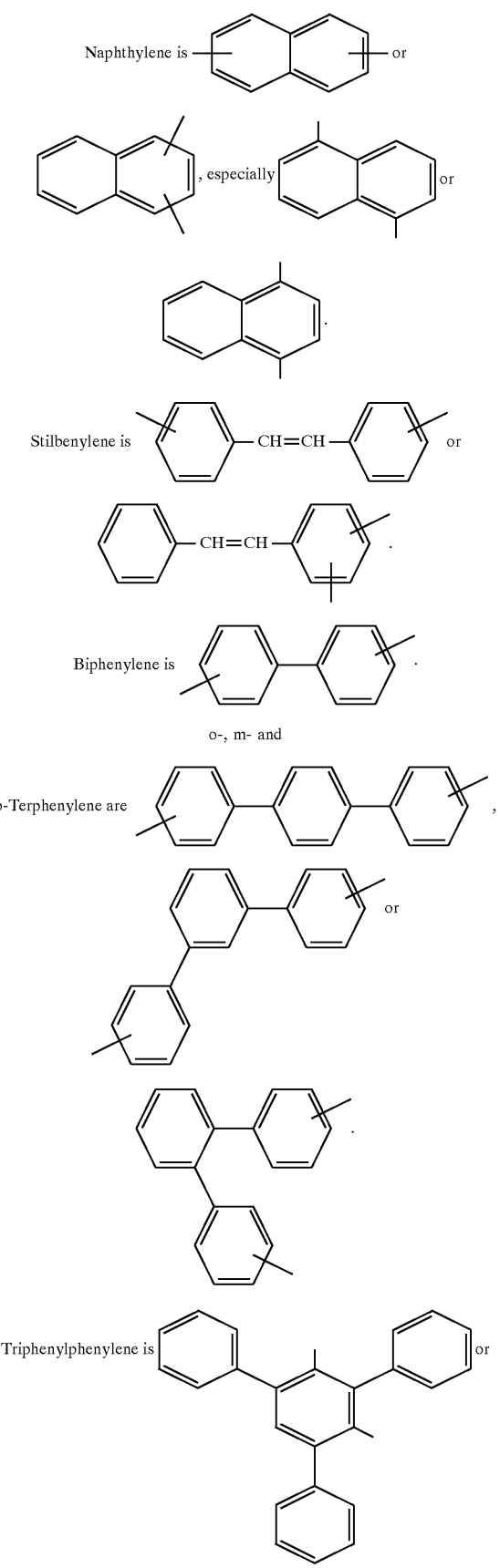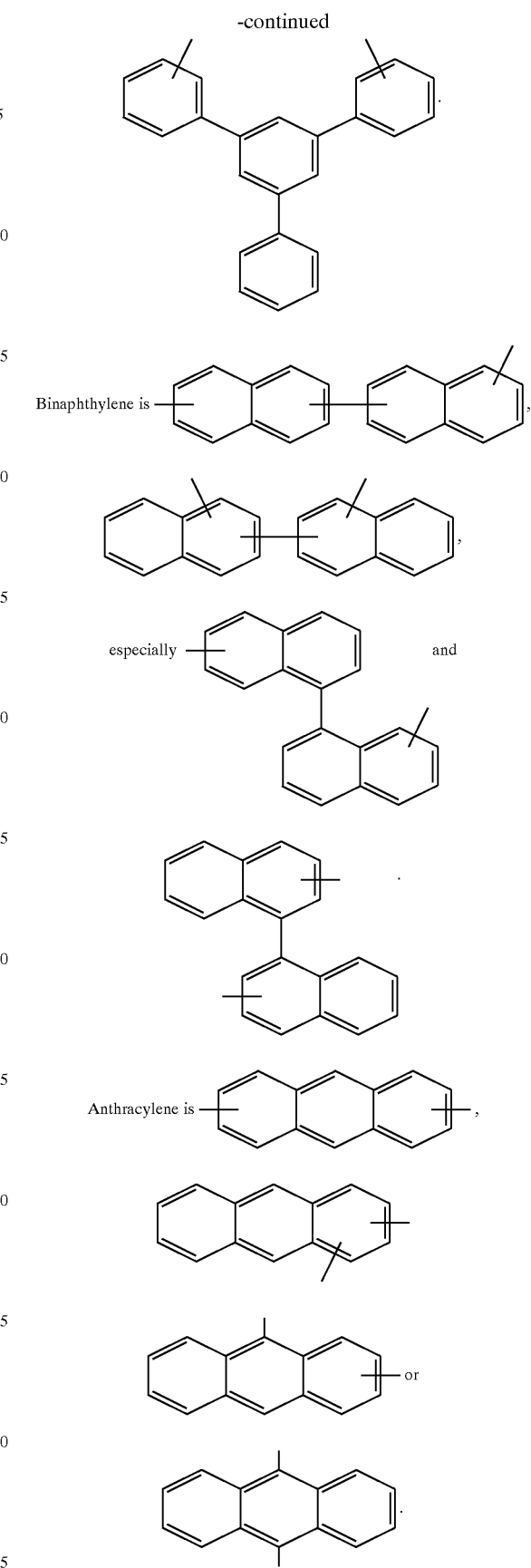

Phenanthrylene is 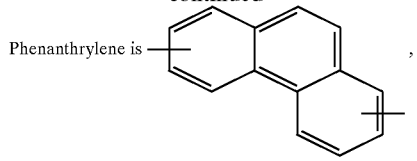,

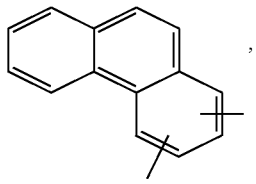,

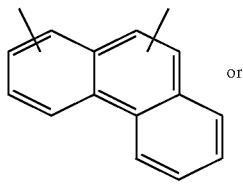 or

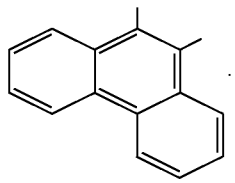.

Pyrenylene is 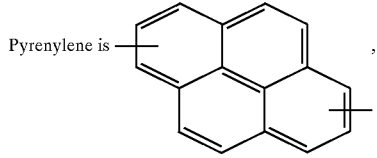,

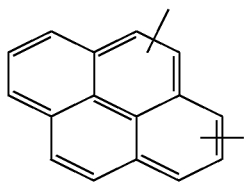,

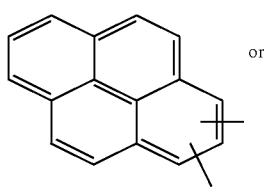 or

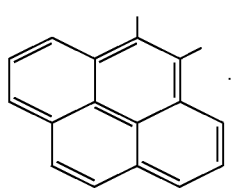.

Furanylene is 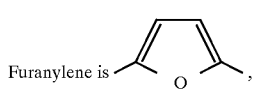,

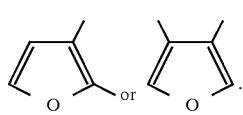.

Thiophenylene is 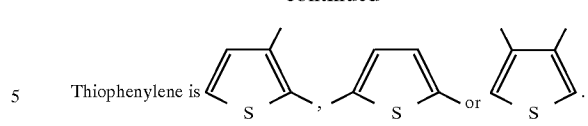.

Pyridinylene is 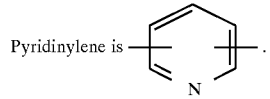.

Quinolinylene is 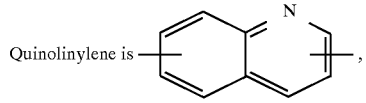,

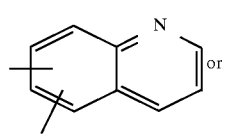 or

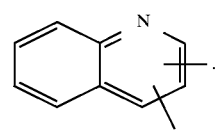.

Isoquinolinylene is 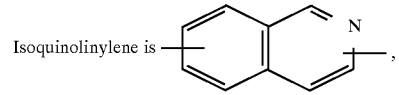,

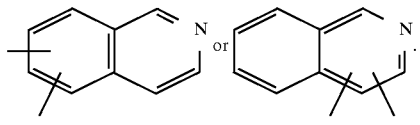.

1,4-Duryl is 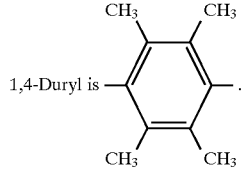.

Substituted radicals phenylene, stilbenylene, biphenylene, o-, m- or p-terphenylene triphenylphenylene, naphthylene, binaphthylene, anthracylene, phenanthrylene, pyrenylene, ferrocenylene, furanylene, thiophenylene, pyridinylene, quinolinylene or isoquinolinylene are substituted one to four times, for example once, twice or three times, especially once or twice. Substituents on the 1,4-phenylene ring are in position 2, 3, 5 or 6, especially in position 2 or 3 of the phenyl ring. Substituents on the 1,3-phenylene ring are in position 2, 4, 5 or 6, especially in position 4 or 5 of the phenyl ring.

Radicals suitable as a counterion $Z^+$ to the negative borate in the formula I are those which are able to form positive ions.

Examples of these are alkali metals, especially lithium or sodium, quaternary ammonium compounds, dye cations or cationic transition metal coordination complex compounds, especially ammonium or tetraalkylammonium.

Examples of tetraalkylammonium are, in particular, tetramethylammonium and tetrabutylammonium, although trisalkylammonium ions, for example trimethylammonium, are also suitable. Suitable phosphonium and ammonium counterions are those of the formulae $^+PR_wR_xR_yR_z$ and $^+NR_wR_xR_yR_z$, where $R_w$, $R_x$, $R_y$, $R_z$ independently of one another are hydrogen, unsubstituted or substituted alkyl, cycloalkyl, alkenyl, phenyl or arylalkyl. Substituents for these alkyl, cycloalkyl, alkenyl, phenyl or arylalkyl radicals are, for example, halide, hydroxyl, heterocycloalkyl (e.g. epoxy, aziridyl, oxetanyl, furanyl, pyrrolidinyl, pyrrolyl, thiophenyl, tetrahydrofuranyl, etc.), dialkylamino, amino, carboxyl, alkyl- and arylcarbonyl and aryloxy- and alkoxy-carbonyl.

The tetravalent nitrogen may also be part of a 5- or 6-membered ring, in which case this ring may in turn be fused to other ring systems. These systems may also contain additional heteroatoms, f or example S, N, O.

The tetravalent nitrogen may also be part of a polycyclic ring system, for example azoniapropellane. These systems m ay also contain further heteroatoms, for example S, N, O.

Also suitable are polyammonium salts and polyphosphonium salts, especially the bis salts, in which it is possible for the same substituents to be present as described above for the "mono" compounds.

The ammonium salts and phosphonium salts may also be substituted by neutral dyes (e.g. thioxanthenenes, thioxanthones, coumarins, ketocoumarins, etc.). Such salts are obtained by the reaction of the ammonium salts and phosphonium salts, substituted by reactive groups (e.g. epoxy, amino, hydroxyl, etc.), with appropriate derivatives of neutral dyes. Corresponding examples are described in EP-A 224 967 QUANTACURE QTX

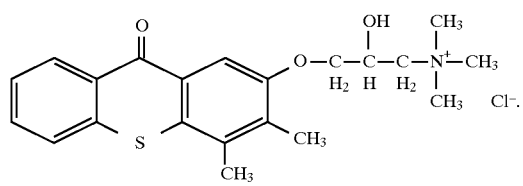

Similarly, ammonium salts and phosphonium salts can also be substituted by colourless electron acceptors (e.g. benzophenones); examples of these are QUANTACURE ABQ

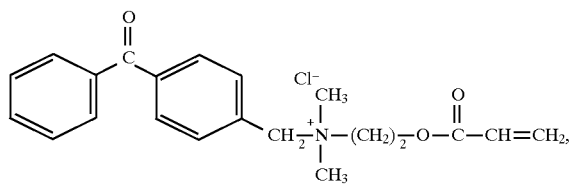

QUANTACURE BPQ

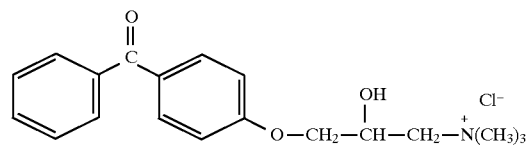

and QUANTACURE BTC

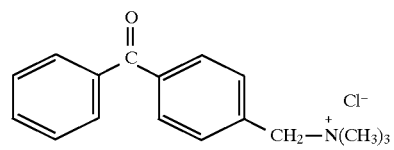

from International Bio-Synthetics.

Other quaternary ammonium compounds which are of interest are, for example, trimethylcetylammonium or cetylpyridinium compounds.

Other examples of ions to be used as positive counterions Z in the compound of the formula I include the following:

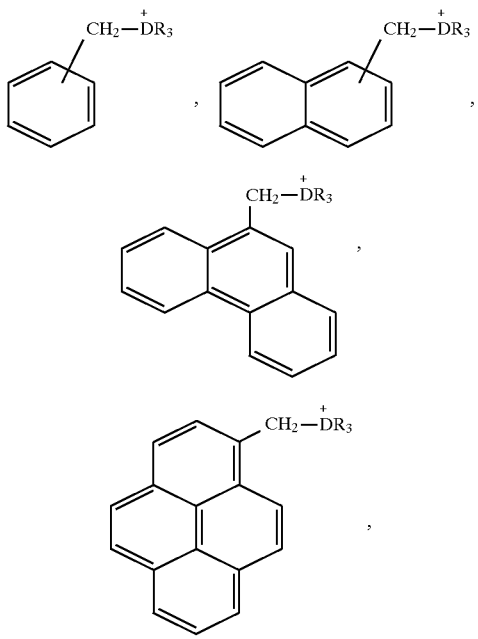

in which D is P, N or S and R is an alkyl or aryl radical. Also suitable are compounds such as

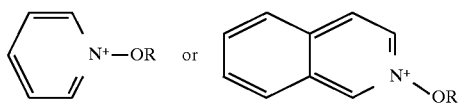

(described by Yagci et al. in J. Polym. Sci. Part A: Polymer Chem. 1992, 30, 1987 and Polymer 1993, 34(6), 1130), or compounds such as

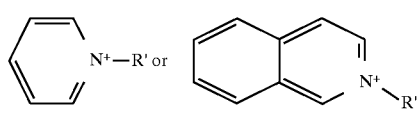

where R'=unsubstituted or substituted benzyl or phenacyl (described in JP-A Hei 7 70221). In these compounds, the aromatic rings in the pyridinium may also be substituted.

Other positive counterions $Z^+$ to the borate which can be employed are onium ions, for example iodonium or sulfonium ions.

Examples of such counterions to the borate are radicals of the formula

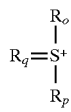

as described in EP-A 555 058 and EP-A 690 074. Also of interest as counterions are

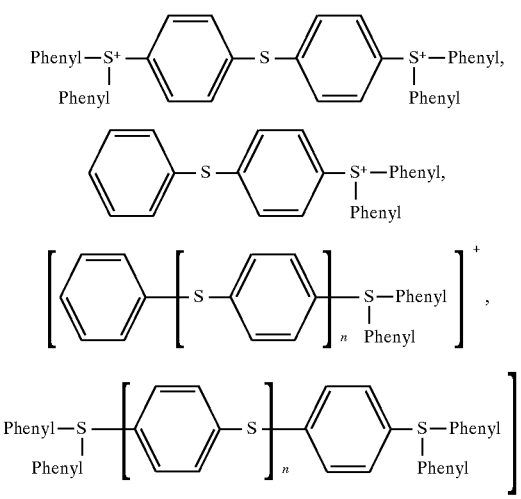

Further suitable counterions for the novel borates are cations of the formula,

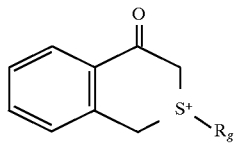

in which $R_g$ is an alkyl radical, especially ethyl, or is benzyl, and where the aromatic ring can carry further substituents. Other suitable counterions are halonium ions, especially diaryliodonium ions, as described for example in EP-A 334 056 and EP-A 562 897.

However, cations of ferrocenium salts are also suitable, as described in EP-A 94915 and EP A 109 851, for example

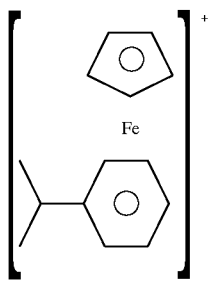

Other suitable onium cations, such as ammonium, phosphonium, sulfonium, iodonium, selonium, arsonium, tellonium and bismuthonium, are described, for example, in Japanese Patent Application Hei 6 266102.

Examples of cationic transition metal complex compounds which are suitable as counterions are described in U.S. Pat. No. 4,954,414. Of particular advantage are bis(2, 2'-bipyridine)(4,4'-dimethyl-2,2'-bipyridine)ruthenium, tris (4,4'-dimethyl-2,2'-bipyridine)ruthenium, tris(4,4'-dimethyl-2,2'-bipyridine)iron, tris(2,2',2"-terpyridine) ruthenium, tris(2,2'-bipyridine)ruthenium and bis(2,2'-bipyridine)(5-chloro-1,10-phenanthroline)ruthenium. Examples of suitable dyes are cations of triarylmethanes, for example malachite green, indolines, thiazines, for example methylene blue, xanthones, thioxanthones, oxazines, acridines, cyanines, rhodamines, phenazines, for example safranin, preferably cyanines and thioxanthones.

Some of the novel compounds exhibit good stability to acid and can therefore also be employed in acidic formulations, and also for example in combination with dyes containing acid groups.

The novel compounds of the formula I are prepared, for example, by addition of from one to m+v equivalents of an organometallic reagent onto a corresponding borane (Ib):

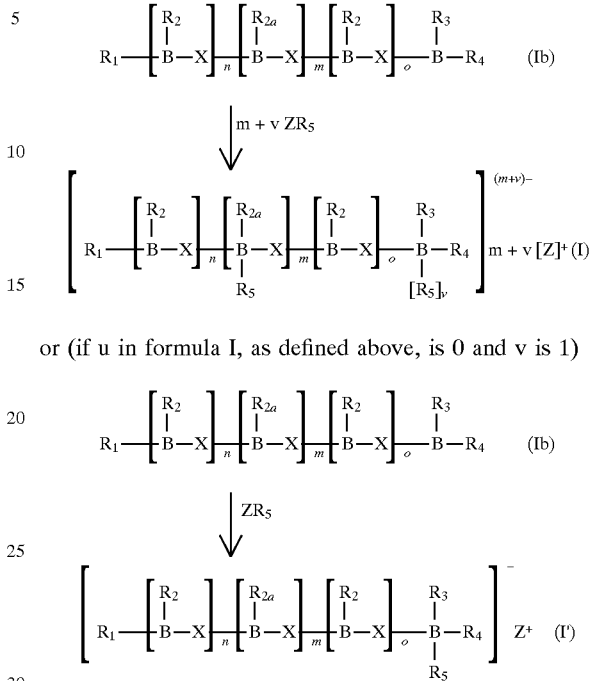

or (if u in formula I, as defined above, is 0 and v is 1)

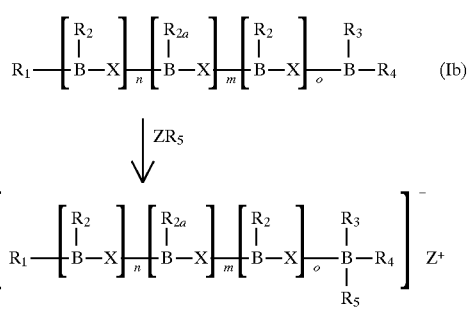

The definitions of the radicals are as given above.

It is also possible first to react the polyborane with an organometallic reagent $MR_5$ in which M is a metal atom, for example Li, Mg, etc., and then in a second reaction step to replace the metal cation in the formula Ib by a different cation $Z^+$ (e.g. tetraalkylammonium):

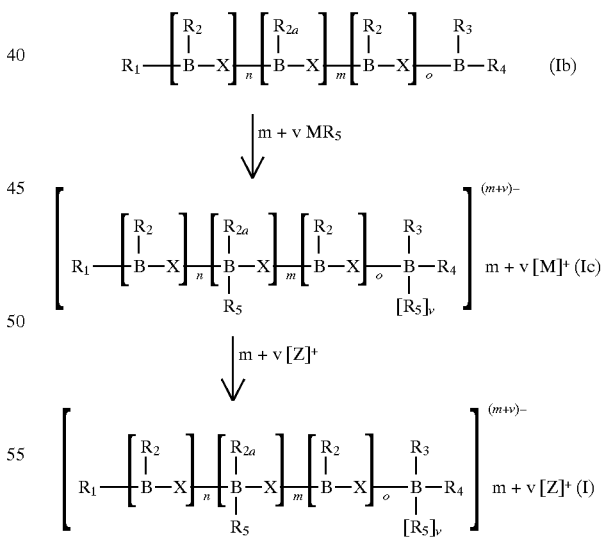

The reaction conditions for working with organometallic reagents are generally familiar to the skilled worker. Thus the reaction is expediently carried out in an inert organic solvent, for example an ether or aliphatic hydrocarbon, such as diethyl ether, tetrahydrofuran or hexane. Suitable organometallic reagents for preparing the novel polyborates are, for example, the lithium compounds of the corresponding aliphatic and aromatic hydrocarbon radicals. It is also possible, for example, to use Grignard reagents, zinc or sodium. The reaction with the organometallic reagent is expediently carried out with the exclusion of air in an inert gas atmosphere, for example under nitrogen. The reaction is generally performed with cooling to 0° C. or below followed by heating to room temperature. It is expedient to stir the reaction mixture. The products are isolated and purified by methods likewise generally known to the skilled worker, for example chromatography, recrystallization, etc. Thus, for example, impurities are expediently removed by washing the product with a boiling solvent, followed by filtration. It is also possible to obtain the polyborates directly from solution during the preparation of the polyborane precursors, without the isolation thereof beforehand.

Where the novel compounds of the formula I contain a dye radical as cation, they are prepared by the cation exchange reaction of an appropriate borate salt with a dye. Examples of the borate salts suitable for the exchange are the sodium, lithium, magnesium, ammonium or tetraalkylammonium salts. The novel polyboranes (Ia) are obtained, for example, by the addition of a borane reagent of the formula $ArBL_2$ or $Ar_2BL$, in which Ar is an aryl radical and L is a leaving group, onto a polymetalated compound. The latter is generally prepared by halogen$\leftarrow\rightarrow$metal exchange of a polyhalogenated aromatic compound with an organometallic reagent, for example butyllithium, or with a metal, for example magnesium. Polyboration can also be carried out in steps, for example by repeated sequences of monometalation/monoborylation. Polyboranes can, moreover, be converted, for example by reaction of metalated aryl compounds, generally aryllithium or arylmagnesium derivatives, into polydihaloborylated or polydialkoxyborylated and polydiaryloxyborylated aromatic compounds. The conditions for such reactions are generally familiar to the skilled worker and are as described above. However, the polyboration reactions are generally carried out at lower temperatures, for example −78° C.

Dimesitylfluoroborane, for example, can be prepared by the method of Pelter et al.; Tetrahedron 1993, 49, 2965. It is also commercially available. Bis(chloromesityl) fluoroborane and bis(dichloromesityl)fluoroborane can be obtained analogously from bromochloromesitylene. Diphenylisopropoxyborane and di-o-tolylisopropoxyborane can be synthesized, for example, by addition of two equivalents of an appropriate Grignard reagent onto triisopropoxyborane (cf. Cole et al., Organometallics, 1992, 11, 652). The corresponding diarylbromoboranes can be prepared, for example, by the method of Haubold et al., J. Organomet. Chem. 1986, 315, 1. Phenyldifluoroborane, for example, is obtained by reaction of phenyldibromoborane with titanium tetrafluoride (cf. Nahm et al., J. Organomet. Chem. 1972, 35, 9). 1,4-bis(difluoroboryl)benzene and 1,4-bis (dibromoboryl)benzene can also be prepared by the method described by Nielsen et al. in J. Amer. Chem. Soc. 1957, 79, 3081. The aryl halides required are either commercially available or can be prepared by methods known to the skilled worker and conventional in the art.

Boranes with chlorinated aromatic radicals, for example, can also be obtained by chlorination of the borane, for example:

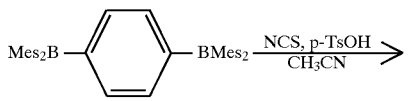

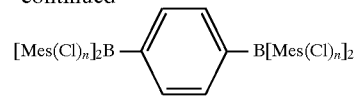

where Mes is mesityl, NCS is N-chlorosuccinimide, p-TsOH is p-toluenesulfonic acid and n is 1 or 2. Other chlorinating agents, for example chlorine gas, can also be employed.

Preferred compounds of the formula I are those in which n and o are both 0.

Other advantageous compounds of the formula I are those in which m is 1.

Attention is merited by the compounds of the formula I in which $R_1$, $R_{2a}$, $R_3$ und $R_4$ are identical.

Particular preference is given to those compounds of the formula I in which $R_1$, $R_{2a}$, $R_2$, $R_3$, $R_4$, $R_{14}$ and $R_{15}$ independently of one another are 2-, 2,6- or 2,4,6-substituted phenyl or are naphthyl or anthracyl.

Advantageous compounds of the formula I are those in which $R_1$, $R_{2a}$, $R_2$, $R_3$, $R_4$, $R_{14}$ and $R_{15}$ are $C_1-C_6$alkyl-, halo-, $OR_6$- or trifluoromethyl-substituted phenyl, 1-naphthyl or 1- or 9-anthracyl.

Also advantageous are compounds of the formula I in which $R_1$ is 1-naphthyl, 2-($C_1-C_6$alkyl)naphth-1-yl, 1-anthracyl, 9-anthracyl or ferrocenyl.

Preference is given, moreover, to the compounds of the formula I in which X is $C_1-C_{18}$-alkylene which is unsubstituted or substituted by $OR_6$, $NR_8R_9$, $SiR_{11}R_{12}R_{13}$, $BR_{14}R_{15}$ or halogen, or in which X is $C_1-C_{20}$alkylene which is interrupted by one or more groups —O—, or in which X is phenylene, biphenylene, o-, m- or p-terphenylene, naphthylene, phenanthrylene or ferrocenylene, where the radicals phenylene, biphenylene, o-, m- or p-terphenylene, naphthylene, phenanthrylene or ferrocenylene are unsubstituted or substituted by $C_1-C_6$alkyl, $OR_6$, $NR_8R_9$, $C(O)OR_6$, $C(O)NR_8R_9$, $C(O)R_{10}$, $SiR_{11}R_{12}R_{13}$, $BR_{14}R_{15}$ or halogen, or in which X is a radical of the formula II in which Y is —$(CH_2)_r$—, —C(O)—, —N—, —O—, —S(O)$_p$—, —$CR_{19}R_{20}$—,

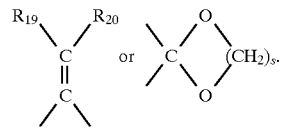

Other preferred compounds of the formula I are those in which n and o are both 0, m is the number 1, $R_1$, $R_{2a}$, $R_2$, $R_3$ and $R_4$ are phenyl substituted by $C_1-C_6$alkyl and/or halogen, especially chlorine, $R_5$ is $C_1-C_{12}$alkyl, $(C_1-C_4$alkyl$)_3$Si-$CH_2$- or phenyl, X is unsubstituted phenylene, halo-substituted, especially fluoro-substituted, phenylene, biphenylene, o- or p-terphenylene, naphthylene, phenanthrylene, ferrocenylene or a radical of the formula II in which Y is —C(O)— or

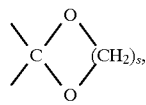

s is 2, and

Z is tetraalkylammonium, a cyanine-dye cation or a thioxanthon cation.

In the prior art, borates have been used to date in combination with coinitiator compounds or electron acceptor compounds, respectively, for example dyes or transition metal complexes, as photoinitiators. It has now surprisingly been found that the combinations of polyboranes with coinitiators or electron donor compounds, for example borates, also have good photoinitiator properties.

The invention therefore additionally provides a photoinitiator comprising A) at least one borane of the formula VI

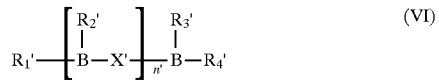

in which n' is a number from 0 to 50;

$R_1'$, $R_2'$, $R_3'$ and $R_4'$ are phenyl or another aromatic hydrocarbon, which radicals are unsubstituted or are substituted by unsubstituted or halo-, $OR_6'$- and/or $NR_8'R_9'$-substituted $C_1$–$C_6$alkyl, $OR_6'$, $S(O)_pR_7'$, $OS(O)_2R_7'$, $NR_8'R_9'$, $C(O)NR_8'R_9'$, $C(O)R_{10}'$, $SiR_{11}'R_{12}'R_{13}'$, $BR_{14}'R_{15}'$, halogen and/or $P(O)_{q'}R_{16}'R_{17}'$, at least one of the radicals $R_1'$, $R_2'$, $R_3'$, and $R_4'$ being a phenyl radical which is substituted ortho to the bond to the boron atom or being another aromatic hydrocarbon radical which is sterically hindered ortho to the boron atom;

p' is a number from 0 to 2;

$R_6'$ and $R_7'$ independently of one another are unsubstituted or $COOR_{7a}$, OH, $C_1$–$C_{12}$alkoxy, CN or halo-substituted $C_1$–$C_{12}$alkyl, phenyl or phenyl-$C_1$–$C_6$alkyl, where the radicals phenyl or phenyl-$C_1$–$C_6$alkyl are unsubstituted or substituted one to five times by $C_1$–$C_6$alkyl, $C_1$–$C_{12}$alkoxy or halogen;

$R_{7a}$ is $C_1$–$C_{12}$alkyl;

$R_8'$, $R_9'$, $R_{10}'$, $R_{11}'$, $R_{12}'$, $R_{13}'$, $R_{14}'$ and $R_{15}'$ independently of one another are as defined for $R_6'$ or are $C_3$–$C_{12}$cycloalkyl, or $R_8'$ and $R_9'$, together with the N atom to which they are attached, form a 5- or 6-membered ring which may additionally contain O or S atoms, or $R_{14}'$ and $R_{15}'$, together with the B atom to which they are attached, form a 5- or 6-membered ring;

$R_{16}'$ and $R_{17}'$ independently of one another are as defined for $R_{10}'$;

q' is 0 or 1; and

X' is $C_1$–$C_{20}$alkylene which is unsubstituted or substituted by $OR_6'$, $S(O)_pR_7'$, $OS(O)_2R_7'$, $NR_8'R_9'$, $C(O)OR_6'$, $C(O)NR_8'R_9'$, $C(O)R_{10}'$, $SiR_{11}'R_{12}'R_{13}'$, $BR_{14}'R_{15}'$, halogen or $P(O)_{q'}R_{16}'R_{17}'$, or X' is $C_1$–$C_{20}$alkylene which is interrupted by one or more groups —O—, —S(O)$_{p'}$— or —NR$_{18}'$—, or X' is $C_3$–$C_{12}$cycloalkylene or $C_2$–$C_8$alkenylene, which radicals are unsubstituted or substituted by $OR_6'$, $S(O)_pR_7'$, $OS(O)_2R_7'$, $NR_8'R_9'$, $C(O)OR_6'$, $C(O)NR_8'R_9'$, $C(O)R_{10}'$, $SiR_{11}'R_{12}'R_{13}'$, $BR_{14}'R_{15}'$, halogen or $P(O)_{q'}R_{16}'R_{17}'$, or are interrupted by one or more groups —O—, —S(O)$_{p'}$— or —NR$_{18}'$—, or X' is a divalent aromatic hydrocarbon radical which is unsubstituted or substituted by $C_1$–$C_6$alkyl, $OR_6'$, $S(O)_pR_7'$, $OS(O)_2R_7'$, $NR_8'R_9'$, $C(O)OR_6'$, $C(O)NR_8'R_9'$, $C(O)R_{10}'$, $SiR_{11}'R_{12}'R_{13}'$, $BR_{14}'R_{15}'$, halogen or $P(O)_{q'}R_{16}'R_{17}'$, or X' is a radical of the formula VII or VIII

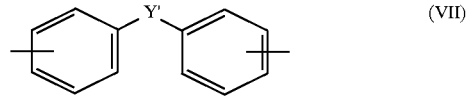

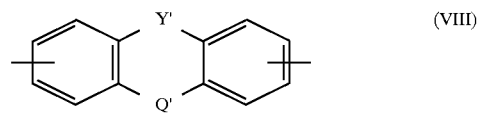

in which

Y' is —(CH$_2$)$_{r'}$—, —C(O)—, —NR$_{18}'$, —O—, —S(O)$_{p'}$—, —CR$_{19}'$R$_{20}'$—,

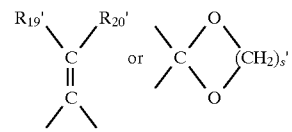

r' is 1, 2 or 3;

s' is 2 or 3;

$R_{18}'$ is as defined for $R_6'$ or is hydrogen;

$R_{19}'$ and $R_{20}'$ are $C_1$–$C_6$alkyl or phenyl, or $R_{19}'$ and $R_{20}'$, together with the C atom to which they are attached, form a 5- or 6-membered ring;

A' and Q' independently of one another are a direct bond, —(CH$_2$)$_{r'}$—, —CH=CH— —C(O)—, —NR$_{18}'$— or —S(O)$_{p'}$—, —CR$_{19}'$R$_{20}'$—,

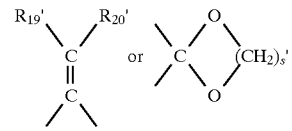

or the radicals $R_1'$, $R_2'$, $R_3'$, $R_4'$ or X' form bridges to produce radicals of the formula (IX) or (X)

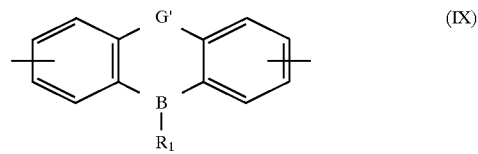

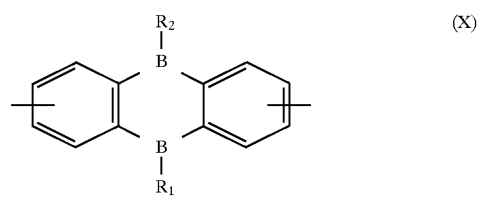

in which

G' is —(CH$_2$)$_{r'}$—, —CHCH—, —C(O)—, —NR$_{18}'$—, —O— or —S(O)$_{p'}$—, —CR$_{19}'$R$_{20}'$—,

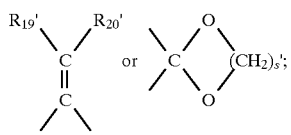

and t' is 0, 1 or 2,;

the radicals of the formulae (VII), (VIII), (IX) and (X) being unsubstituted or substituted on the aromatic rings by $OR_6'$, $S(O)_pR_7'$, $OS(O)_2R_7'$, $NR_8'R_9'$, $C(O)OR_6'$, $C(O)NR_8'R_9'$, $C(O)R_{10}'$, $SiR_{11}'R_{12}'R_{13}'$, $BR_{14}'R_{15}'$ or halogen and it being possible for further phenyl rings to be fused to the phenyl rings of the formulae (VII), (VIII), (IX) and (X); and B) at least one electron donor compound.

The invention additionally provides photoinitiators comprising as component B) at least one compound of the formula I and/or at least one compound of the formula XI

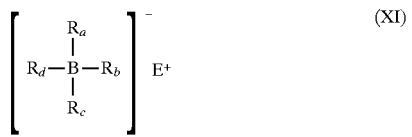

in which $R_a$, $R_b$, $R_c$ and $R_d$ independently of one another are $C_1$–$C_{12}$alkyl, trimethylsilylmethyl, phenyl, another aromatic hydrocarbon, $C_1$–$C_6$alkylphenyl, allyl, phenyl-$C_1$–$C_6$alkyl, $C_2$–$C_8$alkenyl, $C_2$–$C_8$alkynyl, $C_3$–$C_{12}$cycloalkyl or saturated or unsaturated heterocyclic radicals, wherein the radicals phenyl, another aromatic hydrocarbon, phenyl-$C_1$–$C_6$alkyl and saturated or unsaturated heterocyclic radical ar unsubstituted or substituted by unsubstituted or halo-, $OR_6$- and/or $NR_8R_9$-substituted $C_1$–$C_6$alkyl, $OR_6$, $S(O)_pR_7$, $OS(O)_2R_7$, $NR_8R_9$, $C(O)OR_6$, $C(O)NR_8R_9$, $C(O)R_{10}$, $SiR_{11}R_{12}R_{13}$, $BR_{14}R_{15}$, $P(O)_qR_{16}R_{17}$ or halogen;

p is 0, 1 or 2;

q is 0 or 1;

$R_6$ and $R_7$ are unsubstituted or $COOR_{7a}$, OH, $C_1$–$C_{12}$alkoxy- or halo-substituted $C_1$–$C_{12}$alkyl, unsubstituted or mono- to penta-$C_1$–$C_6$alkyl-, -$C_1$–$C_{12}$alkoxy- or -halo-substituted phenyl, or unsubstituted or mono- to penta-$C_1$–$C_6$alkyl-, -$C_1$–$C_{12}$alkoxy- or -halo-substituted phenyl-$C_1$–$C_6$alkyl;

$R_{7a}$ is $C_1$–$C_{12}$alkyl;

$R_8$, $R_9$, $R_{10}$, $R_{11}$, $R_{12}$, $R_{13}$, $R_{14}$ and $R_{15}$ independently of one another are as defined for $R_6$ or are $C_3$–$C_{12}$cycloalkyl, or $R_8$ and $R_9$, together with the N atom to which they are attached, form a 5- or 6-membered ring which may additionally contain O or S atoms, or $R_{14}$ and $R_{15}$, together with the B atom to which they are attached, form a 5- or 6-membered ring;

$R_{16}$ and $R_{17}$ independently of one another are as defined for $R_6$ or are $C_3$–$C_{12}$cycloalkyl; and E is a radical which is able to form positive ions, especially alkali metals, ammonium, tetraalkylammonium, phosphonium- or sulphonium radical.

The definitions of aromatic hydrocarbons, $C_1$–$C_{12}$alkyl, $C_3$–$C_{12}$cycloalkyl, $C_2$–$C_8$alkenyl and phenyl-$C_1$–$C_6$alkyl, $R_6$–$R_{17}$ are as given above. $C_1$–$C_6$Alkylphenyl is phenyl which is substituted one to four times, for example one to three times, especially once, by $C_1$–$C_6$alkyl-substituted phenyl. $C_1$–$C_6$Alkyl can have the same definitions as described above for $C_1$–$C_{12}$alkyl up to the corresponding number of C atoms. $C_2$–$C_8$Alkynyl is, in particular, ethynyl. E as a radical which forms positive ions has one of the definitions described above for Z.

Coinitiators used in accordance with the present invention are either electron acceptor compounds (in combination with novel borates of the formula I) or electron donor compounds (in combination with polyboranes of the formula VI). Thus in this context the term coinitiator refers, for example, to sensitizers, such as thioxanthones, to reaction accelerators, such as amines, thiols, etc., or to dyes. Examples of suitable electron donor compounds are borates, for example those of the formulae I and XI, such as triphenyl butyl borate, thiols, amines, for example triethanolamine, N-phenylglycine or (2,5-dimethyl)-1-thia-3,4-diazole, organotin compounds, for example benzyltrimethylstannane, phosphines, arsines, for example triphenylphosphine or triphenylarsine, as described for example in JP-A Hei 6 263809, sulfinates, for example sodium p-toluenesulfinate, or carboxylates, for example ascorbic acid. Coinitiators of this kind are described, for example, in Chemistry & Technology of UV & EB Formulation for Coatings, Inks & Paints, Vol.3, page 344–348 (London, 1991).

It is of course also possible to add further coinitiaors or electron acceptor compounds, for example dyes, to the photoinitiators described above. The invention therefore additionally provides a photoinitiator which in addition to components A) and B) comprises at least one coinitiator or electron acceptor compound (C).

As already mentioned, the novel polyborate compounds of the formula I can be employed per se as photoinitiators. However, it is also possible to use them in combination with coinitiators or electron acceptor compounds as photoinitiators. The invention therefore additionally provides a photoinitiator comprising at least one compound of the formula I according to claim 1 and at least one coinititator or electron acceptor compound. Examples of suitable electron acceptor compounds are transition metal complex compounds or dyes. Suitable transition metal complex compounds, for example, are described in U.S. Pat. No. 4,954,414, examples being bis(2,2'-bipyridine)(4,4'-dimethyl-2,2'-bipyridine)-ruthenium, tris(4,4'-dimethyl-2,2'-bipyridine)ruthenium, tris(4,4'-dimethyl-2,2'-bipyridine)iron, tris(2,2',2"-terpyridine) ruthenium, tris(2,2'-bipyridine)ruthenium and bis(2,2'-bipyridin)-(5-chloro-1,10-phenanthroline)ruthenium. Suitable dyes which can be added as coinitiators (electron acceptor compounds) are described, for example, in U.S. Pat. No. 5,151,520. They are, by way of example, triarylmethanes, such as malachite green, indolines, thiazines, such as methylene blue, xanthones, thioxanthones, oxazines, acridines or phenazines, such as safranin. Particularly suitable dyes are malachite green, methylene blue, safranin O, rhodamines of the formula

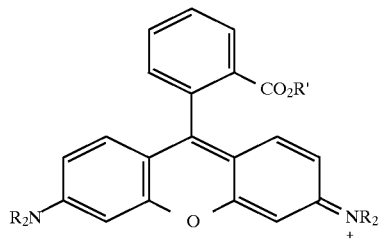

in which R is alkyl or aryl and R' is hydrogen, alkyl or aryl, for example rhodamine B, rhodamine 6G or violamine R, and also sulforhodamine B or sulforhodamine G.

Other suitable dyes are fluorones, as described for example by Neckers et al. in J. Polym. Sci., Part A, Poly. Chem, 1995, 33, 1691–1703.

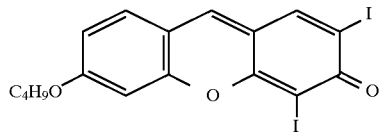

is of particular interest.

Examples of further suitable dyes are cyanines of the formula

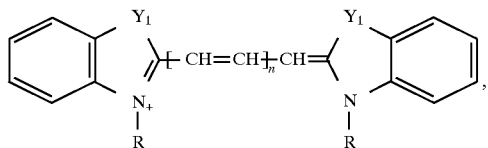

in which R=alkyl; n=0,1,2,3 or 4 and $Y_1$=CH=CH, N—CH$_3$, C(CH$_3$)$_2$, O, S, Se. Preferred cyanines are those in which $Y_1$ in the above formula is C(CH$_3$)$_2$ or S.

The following dye compounds are also suitable as coinitiators:

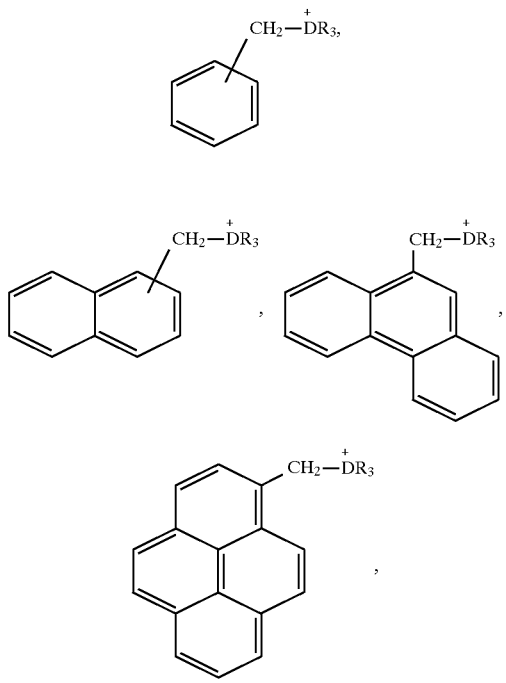

in which D is P, N or S and R is an alkyl or aryl radical. Preferred compounds of the above formula are those in which DR$_3$ is N(CH$_3$)$_3$, N(C$_2$H$_5$)$_3$ or P(C$_6$H$_5$)$_3$. Also suitable are compounds such as, for example,

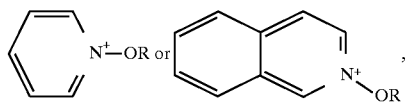

as described for example by Yagci et al. in J. Polym. Sci. Part A: Polymer Chem. 1992, 30, 1987 and Polymer 1993, 34(6), 1130, or such as, for example,

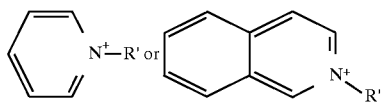

where R'=unsubstituted or substituted benzyl or phenacyl, described in JP-A Hei 7 70221. The abovementioned pyridinium compounds may also be substituted in the aromatic pyridinium ring.

Other suitable dyes can be found, for example, in U.S. Pat. No. 4,902,604. These are azulene dyes. Of particular advantage as coinitiators for the novel compounds are the compounds 1–18 listed in columns 10 and 11 of this patent, in the Table. Examples of further suitable dyes are merocyanine dyes, as described in U.S. Pat. No. 4,950,581 from column 6, line 20 to column 9, line 57.

As coinitiators for the novel compounds and photoinitiators it is also possible to use coumarin compounds. Examples of these are given in U.S. Pat. No. 4,950,581 in column 11, line 20 to column 12, line 42.

Other suitable coinitiators are xanthones or thioxanthones as described, for example, in U.S. Pat. No. 4,950,581, column 12, line 44 to column 13, line 15.

Anionic dye compounds can also be employed as coinitiators and electron acceptor compounds. For instance, Rose Bengal, eosine or fluorescein are also suitable. Other suitable dyes, for example from the triarylmethane class or azo class can be found in U.S. Pat. No. 5,143,818. Examples are Ethyl Orange (Chem. Abstr. Reg. No. 62758-12-7), Brilliant Blue G (Chem. Abstr. Reg. No.6104-58-1), Brilliant Blue R (Chem. Abstr. Reg. No.6104-59-2), Lissamine Green B (Chem. Abstr. Reg. No. 3087-16-9) or Patent Blue VF (Chem. Abstr. Reg. No.129-17-9).

In accordance with the invention, the compounds of the formula I can be used as photoinitiators for the photopolymerization of ethylenically unsaturated compounds and mixtures containing such compounds. This use may also be implemented in combination with another photoinitiator and/or with other additives.

The invention therefore relates in addition to photopolymerizable compositions comprising (a) at least one ethylenically unsaturated photopolymerizable compound and (b) at least one compound of the formula I, it being possible for the composition to comprise, in addition to components (a) and (b), other photoinitiators and/or other additives.

Furthermore, the invention provides a composition comprising in addition to components (a) and (b) at least one compound of the formula XI

in which $R_a$, $R_b$, $R_c$ and $R_d$ independently of one another are $C_1$–$C_{12}$alkyl, trimethylsilylmethyl, phenyl, another aromatic hydrocarbon, $C_1$–$C_6$alkylphenyl, allyl, phenyl-$C_1$–$C_6$alkyl, $C_2$–$C_8$alkenyl, $C_2$–$C_8$alkynyl, $C_3$–$C_{12}$cycloalkyl or saturated or unsaturated heterocyclic radicals, wherein the radicals phenyl, another aromatic hydrocarbon, phenyl-$C_1$–$C_6$alkyl and saturated or unsaturated heterocyclic radical ar unsubstituted or substituted by unsubstituted or halo-, $OR_6$- and/or $NR_8R_9$-substituted $C_1$–$C_6$alkyl, $OR_6$, $S(O)_pR_7$, $OS(O)_2R_7$, $NR_8R_9$, $C(O)OR_6$, $C(O)NR_8R_9$, $C(O)R_{10}$, $SiR_{11}R_{12}R_{13}$, $BR_{14}R_{15}$, $P(O)_qR_{16}R_{17}$ or halogen;

p is 0, 1 or 2;

q is 0 or 1;

$R_6$ and $R_7$ are unsubstituted or $COOR_{7a}$, OH, $C_1-C_{12}$alkoxy- or halo-substituted $C_1-C_{12}$alkyl, unsubstituted or mono- to penta-$C_1-C_6$alkyl-, -$C_1-C_{12}$alkoxy- or -halo-substituted phenyl, or unsubstituted or mono- to penta-$C_1-C_6$alkyl-, -$C_1-C_{12}$alkoxy- or -halo-substituted phenyl-$C_1-C_6$alkyl;

$R_{7a}$ is $C_1-C_{12}$alkyl;

$R_8$, $R_9$, $R_{10}$, $R_{11}$, $R_{12}$, $R_{13}$, $R_{14}$ and $R_{15}$ independently of one another are as defined for $R_6$ or are $C_3-C_{12}$cycloalkyl, or $R_8$ and $R_9$, together with the N atom to which they are attached, form a 5- or 6-membered ring which may additionally contain O or S atoms, or $R_{14}$ and $R_{15}$, together with the B atom to which they are attached, form a 5- or 6-membered ring;

$R_{16}$ and $R_{17}$ independently of one another are as defined for $R_6$ or are $C_3-C_{12}$cycloalkyl; and E is a radical which is able to form positive ions, especially an alkali metal, ammonium, tetraalkylammoinium, sulfonium- or phosphonium radical.

As already mentioned, it is advantageous to combine the novel borate compounds with coinitiators, for example inter alia sensitizers (=energy transfer compounds). In this context, additionally and particularly, combinations with two or more different coinitiators or sensitizers, for example mixtures of the novel borate compounds with onium salts and thioxanthones or coumarins or dyes, are highly effective. Preferred onium salts in these mixtures are diphenyliodonium hexafluorophosphate, (p-octyloxyphenyl)(phenyl) iodonium hexafluorophosphate, or corresponding other anions of these compounds, for example the halides; and also sulfonium salts, for example triarylsulfonium salts (Cyracure® UVI 6990, Cyracure® UVI-6974 from Union Carbide; Degacure® KI 85 from Degussa or SP-150 und SP-170 from Asahi Denka). Preference is given, for example, to a mixture of the novel borate compounds with diphenyliodonium hexafluorophosphate and isopropylthioxanthone, to a mixture of the novel borate compounds with (p-octyloxyphenyl)(phenyl)iodonium hexafluorophosphate and isopropylthioxanthone, and to a mixture of the novel borate compounds with

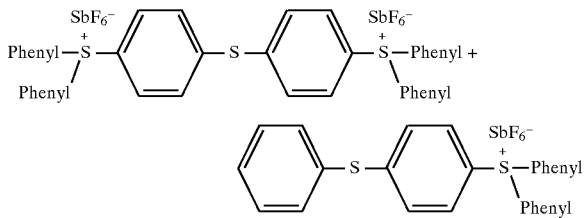

(=Cyracure® UVI-6974) and isopropylthioxanthone. However, it is particularly advantageous to add yet another photoinitiator, of the α-amino ketone type, to the abovementioned mixtures. For example, mixtures of the novel borates with onium salts and thioxanthones or dyes and a-amino ketones are highly effective. A preferred example is the mixture of the novel borate compounds with diphenyliodonium hexafluorophosphate or (p-octyloxyphenyl) (phenyl)iodonium hexafluorophosphate, isopropylthioxanthone and (4-methylthiobenzoyl)methyl-1-morpholinoethane.

The invention therefore also provides a composition comprising in addition to components (a) and (b) at least one neutral, anionic or cationic dye or a thioxanthone compound and an onium compound. The abovementioned onium compounds are preferred.

The invention additionally provides a composition comprising in addition to components (a) and (b) at least one neutral, anionic or cationic dye and an onium compound and a free-radical photoinitiator, especially an a-amino ketone compound.

The unsaturated compounds may include one or more olefinic double bonds. They may be of low (monomeric) or high (oligomeric) molecular mass. Examples of monomers containing a double bond are alkyl or hydroxyalkyl acrylates or methacrylates, such as methyl, ethyl, butyl, 2-ethylhexyl and 2-hydroxyethyl acrylate, isobornyl acrylate, methyl methacrylate and ethyl methacrylate. Silicone acrylates are also advantageous. Other examples are acrylonitrile, acrylamide, methacrylamide, N-substituted (meth) acrylamides, vinyl esters such as vinyl acetate, vinyl ethers such as isobutyl vinyl ether, styrene, alkyl- and halostyrenes, N-vinylpyrrolidone, vinyl chloride and vinylidene chloride.

Examples of monomers containing two or more double bonds are the diacrylates of ethylene glycol, propylene glycol, neopentyl glycol, hexamethylene glycol and of bisphenol A, and 4,4'-bis(2-acryloyloxyethoxy) diphenylpropane, trimethylolpropane triacrylate, pentaerythritol triacrylate or tetraacrylate, vinyl acrylate, divinylbenzene, divinyl succinate, diallyl phthalate, triallyl phosphate, triallyl isocyanurate or tris(2-acryloylethyl) isocyanurate.

Examples of polyunsaturated compounds of relatively high molecular mass (oligomers) are acrylisized epoxy resins, acrylisized polyesters, polyesters containing vinyl ether or epoxy groups, and also polyurethanes and polyethers. Further examples of unsaturated oligomers are unsaturated polyester resins, which are usually prepared from maleic acid, phthalic acid and one or more diols and have molecular weights of from about 500 to 3000. In addition it is also possible to employ vinyl ether monomers and oligomers, and also maleate-terminated oligomers with polyester, polyurethane, polyether, polyvinyl ether and epoxide main chains. Of particular suitability are combinations of oligomers which carry vinyl ether groups and of polymers as described in WO 90/01512. However, copolymers of vinyl ether and maleic acid-functionalized monomers are also suitable. Unsaturated oligomers of this kind can also be referred to as prepolymers.

Particularly suitable examples are esters of ethylenically unsaturated carboxylic acids and polyols or polyepoxides, and polymers having ethylenically unsaturated groups in the chain or in side groups, for example unsaturated polyesters, polyamides and polyurethanes and copolymers thereof, alkyd resins, polybutadiene and butadiene copolymers, polyisoprene and isoprene copolymers, polymers and copolymers containing (meth)acrylic groups in side chains, and also mixtures of one or more such polymers.

Examples of unsaturated carboxylic acids are acrylic acid, methacrylic acid, crotonic acid, itaconic acid, cinnamic acid, and unsaturated fatty acids such as linolenic acid or oleic acid. Acrylic and methacrylic acid are preferred.

Suitable polyols are aromatic and, in particular, aliphatic and cycloaliphatic polyols. Examples of aromatic polyols are hydroquinone, 4,4'-dihydroxybiphenyl, 2,2-di(4-hydroxyphenyl)propane, and also novolaks and resols. Examples of polyepoxides are those based on the abovementioned polyols, especially the aromatic polyols, and epichlorohydrin. Other suitable polyols are polymers and copolymers containing hydroxyl groups in the polymer chain or in side groups, examples being polyvinyl alcohol and copolymers thereof or polyhydroxyalkyl methacrylates or copolymers thereof. Further suitable polyols are oligoesters having hydroxyl end groups.

Examples of aliphatic and cycloaliphatic polyols are alkylenediols having preferably 2 to 12 C atoms, such as ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols having molecular weights of preferably from 200 to 1500,1 ,3-cyclopentanediol, 1,2-, 1,3- or 1,4-cyclohexanediol, 1,4-dihydroxymethylcyclohexane, glycerol, tris(β-hydroxyethyl)amine, trimethylolethane, trimethylolpropane, pentaerythritol, dipentaerythritol and sorbitol.

The polyols may be partially or completely esterified with one or with different unsaturated carboxylic acids, and in partial esters the free hydroxyl groups may be modified, for example etherified or esterified with other carboxylic acids.

Examples of esters are: trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octaacrylate, pentaerythritol dimethacrylate, pentaerythritol trimethacrylate, dipentaerythritol dimethacrylate, dipentaerythritol tetramethacrylate, tripentaerythritol octamethacrylate, pentaerythritol diitaconate, dipentaerythritol trisitaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetra-methacrylate, sorbitol pentaacrylate, sorbitol hexaacrylate, oligoester acrylates and methacrylates, glycerol diacrylate and triacrylate, 1,4-cyclohexane diacrylate, bisacrylates and bismethacrylates of polyethylene glycol with a molecular weight of from 200 to 1500, or mixtures thereof.

Also suitable as component (a) are the amides of identical or different, unsaturated carboxylic acids with aromatic, cycloaliphatic and aliphatic polyamines having preferably 2 to 6, especially 2 to 4, amino groups. Examples of such polyamines are ethylenediamine, 1,2- or 1,3-propylenediamine, 1,2-, 1,3- or 1,4-butylenediamine, 1,5-pentylenediamine, 1,6-hexylenediamine, octylenediamine, dodecylenediamine, 1,4-diaminocyclohexane, isophoronediamine, phaenylenediamine, bisphenylenediamine, di-β-aminoethyl ether, diethylenetriamine, triethylenetetramine, di(β-aminoethoxy)- or di(β-aminopropoxy)ethane. Other suitable polyamines are polymers and copolymers, preferably with additional amino groups in the side chain, and oligoamides having amino end groups. Examples of such unsaturated amides are methylenebisacrylamide, 1,6-hexamethylenebisacrylamide, diethylenetriaminetrismethacrylamide, bis(methacrylamidopropoxy)ethane, β-methacrylamidoethyl methacrylate and N-[(β-hydroxyethoxy)ethyl]acrylamide.

Suitable unsaturated polyesters and polyamides are derived, for example, from maleic acid and from diols or diamines. Some of the maleic acid can be replaced by other dicarboxylic acids. They can be used together with ethylenically unsaturated comonomers, for example styrene. The polyesters and polyamides may also be derived from dicarboxylic acids and from ethylenically unsaturated diols or diamines, especially from those with relatively long chains of, for example 6 to 20 C atoms. Examples of polyurethanes are those composed of saturated or unsaturated diisocyanates and of unsaturated or, respectively, saturated diols.

Polybutadiene and polyisoprene, and copolymers thereof, are known. Examples of suitable comonomers are olefins, such as ethylene, propene, butene and hexene, (meth)acrylates, acrylonitrile, styrene or vinyl chloride. Polymers with (meth)acrylate groups in the side chain are likewise known. They may, for example, be reaction products of epoxy resins based on novolaks with (meth)acrylic acid, or may be homo- or copolymers of vinyl alcohol or hydroxyalkyl derivatives thereof which are esterified with (meth)acrylic acid, or may be homo- and copolymers of (meth)acrylates which are esterified with hydroxyalkyl (meth)acrylates.

The photopolymerizable compounds can be used alone or in any desired mixtures. It is preferred to use mixtures of polyol (meth)acrylates.

Binders can also be added to the novel compositions, and this is particularly expedient when the photopolymerizable compounds are liquid or viscous substances. The quantity of binder may, for example, be 5–95%, preferably 10–90% and especially 40–90%, by weight relative to the overall solids content. The choice of binder is made depending on the field of application and on properties required for this field, such as the capacity for development in aqueous and organic solvent systems, adhesion to substrates and sensitivity to oxygen.

Examples of suitable binders are polymers having a molecular weight of about 5000 to 2000000, preferably 10000 to 1000000. Examples are: homo- and copolymers of acrylates and methacrylates, for example copolymers of methyl methacrylate/ethyl acrylate/methacrylic acid, poly(alkyl methacrylates), poly(alkyl acrylates); cellulose esters and cellulose ethers, such as cellulose acetate, cellulose acetobutyrate, methylcellulose, ethylcellulose; polyvinylbutyral, polyvinylformal, cyclized rubber, polyethers such as polyethylene oxide, polypropylene oxide and polytetrahydrofuran; polystyrene, polycarbonate, polyurethane, chlorinated polyolefins, polyvinyl chloride, vinyl chloride/vinylidene chloride copolymers, copolymers of vinylidene chloride with acrylonitrile, methyl methacrylate and vinyl acetate, polyvinyl acetate, copoly(ethylene-vinyl acetate), polymers such as polycaprolactam and poly(hexamethyleneadipamide), and polyesters such as poly(ethylene glycol terephthalate) and poly(hexamethylene glycol succinate).

The unsaturated compounds can also be used as a mixture with non-photopolymerizable, film-forming components. These may, for example, be physically drying polymers or solutions thereof in organic solvents, for instance nitrocellulose or cellulose acetobutyrate. They may also, however, be chemically and/or thermally curable (heat-curable) resins, examples being polyisocyanates, polyepoxides and melamine resins. The use of heat-curable resins at the same time is important for use in systems known as hybrid systems, which are photopolymerized in a first stage and then crosslinked by means of thermal aftertreatment in a second stage. The invention additionally provides compositions which in addition to components (a) and (b) comprise at least one electron acceptor (c), for example a dye or a UV absorber. Suitable dyes (c) are described above. Other suitable examples are benzoxanthene, benzothioxanthene, pyronine or porphyrin dyes. Examples of UV absorbers which are suitable as electron acceptor (c) are thioxanthone derivatives, coumarins, benzophenone, benzophenone derivatives or derivatives of hexaarylbisimidazole (HABI). Examples of suitable hexaarylbisimidazole derivatives are described in U.S. Pat. Nos. 3,784,557, 4,252,887, 4,311,783, 4,459,349, 4,410,621 and 4,622,286. Of particular advantage are 2-o-chlorophenyl-substituted derivatives, such as 2,2'-bis(o-chlorophenyl)-4,4',5,5'-tetraphenyl-1,1'-bisimidazole. Other UV absorbers suitable in this context are, for example, polycyclic aromatic hydrocarbons, for example anthracene or pyrene, and the triazines described in EP-A-137 452, in DE-A-27 18 254 and in DE-A-22 43 621. Further suitable triazines can be found in U.S. Pat. No. 4,950,581, column 14, line 60 to column 18, line 44. Of particular advantage are trihalomethyltriazines, for example 2,4-bis(trichloromethyl)-6-(4-styrylphenyl)-s-triazine. Other suitable electron acceptors (c) are benzopteridinediones (described in JP Hei 02 113002), substituted benzophenones (e.g. Michler's ketone, QUANTACURE ABQ, QUANTACURE BPQ and QUANTACURE BTC from International Biosynthetics), trichloromethyltriazine (described in JP Hei 01 033548), metal complexes (described in JP Hei 04 261405), porphyrins (described in JP Hei 06 202548 and JP Hei 06 195014), coumarins and ketocoumarins (described in U.S. Pat No. 4,950,581 and JP Hei 06 175557), p-aminophenyl compounds (described in EP-A 475153), xanthenes (described in JP Hei 06 175566) or pyrylium, thiopyrylium and selenopyrylium dyes (described in JP Hei 06 175563).

As already mentioned above, it is also possible to provide the novel polyborates of the formula I with dye cations, sulphonium- or iodonium cations and to employ them thus as photoinitiator. The invention therefore provides, furthermore, a composition comprising (a) at least one ethylenically unsaturated photopolymerizable compound and (b) at least one polyborate anion of the formula Ia

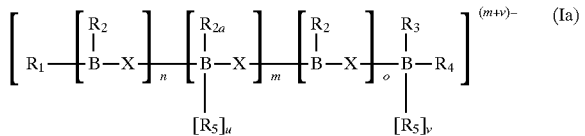

in which the radicals $R_1$, $R_2$, $R_{2a}$, $R_3$, $R_4$, $R_5$ and X, and also n, m, o, u and v, are as defined in claim 1, and (c) a dye cation, sulfonium- or iodonium cation.

Also provided by the invention is a composition as described above comprising, in addition, at least one further borate compound of the formula XI

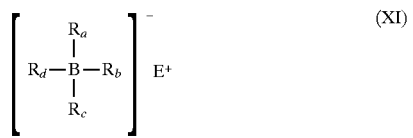

in which $R_a$, $R_b$, $R_c$ and $R_d$ independently of one another are $C_1$–$C_{12}$alkyl, trimethylsilylmethyl, phenyl, another aromatic hydrocarbon, $C_1$–$C_6$alkylphenyl, allyl, phenyl-$C_1$–$C_6$alkyl, $C_2$–$C_8$alkenyl, $C_2$–$C_8$alkynyl, $C_3$–$C_{12}$cycloalkyl or saturated or unsaturated heterocyclic radicals, wherein the radicals phenyl, another aromatic hydrocarbon, phenyl-$C_1$–$C_6$alkyl and saturated or unsaturated heterocyclic radical ar unsubstituted or substituted by unsubstituted or halo-, $OR_6$- and/or $NR_8R_9$-substituted $C_1$–$C_6$alkyl, $OR_6$, $S(O)_pR_7$, $OS(O)_2R_7$, $NR_8R_9$, $C(O)OR_6$, $C(O)NR_8R_9$, $C(O)R_{10}$, $SiR_{11}R_{12}R_{13}$, $BR_{14}R_{15}$, $P(O)_qR_{16}R_{17}$ or halogen;

p is 0, 1 or 2;

q is 0 or 1;

$R_6$ and $R_7$ are unsubstituted or $COOR_{7a}$, OH, $C_1$–$C_{12}$alkoxy- or halo-substituted $C_1$–$C_{12}$alkyl, unsubstituted or mono- to penta-$C_1$–$C_6$alkyl-, -$C_1$–$C_{12}$alkoxy- or -halo-substituted phenyl, or unsubstituted or mono- to penta-$C_1$–$C_6$alkyl-, -$C_1$–$C_{12}$alkoxy- or -halo-substituted phenyl-$C_1$–$C_6$alkyl;

$R_{7a}$ is $C_1$–$C_{12}$alkyl;

$R_8$, $R_9$, $R_{10}$, $R_{11}$, $R_{12}$, $R_{13}$, $R_{14}$ and $R_{15}$ independently of one another are as defined for $R_6$ or are $C_3$–$C_{12}$cycloalkyl, or $R_8$ and $R_9$, together with the N atom to which they are attached, form a 5- or 6-membered ring which may additionally contain O or S atoms, or $R_{14}$ and $R_{15}$, together with the B atom to which they are attached, form a 5- or 6-membered ring;

$R_{16}$ and $R_{17}$ independently of one another are as defined for $R_6$ or are $C_3$–$C_{12}$cycloalkyl; and E is a radical which is able to form positive ions, especially an alkali metal, ammonium, tetraalkylammoinium, sulfonium- or phosphonium radical.

Likewise provided by the invention is a composition comprising (a) at least one ethylenically unsaturated photopolymerizable compound and (b) at least one photoinitiator as described above comprising A) at least one borane of the formula VI and B) at least one electron donor compound. As a further component this composition may comprise an electron aceptor compound.

The novel composition may in addition to the photoinitiator comprising A) and B) also comprise further photoinitiators and/or additives. Specific examples of such photoinitiators are given later on.

The invention provides, moreover, a composition comprising at least one borate of the formula I and at least one dye which changes or loses its colour during or after irradiation, which dye may also, as a cation, be part of the compound of the formula I. Examples of such dyes are cyanine dyes and pyrylium dyes.

In addition to the photoinitiator the photopolymerizable mixtures may include various additives. Examples of these are thermal inhibitors, which are intended to prevent premature polymerization, examples being hydroquinone, hydroquinone derivatives, p-methoxyphenol, β-naphthol or sterically hindered phenols, such as 2,6-di-tert-butyl-p-cresol. In order to increase the stability on storage in the dark it is possible, for example, to use copper compounds, such as copper naphthenate, stearate or octoate, phosphorus compounds, for example triphenylphosphine, tributylphosphine, triethyl phosphite, triphenyl phosphite or tribenzyl phosphite, quaternary ammonium compounds, such as tetramethylammonium chloride or trimethylbenzylammonium chloride, or hydroxylamine derivatives, for example N-diethylhydroxylamine. To exclude atmospheric oxygen during the polymerization it is possible to add paraffin or similar waxlike substances which, being of inadequate solubility in the polymer, migrate to the surface at the beginning of polymerization and form a transparent surface layer which prevents the ingress of air. It is also possible to apply an oxygen-impermeable layer. Light stabilizers which can be added in a small quantity are UV absorbers, for example those of the hydroxyphenylbenzotriazole, hydroxyphenylbenzophenone, oxalamide or hydroxyphenyl-s-triazine type. These compounds can be used individually or in mixtures, with or without sterically hindered amines (HALS). Examples of such UV absorbers and light stabilizers are 1. 2-(2'-hydroxyphenyl)benzotriazoles for example 2-(2'-hydroxy-5'-methylphenyl)-benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl) benzotriazole, 2-(2'-hydroxy-4'-octoxyphenyl) benzotriazole, 2-(3',5'-di-tert amyl-2'-hydroxyphenyl) benzotriazole, 2-(3',5'-bis-(α,α-dimethylbenzyl)-2'-hydroxyphenyl)benzotriazole, mixture of 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyloxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl) phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, and 2-(3'-tert-butyl-2'-hydroxy- 5'-(2-isooctyloxycarbonylethyl) phenylbenzotriazole, 2,2'-methylenebis[4-(1,1,3,3-tetramethylbutyl)-6-benzotriazol-2-yl-phenol]; transesterification product of 2-[340 -tert-butyl-5'-(2-methoxy-carbonylethyl)-2'-hydroxyphenyl]benzotriazole with polyethylene glycol 300; [R -CH$_2$CH$_2$—COO (CH$_2$)$_3$]$_2$- where R=3'-tert-butyl-4'-hydroxy-5'-2H-benzotriazol-2-yl-phenyl.

2. 2-Hydroxybenzophenones, for example the 4-hydroxy-, 4-methoxy-, 4-octoxy-, 4-decyloxy-, 4-dodecyloxy-, 4-benzyloxy-, 4,2',4'-trihydroxy- and 2'-hydroxy-4,4'-dimethoxy derivative.

3. Esters of unsubstituted or substituted benzoic acids, for example 4-tert-butylphenyl salicylate, phenyl salicylate, octylphenyl salicylate, dibenzoylresorcinol, bis(4-tertbutylbenzoyl)resorcinol, benzoylresorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate and 2-methyl-4,6-di-tert-butylphenyl 3,5-di-tert-butyl-4-hydroxybenzoate.

4. Acrylates, for example isooctyl or ethyl α-cyano-β,β-diphenyl acrylate, methyl α-carbomethoxycinnamate, butyl or methyl α-cyano-β-methyl-p-methoxycinnamate, methyl α-carbomethoxy-p-methoxycinnamate and N-(β-carbomethoxy-β-cyanovinyl)-2-methylindoline.

5. Sterically hindered amines, for example bis-(2,2,6,6-tetramethylpiperidyl) sebacate, bis-(2,2,6,6-tetramethylpiperidyl) succinate, bis-(1,2,2,6,6-pentamethylpiperidyl) sebacate, bis(1,2,2,6,6-pentamethylpiperidyl) n-butyl-3,5-di-tert-butyl-4-hydroxybenzylmalonate, condensation product of 1-hydroxyethyl-2,2,6,6-tetramethyl-4-hydroxypiperidine and succinic acid, condensation product of N,N'-bis-(2,2,6,6-tetramethyl-4-piperidyl)hexamethylene-diamine and 4-tert-octylamino-2,6-dichloro-1,3,5-s-triazine, tris-(2,2,6,6-tetramethyl-4-piperidyl) nitrilotriacetate, tetrakis-(2,2,6,6-tetramethyl-4-piperidyl)-1,2,3,4-butane tetraoate, 1,1'-(1,2-ethandiyl)bis(3,3,5,5-tetramethyl-piperazinone), 4-benzoyl-2,2,6,6-tetramethylpiperidine, 4-stearyloxy-2,2,6,6-tetramethylpiperidine, bis-(1,2,2,6,6-pentamethylpiperidyl) 2-n-butyl-2-(2-hydroxy-3,5-di-tert-butylbenzyl)malonate, 3-n-octyl-7,7,9,9-tetramethyl-1,3,8-triazaspiro[4.5]decane-2,4-dione, bis-(1-octyloxy-2,2,6,6-tetramethylpiperidyl) sebacate, bis-(1-octyloxy-2,2,6,6-tetramethylpiperidyl) succinate, condensation product of N,N'-bis-(2,2,6,6-tetramethyl-4-piperidyl)hexamethylenediamine and 4-morpholino-2,6-dichloro-1,3,5-triazine, condensation product of 2-chloro-4,6-di-(4-n-butylamino-2,2,6,6-tetramethylpiperidyl)-1,3,5-triazine and 1,2-bis-(3-aminopropylamino)ethane, condensation product of 2-chloro-4,6-di-(4-n-butylamino-1,2,2,6,6-pentamethylpiperidyl)-1,3,5-triazine and 1,2-bis-(3-aminopropylamino)ethane, 8-acetyl-3dodecyl-7,7,9,9-tetramethyl-1,3,8-triazaspiro[4,5]decane-2,4-dione, 3-dodecyl-1-(2,2,6,6-tetramethyl-4-piperidyl)pyrrolidine-2,5-dione and 3-dodecyl-1-(1,2,2,6,6-penta-methyl-4-piperidyl)-pyrrolidine-2,5-dione.

6. Oxalamides, for example 4,4'-dioctyloxyoxanilide, 2,2'-diethoxyoxanilide, 2,2'-dioctyloxy-5,5'-di-tert-butyloxanilide, 2,2'-didodecyloxy-5,5'-di-tert-butyloxanilide, 2-ethoxy-2'-ethyloxanilide, N,N'-bis-(3-dimethylaminopropyl)oxalamide, 2-ethoxy-5-tert-butyl-2'-ethyloxanilide and its mixture with 2-ethoxy-2'-ethyl-5,4'-di-tert-butyloxanilide, mixtures of o- and p-methoxy- and of o- and p-ethoxy-disubstituted oxanalides.

7. 2-(2-Hydroxyohenyl)-1,3,5-triazines, for example 2,4, 6-tris(2-hydroxy-4-octyloxyphenyl) -1,3,5-triazine, 2-(2-hydroxy-4-octyloxyphenyl)-4,6-bis(2,4-dimethylphenyl)-1, 3,5-triazine, 2-(2,4-dihydroxyphenyl)-4,6-bis(2,4-dimethylphenyl)-1,3,5-triazine, 2,4-bis(2-hydroxy-4-propyloxy-phenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2-hydroxy-3-butyloxy-propyloxy)phenyl]-4,6-bis(2,4-dimethylphenyl)-1,3,5-triazine, 2-[2-hydroxy-4-(2-hydroxy-3-octyloxy-propyloxy)phenyl]-4,6-bis(2,4-dimethylphenyl)-1,3,5-triazine, 2-[4-dodecyl/tridecyl-oxy-(2-hydroxypropyl)oxy-2-hydroxyphenyl]-4,6-bis(2,4-dimethylphenyl)-1,3,5-triazine.

8. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythrityl diphosphite, tris(2,4-di-tert-butylphenyl) phosphite, diisodecyl pentaerythrityl diphosphite, bis(2,4-di-tert-butylphenyl) pentaerythrityl diphosphite, bis(2,6-di-tert-butyl-4-methylphenyl) pentaerythrityl diphosphite, bis-isodecyloxy pentaerythrityl diphosphite, bis(2,4-di-tert-butyl-6-methylphenyl) pentaerythrityl diphosphite, bis(2,4,6-tri-tert-butylphenyl) pentaerythrityl diphosphite, tristearyl sorbityl triphosphite, tetrakis(2,4-di-tert-butylphenyl)-4,4'-biphenylenediphosphonite, 6-isooctyloxy-2,4,8,10-tetra-tert-butyl-12H-dibenzo[d,g]-1,3,2-dioxaphosphocine, 6-fluoro-2,4,8,10-tetra-tert-butyl-12-methyl-dibenzo[d,g]-1, 3,2-dioxaphosphocine, bis(2,4-di-tert-butyl-6-methylphenyl) methyl phosphite and bis(2,4-di-tert-butyl-6-methylphenyl) ethyl phosphite.

To accelerate the photopolymerization it is possible to add amines, for example triethanolamine, N-methyldiethanolamine, p-dimethylaminobenzoate or Michler's ketone. The action of the amines can be intensified by the addition of aromatic ketones of the benzophenone type. Examples of amines which can be used as oxygen scavengers are substituted N,N-dialkylanilines, as are described in EP-A-339 841. Other accelerators, coinitiators and autoxidizers are, for example, thiols, thioethers, disulfides and phosphines, as described, for example, in EP-A-438 123 and GB-A-2 180 358.

The curing process can be assisted, in particular, by compositions which are pigmented (for example with titanium dioxide), and also by adding a component which under thermal conditions forms free radicals, for example an azo compound such as 2,2'-azobis-(4-methoxy-2,4-dimethylvaleronitrile), a triazene, diazo sulfide, pentazadiene or a peroxy compound, for instance a hydroperoxide or peroxycarbonate, for example t-butyl hydroperoxide, as described for example in EP-A-245 639.

Further customary additives, depending on the intended use, are fluorescent whiteners, fillers, pigments, dyes, wetting agents and levelling assistants. In order to cure thick and pigmented coatings it is appropriate to add glass microspheres or pulverized glass fibres, as described for example in U.S. Pat. No. 5,013,768.

The invention also provides compositions comprising as component (a) at least one ethylenically unsaturated photopolymerizable compound which is emulsified or dissolved in water.

Many variants of such radiation-curable aqueous prepolymer dispersions are commercially available. A prepolymer dispersion is understood as being a dispersion of water and at least one prepolymer dispersed therein. The concentration of water in these systems is, for example, from 5 to 80% by weight, in particular from 30 to 60% by weight. The concentration of the radiation-curable prepolymer or prepolymer mixture is, for example, from 95 to 20% by weight, in particular from 70 to 40% by weight. In these compositions the sum of the percentages given for water and prepolymer is in each case 100, with auxiliaries and additives being added in varying quantities depending on the intended use.

The radiation-curable, film-forming prepolymers which are dispersed in water and are often also dissolved are mono- or polyfunctional, ethylenically unsaturated prepolymers which are known per se for aqueous prepolymer dispersions, can be initiated by free radicals and have a content of, for example, from 0.01 to 1.0 mol of polymerizable double bonds per 100 g of prepolymer and an average molecular weight of, for example, at least 400, in particular from 500 to 10 000. Prepolymers with higher molecular weights, however, may also be considered depending on the intended application. Use is made, for example, of polyesters containing polymerizable C—C double bonds and having an acid number of not more than 10, of polyethers containing polymerizable C—C double bonds, of hydroxyl-containing reaction products of a polyepoxide, containing at least two epoxide groups per molecule, with at least one $\alpha,\beta$-ethylenically unsaturated carboxylic acid, of polyurethane (meth)acrylates and of acrylic copolymers which contain $\alpha,\beta$-ethylenically unsaturated acrylic radicals, as are described in EP-A-12 339. Mixtures of these prepolymers can likewise be used. Also suitable are the polymerizable prepolymers described in EP-A-33 896, which are thioether adducts of polymerizable prepolymers having an average molecular weight of at least 600, a carboxyl group content of from 0.2 to 15% and a content of from 0.01 to 0.8 mol of polymerizable C—C double bonds per 100 g of prepolymer. Other suitable aqueous dispersions, based on specific alkyl (meth)acrylate polymers, are described in EP-A-41 125, and suitable water-dispersible, radiation-curable prepolymers of urethane acrylates can be found in DE-A-29 36 039. Further additives which may be included in these radiation-curable aqueous prepolymer dispersions are dispersion auxiliaries, emulsifiers, antioxidants, light stabilizers, dyes, pigments, fillers, for example talc, gypsum, silicic acid, rutile, carbon black, zinc oxide, iron oxides, reaction accelerators, levelling agents, lubricants, wetting agents, thickeners, matting agents, antifoams and other auxiliaries customary in paint technology. Suitable dispersion auxiliaries are water-soluble organic compounds which are of high molecular mass and contain polar groups, examples being polyvinyl alcohols, polyvinylpyrrolidone and cellulose ethers. Emulsifiers which can be used are nonionic emulsifiers and, if desired, ionic emulsifiers as well.

The quantity of photoinitiator (b) in the photopolymerizable compositions is expediently from 0.05 to 15% by weight, preferably from 0.1 to 5% by weight, based on the composition.

In certain cases it may be of advantage to use mixtures of two or more of the novel photoinitiators. As already mentioned above, it is of course also possible to use mixtures with other known photoinitiators, for example mixtures with benzophenone, benzophenone derivatives, acetophenone, acetophenone derivatives, for example cc-hydroxycycloalkyl phenyl ketones, dialkoxyacetophenones, $\alpha$-hydroxy- or $\alpha$-aminoacetophenones, 4-aroyl-1,3-dioxolanes, benzoin alkyl ethers and benzil ketals, monoacyl phosphine oxides, bisacylphosphine oxides, titanocenes or ferrocenes. Examples of particularly suitable photoinitiators are: 1-(4-dodecylbenzoyl)-1-hydroxy-1-methylethane, 1-(4-isopropylbenzoyl)-1-hydroxy-1-methylethane, 1-benzoyl-1-hydroxy-1-methylethane, 1-[4-(2-hydroxyethoxy)benzoyl]-1-hydroxy-1-methylethane, 1-[4-(acryloyloxyethoxy)benzoyl]-1-hydroxy-1-methylethane, diphenyl ketone, phenyl 1-hydroxy-cyclohexyl ketone, (4-morpholinobenzoyl)-1-benzyl-1-dimethylaminopropane, 1-(3,4-di-methoxyphenyl)-2-benzyl-2-dimethylamino-butan-1-one, (4-methylthiobenzoyl)-1-methyl-1-morpholinoethane, benzil dimethyl ketal, bis (cyclopentadienyl)bis(2,6-difluoro-3-pyrrylphenyl)titanium, cyclopentadienyl-arene-iron(II) complex salts, for example ($\eta^6$-iso-propylbenzene)($\eta^5$-cyclopentadienyl)iron(II) hexafluorophosphate, trimethylbenzoyidiphenylphosphine oxide , bis(2,6-dimethoxybenzoyl)-(2,4,4-trimethylpentyl) phosphine oxide, bis(2,4,6-trimethylbenzoyl)-2,4-dipentoxyphenylphosphine oxide or bis(2,4,6-trimethylbenzoyl)phenyl-phosphine oxide. Other suitable additional photoinitiators can be found in U.S. Pat. No. 4,950,581 column 20, line 35 to column 21, line 35. Also suitable are triazine compounds, for example the triazines described in EP-A-137 452, in DE-A-27 18 254 and in DE-A-22 43 621. Further suitable triazines can be found in U.S. Pat. No. 4,950,581, column 14, line 60 to column 18, line 44. There is particular interest in trihalomethyltriazines, for example 2,4-bis(trichloromethyl)-6-(4-styrylphenyl)-s-triazine. Where the novel photoinitiators are employed in hybrid systems, use is made, in addition to the novel free-radical hardeners, of cationic photoinitiators, for example peroxide compounds, such as benzoyl peroxide (other suitable peroxides are described in U.S. Pat. No. 4,950,581 column 19, lines 17–25), aromatic sulfonium, phosphonium or iodonium salts (as described for example in U.S. Pat. No. 4,950,581, column 18, line 60 to column 19, line 10) or cyclopentadienyl-arene-iron(II) complex salts, for example ($\eta^6$-isopropylbenzene)-($\eta^5$-cyclopentadien-yl) iron(II) hexafluorophosphate.

The invention therefore further provides compositions which in addition to the photoinitiator (b) also comprise at least one further photoinitiator (d) and/or other additives.

Compositions comprising as additional photoinitiator (d) a titanocene, a ferrocene, a benzophenone, a benzoin alkyl ether, a benzil ketal, a 4-aroyl-1,3-dioxolane, a dialkoxyacetophenone, an α-hydroxy- or α-aminoacetophenone, an α-hydroxycycloalkyl phenyl ketone, a xanthone, a thioxanthone, an anthraquinone or a mono- or bisacylphosphine oxide, or mixtures thereof, as additional photoinitiator are of particular interest.

Also of interest are compositions in which a further additive used is a readily reducible compound, especially a halogenated hydrocarbon. Suitable readily reducible compounds are, for example, halogenated hydrocarbons such as, in particular,

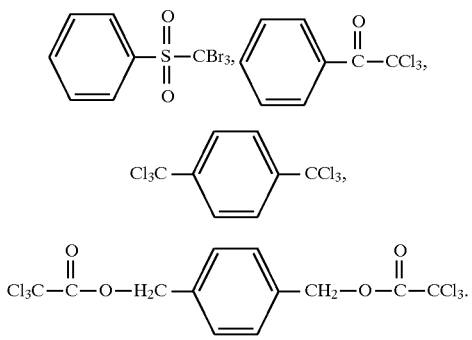

The term readily reducible compound is to be understood in this context as including compounds as described in U.S. Pat. No. 4,950, 581, examples including iodonium salts, sulfonium salts, organic peroxides, compounds having carbon-halide bonds (trichloromethyltriazines), heterocyclic sulfur compounds, and other photoinitiators (α-amino ketones). Examples of other additives are heterocycles as described in the Patents and Patent Applications U.S. Pat. No. 5,168,032, JP 02 244050, JP 02 054268, JP 01 017048 and DE 383308. Examples of further additives are aromatic imines, described in U.S. Pat. No. 5,079,126, and aromatic diazo compounds described in U.S. Pat. No. 5,200,292 (e.g. iminoquinone diazides), thiols, described in U.S. Pat. No. 4,937,159 and thiols ,and N,N-dialkylanilines, described in U.S. Pat. No. 4,874,685. It is also possible to employ two or more of the stated coinitiators or electron acceptors and additives in combination.

The photopolymerizable compositions can be used for various purposes, for example as printing ink, as a clear finish, as a white finish, for example for wood or metal, as a coating material, inter alia for paper, wood, metal or plastic, as a powder coating, as a daylight-curable coating for roadmarking and the marking of buildings, for photographic reproduction techniques, for holographic recording materials, for image recording techniques or for producing printing plates which can be developed with organic solvents or with aqueous alkalis, for producing masks for screen printing, as dental filling compositions, as adhesives, including pressure-sensitive adhesives, as laminating resins, as etch resists or permanent resists, and as solder masks for electronic circuits, for producing three-dimensional articles by mass curing (UV curing in transparent moulds) or by the stereolithography technique, as is described, for example, in U.S. Pat. No. 4,575,330, for producing composite materials (for example styrenic polyesters, which may if desired contain glass fibres and/or other fibres and other auxiliaries) and other thick-layered compositions, for coating or sealing electronic components, or as coatings for optical fibres.

The novel compounds may additionally be employed as initiators for emulsion, bead or suspension polymerizations, as polymerization initiators for fixing ordered states of liquid-crystalline monomers and oligomers, or as initiators for fixing dyes on organic materials.

In coating materials, use is frequently made of mixtures of a prepolymer with polyunsaturated monomers, which may additionally include a monounsaturated monomer as well. It is the prepolymer here which primarily dictates the properties of the coating film, and by varying it the skilled worker is able to influence the properties of the cured film. The polyunsaturated monomer functions as a crosslinking agent which renders the film insoluble. The monounsaturated monomer functions as a reactive diluent, which is used to reduce the viscosity without the need to employ a solvent.

Unsaturated polyester resins are usually used in two-component (two-pack) systems together with a monounsaturated monomer, preferably with styrene. For photoresists, specific one-component Systems are often used, for example polymaleimides, polychalcones or polyimicles, as described in DE-A-23 08 830.

The novel compounds and mixtures thereof can also be used as free-radical photoinitiators or photoinitiating systems for radiation-curable powder coatings. The powder coatings can be based on solid resins and monomers containing reactive double bonds, for example maleates, vinyl ethers, aceryates, acrylamides and mixtures thereof. A free-radically UV-curable powder coating can be formulated by mixing unsaturated polyester resins with solid acrylamides (for example methyl methylacrylamidoglycolate) and a novel free-radical photoinitiator, such formulations being as described, for example, in the paper "Radiation Curing of Powder Coatino", Conference Proceedings, Radtech Europe 1993 by M. Wittig and Th. Gohmann. Free-radically UV-curable powder coatings can also be formulated by mixing unsaturated polyester resins with solid acrylates, methacrylates or vinyl ethers and with a novel photoinitiator (or photoinitiator mixture). The powder coatings may also comprise binders as are described, for example, in DE-A-42 28 514 and in EP-A-636 669.

The UV-curable powder coatings may additionally comprise white or coloured pigments. For example, preferably rutiletitanium dioxide can be employed in concentrations of up to 50% by weight in order to give a cured powder coating of good hiding power. The procedure normally comprises electrostatic or tribostatic spraying of the powder onto the substrate, for example metal or wood, melting of the powder by heating, and, after a smooth film has formed, radiation-curing of the coating with ultraviolet and/or visible light, using for example medium-pressure mercury lamps, metal halide lamps or xenon lamps. A particular advantage of the radiation-curable powder coatings over their heat-curable counterparts is that the flow time after melting of the powder particles can be delayed if desired in order to ensure the formation of a smooth, high-gloss coating. In contrast to heat-curable systems, radiation-curable powder coatings can be formulated to melt at lower temperatures without the unwanted effect of shortening their lifetime. For this reason, they are also suitable as coatings for heat-sensitive substrates, for example wood or plastics. In addition to the novel photoinitiators, the powder coating formulations may also include UV absorbers. Appropriate examples are listed above in sections 1–8.

The novel photocurable compositions are suitable, for example, as coating materials for substrates of all kinds, for example wood, textiles, paper, ceramic, glass, plastics such as polyesters, polyethylene torephthalate, polyolefins or cellulose acetate, especially in the form of films, and also metals such as Al, Cu, Ni, Fe, Zn, Mg or Co and GaAs, Si or $SiO_2$ to which it is intended to apply a protective layer or, by means of imagewise exposure, to generate a reproduced image.

Coating of the substrates can be carried out by applying to the substrate a liquid composition, a solution or a suspension. The choice of solvents and the concentration depend principally on the type of composition and on the coating technique. The solvent should be inert, i.e. it should not undergo a chemical reaction with the components and should be able to be removed again, after coating, in the course of drying. Examples of suitable solvents are ketones, ethers and esters, such as methyl ethyl ketone, isobutyl methyl ketone, cyclopentanone, cyclohexanone, N-methylpyrrolidone, dioxane, tetrahydrofuran, 2-methoxyethanol, 2-ethoxyethanol, 1-methoxy-2-propanol, 1,2-dimethoxyethane, ethyl acetate, n-butyl acetate and ethyl 3-ethoxypropionate. The solution is applied uniformly to a substrate by means of known coating techniques, for example by spin coating, dip coating, knife coating, curtain coating, brushing, spraying, especially by electrostatic spraying, and reverse-roll coating, and also by means of electrophoretic deposition. It is also possible to apply the photosensitive layer to a temporary, flexible support and then to coat the final substrate, for example a copper-clad circuit board, by transferring the layer via lamination.

The quantity applied (coat thickness) and the nature of the substrate (layer support) are dependent on the desired field of application. The range of coat thicknesses generally comprises values from about 0.1 $\mu$m to more than 100 $\mu$m.

The novel radiation-sensitive compositions find application as negative resists, having a very high sensitivity to light and being able to be developed in an aqueous alkaline medium without swelling. They are suitable as photoresists for electronics (electroplating resist, etch resist, solder resist), the production of printing plates, such as offset, flexographic and relief printing plates or screen printing and/or the production of dies, for use in chemical milling or as a microresist in the production of integrated circuits. The possible layer supports, and the processing conditions of the coated substrates, are just as varied.

The compounds according to the invention also find application for the production of one- or more-layered materials for the image recording ore image reproduction (copies, reprography), which may be uni- or polychromatic. Furthermore the materials are suitable for colour proofing systems. In this technology formulations containing microcapsules can be applied and for the image production the radiation curing can be followed by a thermal treatment. Such systems and technologies and their applications are for example disclosed in U.S. Pat. No. 5,376,459.

Substrates used for photographic information recording include, for example, films of polyester, cellulose acetate or polymer-coated papers; substrates for offset printing formes are specially treated aluminum, substrates for producing printed circuits are copper-clad laminates, and substrates for producing integrated circuits are silicon wafers. The layer thicknesses for photographic materials and offset printing forms are generally from about 0.5 $\mu$m to 10 $\mu$m, while for printed circuits they are from 1.0 $\mu$m to about 100 $\mu$m.

Following the coating of the substrates, the solvent is removed, generally by drying, to leave a coat of the photoresist on the substrate. The term "imagewise" exposure includes both exposure through a photomask comprising a predetermined pattern, for example a slide, exposure by means of a laser beam, which for example is moved under computer control over the surface of the coated substrate and in this way produces an image, and irradiation with computer-controlled electron beams.

Following the imagewise exposure of the material and prior to development, it may be advantageous to carry out thermal treatment for a short time. In this case only the exposed sections are thermally cured. The temperatures employed are generally 50°–1500° C., preferably 8°–130° C.; the period of thermal treatment is in general between 0.25 and 10 minutes.

The photocurable composition may additionally be used in a process for producing printing plates or photoresists as is described, for example, in DE-A-40 13 358. In such a process the composition is exposed for a short time to visible light with a wavelength of at least 400 nm, without a mask, prior to, simultaneously with or following imagewise irradiation.

After the exposure and, if implemented, thermal treatment, the unexposed areas of the photosensitive coating are removed with a developer in a manner known per se.

As already mentioned, the novel compositions can be developed by aqueous alkalis. Particularly suitable aqueous-alkaline developer solutions are aqueous solutions of tetraalkylammonium hydroxides or of alkali metal silicates, phosphates, hydroxides and carbonates. Minor quantities of wetting agents and/or organic solvents may also be added, if desired, to these solutions. Examples of typical organic solvents, which may be added to the developer liquids in small quantities, are cyclohexanone, 2-ethoxyethanol, toluene, acetone and mixtures of such solvents.

Photocuring is of great importance for printing inks, since the drying time of the binder is a critical factor for the production rate of graphic products, and should be in the order of fractions of seconds. UV-curable inks are particularly important for screen printing.

As already mentioned above, the novel mixtures are also highly suitable for producing printing plates. This application uses, for example, mixtures of soluble linear polyamides or styrene/butadiene and/or styrene/isoprene rubber, polyacrylates or polymethyl methacrylates containing carboxyl groups, polyvinyl alcohols or urethane acrylates with photopolymerizable monomers, for example acrylamides and/or methacrylamides, or acrylates and/or methacrylates, and a photoinitiator. Films and plates of these systems (wet or dry) are exposed over the negative (or positive) of the printed original, and the uncured parts are subsequently washed out using an appropriate solvent.

Another field where photocuring is employed is the coating of metals, in the case, for example, of the coating o metal plates and tubes, cans or bottle caps, and photocuring of polymer coatings, for example of floor or wall coverings based on PVC.

Examples of the photocuring of paper coatings are the colorless varnishing of labels, record sleeves and book covers.

Also of interest is the use of the novel compounds for curing shaped articles made from composite compositions. The composite composition consists of a self-supporting matrix material, for example a glass fibre fabric, or alternatively, for example, plant fibres [cf. K.-P. Mieck, T. Reussmann in Kunststoffe 85 (1995), 366–370], which is impregnated with the photocuring formulation. Shaped parts comprising composite compositions, when produced using the novel compounds, attain a high level of mechanical stability and resistance. The novel compounds can also be employed as photocuring agents in moulding, impregnating and coating composition s as are described, for example, in EP-A-7086. Examples of such compositions are gel coat resins, which are subject to stringent requirements regarding curing activity and yellowing resistance, and fibre-reinforced mouldings, such as, for example, light diffusing panels which are planar or have lengthwise or crosswise corrugation. Techniques for producing such mouldings, such as hand lay-up, spray lay-up, centrifugal casting or filament winding, are described, for example, by P. H. Selden in "Glasfaserverstärkte Kunststoffe", page 610, Springer Verlag Berlin-Heidelberg-New York 1967. Examples of articles which can be produced by these techniques are boats, fibre board or chipboard panels with a double-sided coating of glass fibre-reinforced plastic, pipes, containers, etc. Further examples of moulding, impregnating and coating compositions are UP resin gel coats for mouldings containing glass fibres (GRP), such as corrugated sheets and paper laminates. Paper laminates may be based on urea resins or melamine resins. Prior to production of the laminate, the gel coat is produced on a support (for example a film). The novel photocurable compositions can also be used for casting resins or for embedding articles, for example electronic components, etc. They can additionally be employed for lining cavities and pipes. Curing is carried out using medium-pressure mercury lamps as are conventional in UV curing. However, there is also particular interest in less intense lamps, for example of the type TL 40W/03 or TL40W/05. The intensity of these lamps corresponds approximately to that of sunlight. It is also possible to use direct sunlight for curing. A further advantage is that the composite composition can be removed from the light source in a partly cured, plastic state and can be shaped, with full curing taking place subsequently.

The compositions and compounds according to the invention can be used for the production of waveguide and optical switches wherein advantage is taken of the development of a difference in the index of refraction between irradiated and unirradiated areas.

The use of photocurable compositions for imaging techniques and for the optical production of information carriers is also important. In such applications, as already described above, the layer (wet or dry) applied to the support is irradiated through a photomask with UV or visible light, and the unexposed areas of the layer are removed by treatment with a solvent (=developer). Application of the photocurable layer to metal can also be carried out by electrodeposition. The exposed areas are polymeric through crosslinking and are therefore insoluble and remain on the support. Appropriate colouration produces visible images. Where the support is a metallized layer, the metal can, following exposure and development, be etched away at the unexposed areas or reinforced by electroplating. In this way it is possible to produce printed electronic circuits and photoresists.

The photosensitivity of the novel compositions extends in general from about 200 nm through the UV region into the infrared region (about 20 000 nm, in particular 1200 nm) and therefore spans a very broad range. Suitable radiation is present, for example, in sunlight or light from artificial light sources. Consequently, a large number of very different types of light source are employed. Both point sources and arrays ("lamp carpets") are suitable. Examples are carbon arc lamps, xenon arc lamps, medium-, high- and low-pressure mercury lamps, possibly doped with metal halide (metal-halogen lamps), microwave-excited metal vapour lamps, excimer lamps, superactinic fluorescent tubes, fluorescent lamps, argon incandescent lamps, electronic flashlamps, photographic floodlamps, electron beams and X-rays, produced by means of synchrotrons or laser plasma. The distance between the lamp and the substrate to be exposed in accordance with the invention may vary depending on the intended application and the type and output of the lamp, and may be, for example, from 2 cm to 150 cm. Laser light sources, for example excimer lasers, are especially suitable. Lasers in the visible region or in the IR region can also be employed. In this case, the high sensitivity of the novel materials and the possibility of adapting the dye to the laser line are very advantageous. By this method it is possible to produce printed circuits in the electronics industry, lithographic offset printing plates or relief printing plates, and also photographic image-recording materials.

The invention additionally provides for the use of the above-described composition for preparing pigmented and unpigmented paints and varnishes, printing inks, powder coatings, printing plates, adhesives, dental compositions, waveguides, optical switches, colour proofing systems, composite compositions, glass fibre cable coatings, screen printing stencils, resist materials, for photographic reproductions, for encapsulating electrical and electronic components, for producing magnetic recording materials, for producing three-dimensional objects by stereolithography, and as image recording material, especially for holographic recordings.

The invention additionally provides a coated substrate which is coated on at least one surface with a composition as described above, and describes a process for the photographic production of relief images, in which a coated substrate is subjected to imagewise exposure and then the unexposed portions are removed with a solvent. Of particular advantage in this context is the laser beam exposure already mentioned above.

The invention also provides a process for the photopolymerization of nonvolatile monomeric, oligomeric or polymeric compounds containing at least one ethylenically unsaturated double bond, which comprises adding at least one compound of the formula I or a photoinitiator as described above to said compounds and irradiating the resulting composition with light having a wavelength ranging from 200 nm up to and including the infrared region.

The novel borate compounds can be employed not only as initiators for photopolymerization reactions but also as thermal polymerization initiators.

Consequently, the invention also provides for the use of the compounds of formula I as initiators for the thermal polymerization of compounds containing ethylenically unsaturated double bonds, and a process for the thermal polymerization of compounds containing ethylenically unsaturated double bonds, which comprises employing at least one compound of the formula I as polymerization initiator.

The examples which follow illustrate the invention in more detail. Parts and percentages are, as in the remainder of the description and in the claims, by weight, unless stated otherwise. Where alkyl radicals having more than three carbon atoms are referred to without any mention of specific isomers, the n-isomers are meant in each case.

I. Preparation of the Boranes

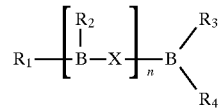

EXAMPLE 1

1,4-Bis(dimesitylboryl)benzene $R_1$–$R_4$=mesityl, n=1; X=1,4-phenylene

Method A

One equivalent of butyllithium (0.01 mol) in hexane is added over the course of 15 minutes at −78° C. to a solution of 2.36 g (0.01 mol) of 1,4-dibromobenzene in 10 ml of diethyl ether. The temperature is slowly raised to −50° C. over the course of one hour, and the mixture is then cooled again to −78° C. Subsequently, 2.68 g (0.01 mol) of solid dimesitylfluoroborane are added, and the mixture is allowed to warm up to room temperature and is stirred for an hour. The mixture is poured into 50 ml of water and filtered to give 3.1 g of a beige solid. The product is purified by washing with boiling acetonitrile, giving 2.1 g (52% of theory) of 1-bromo-4-dimesitylborylbenzene. A solution of this borane in 20 ml of tetrahydrofuran (THF) is cooled to −78° C. and treated with 1 equivalent (0.05 mol) of butyllithium in hexane. The red solution is allowed to warm up to −50° C. over the course of 30 minutes and is then cooled again to −78° C. Subsequently, 1.34 g (0.005 mol) of solid dimesitylfluoroborane are added, and the reaction mixture is allowed to warm up to room temperature and is stirred for an hour. The mixture Is poured into 50 ml of water and filtered to give a white solid. The product is purified by washing with boiling acetonitrile, giving 2.23 g (78% of theory) of the pure bisborane. Physical data are given in Table 1.

Method B

One equivalent (0.01 mol) of butyllithium in hexane is added over the course of 15 minutes at −78° C. to a solution of 2.36 g (0.01 mol) of 1,4-dibromobenzene in 20 ml of THF. The suspension is allowed to warm slowly up to 50° C. over the course of 30 minutes, and is then cooled again to −78° C. and treated with 2.68 g of (0.01 mol) of solid dimesitylfluoroborane. The reaction mixture is allowed to warm up to room temperature and is stirred for half an hour. The mixture is cooled to −78° C. and treated as described above in Method A in succession with butyllithiuim and dimesitylfluoroborane. After warming to room temperature, the mixture is poured into 100 ml of water and filtered and the product is washed with boiling acetonitrile to give 4.88 g (85% of theory) of the product.

Method C 2 equivalents of butyllithium (0.1 mol) in hexane are added at room temperature to a solution of 11.8 g (0.05 mol) of 1,4-dibromobenzene in 200 ml of hexane. The mixture is refluxed for 3 hours. The suspension which formed is cooled to −78° C. and treated with 26.8 g (0.1 mol) of solid dimesitylfluoroborane. After warming to room temperature, the reaction mixture is poured into 200 ml of water and subjected twice to extraction with 50 ml of hexane. The combined organic phases are dried over magnesium sulphate, filtered and concentrated, resulting in a yellow solid. Recrystallization from hexane gives 17.0 g (i.e. 59% of theory) of 1,4-bis(dimesitylboryl)benzene.

Method D 2 equivalents (0.08 mol) of t-butyllithium in pentane are added over the course of one hour at 0° C. to a solution of 8 g (0.04 mol) of bromomesitylene in 100 ml of hexane. The mixture is refluxed for 3 hours. After cooling to 0° C., a solution of 4.17 g (0.01 mol) of 1,4-bis(dibromoboryl) benzene in 80 ml of hexan is added to the mixture and the batch is refluxed overnight. The thick suspension produced is poured into 200 ml of water and subjected twice to extraction with 50 ml of hexane. The combined organic phases are dried over magnesium sulphate, filtered and concentrated. A yellow solid is formed which is recrystallized from hexane, giving 3.0 g (52% of theory) of 1,4-bis (dimesitylboryl)benzene.

Method E 1,4-Bis(dimesitylboryl)benzene can also be obtained by the method described by A. Schultz and W. Kaim in Chem. Ber. 1989, 122, 1863–1868, by reacting one equivalent of 1,4-bis(bromomagnesio)benzene with 2 equivalents of dimesitylfluoroborane under reflux in THF, in a yield of 6% of theory.

EXAMPLE 2

1-Dimesitylboryl-4-diphenylborylbenzene $R_1,R_2$=mesityl; $R_3,R_4$=phenyl; n=1; X=1,4-phenylene The compound is prepared in accordance with Method B described above, using 1 equivalent of dimesitylfluoroborane and 1 equivalent of diphenylisopropoxyborane. The crude product is obtained by concentrating the reaction mixture under a high vacuum and treating the solid residue, under argon, with hexane. Filtration, concentration of the filtrate and recrystallization of the residue from acetonitrile give 3.0 g (61% of theory) of the pale yellow title product, which is sensitive to air. Physical data are given in Tabelle 1.

EXAMPLE 3

1-Bis(chloromesityl)boryl-4-dimesitylborylbenzene $R_1,R_2$=mesityl; $R_3,R_4$=chloromesityl; n=1; X=1,4-phenylene The compound is prepared in accordance with Method B described above, using 1 equivalent of bis(chloromesityl) fluoroborane and 1 equivalent of dimesitylfluoroborane. Physical data are given in Table 1.

EXAMPLE 4

1,4-Bis[bis(chloromesityl)boryl]benzene $R_1$–$R_4$=chloromesityl; n=1; X=1,4-phenylene The compound is prepared by Method B described above using 2 equivalents of bis(chloromesityl)fluoroborane. Physical data are given in Table 1.

EXAMPLE 5

1,3-Bis(dimesitylboryl)benzene $R_1$–$R_4$=mesityl; n=1; X=1,3-phenylene

The compound is prepared by Method B described above and obtained in a yield of 83%. Physical data are given in Table 1.

EXAMPLE 5

1-Fluoro-3,5-bis(dimesitylboryl)benzene $R_1$–$R_4$=mesityl; n=1; X=5-fluoro-1,3-phenylene The compound is prepared by Method C described above in diethyl ether at −50° C. and obtained in a yield of 61%. Physical data are given in Table 1.

EXAMPLE 7

1-Bis(chloromesityl)boryl-3-dimesitylborylbenzene $R_1,R_2$=mesityl; $R_3,R_4$=chloromesityl; n=1; X=1,3-phenylene The compound is prepared by Method B described above in a yield of 86%, using 1 equivalent of bis(chloromesityl)

fluoroborane and 1 equivalent of dimesitylfluoroborane. Physical data are given in Table 1.

EXAMPLE 8

4,4'-Bis(dimesitylboryl)biphenyl $R_1$–$R_4$=mesityl; n=1; X=4,4'-biphenylene

The compound is obtained by Method C described above in diethyl ether at 0° C. in a yield of 70%. Physical data are given in Table 1.

EXAMPLE 9

4-Bis(chloromesityl)boryl-4'-dimesitylborylbiphenyl $R_1$, $R_2$=mesityl; $R_3$,$R_4$=chloromesityl; n=1; X=4,4'-biphenylene The compound is obtained by Method B described above in a yield of 71%, using 1 equivalent of bis(chloromesityl)fluoroborane and 1 equivalent of dimesitylfluoroborane. Physical data are given in Table 1.

EXAMPLE 10

4,4'-Bis(dimesitylboryl)benzophenone ethylene ketal $R_1$–$R_4$=Mesityl; n=1; X=

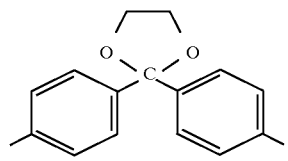

The compound is prepared by Method C described above in diethyl ether at 0° C. Physical data are given in Table 1.

EXAMPLE 11

4,4'-Bis(dimesitylboryl)benzophenone $R_1$–$R_4$=mesityl; n=1; X=

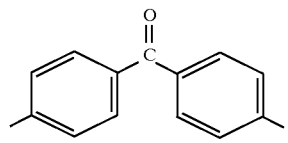

The compound is obtained in a yield of 64% by hydrolysis of the compound from Example 10 in a mixture of ethanol, water and concentrated hydrochloric acid. Physical data are given in Table 1.

EXAMPLE 12

4,4"-Bis(dimesitylboryl)-p-terphenyl $R_1$–$R_4$=mesityl; n=1; X=4,4"-p-terphenylene The compound is obtained in a yield of 73% by Method B described above using the appropriate starting materials. Physical data are given in Table 1.

EXAMPLE 13

4,4"-Bis[bis(chloromesityl)boryl]-p-terphenyl $R_1$–$R_4$=chloromesityl, N=1; X=4,4"-p-terphenylene The compound is obtained in a yield of 51% by Method B described above, using 2 equivalents of bis(chloromesityl)fluoroborane. Physical data are given in Table 1.

EXAMPLE 14

4,4"Bis(dimesitylboryl)-o-terphenyl $R_1$–$R_4$=mesityl; n=1; X=4,4"-o-terphenylene The compound is obtained in a yield of 43% by Method B described above, using the appropriate starting materials. Physical data are given in Table 1.

EXAMPLE 15

1,5-Bis(dimesitylboryl)naphthalene $R_1$–$R_4$=mesityl; n=1; X=1,5-naphthylene

The compound is obtained in a yield of 86% by Method C described above in diethyl ether at −78° C., using the appropriate starting materials. Physical Data are given in Table 1.

EXAMPLE 16

1,5-Bis[bis(chloromesityl)boryl]naphthalene $R_1$–$R_4$=chloromesityl; n=1; X=1,5-naphthylene The compound is obtained in a yield of 83% by Method C described above in diethyl ether at −78° C., using the appropriate starting materials. Physical data are given in Table 1.

EXAMPLE 17

1,7-Bis(dimesitylboryl)naphthalene $R_1$–$R_4$=mesityl; n=1; X=1,7-naphthylene

The compound is obtained In a yield of 37% by Method C described above in diethyl ether at −78° C., using the appropriate starting materials. Physical data are given in Table 1.

EXAMPLE 18

9-Dimesitylboryl-10-di(2-methylphenyl)borylanthracene $R_1$,$R_2$=mesityl; $R_3$,$R_4$=o-tolyl; n=1; X=9,10-anthracylene The compound is prepared by Method A described above by way of 9-bromo-10-dimesitylborylanthracene. The bromium-lithium exchange and subsequent treatment with ditolylbromoborane gives the desired product in a yield of 55%. Physical data are given in Table 1.

EXAMPLE 19

9,10-Bis(dimesitylboryl)anthracene $R_1$–$R_4$=mesityl; n=1; X=9,10-anthracylene The compound is obtained in a yield of 45% by Method C described above in diethyl ether at 0° C., using the appropriate starting materials. Physical data are given in Table 1.

EXAMPLE 20

Polymesitylphenylborane

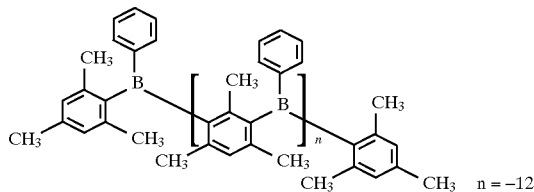

4 equivalents of tert-butyllithium (0.020 mol) in pentane are added over the course of one hour at −78° C. to a solution of 1.86 g (0.005 mol) of diiodomesitylene in THF. The suspension is stirred at −78° C. for 3 hours and then treated with 0.57 g (0.0045 mol) of phenyldifluoroborane. The reaction mixture is warmed to room temperature and stirred for 2 hours. It is poured into 50 ml of water and the mixture is subjected twice to extraction with 50 ml of ethyl acetate. The combined organic phases are dried over magnesium sulphate, filtered and concentrated. The crude product is purified by washing with boiling acetonitrile, giving 0.37 g (38% of theory) of a white solid. GPC (Gel Permeation Chromatography) reveals $M_n$=1730; $M_w$=1061, $M_n/M_w$=1.63. Further physical data are given in Table 1.

EXAMPLE 21

1,1′-Bis(dimesitylboryl)ferrocene

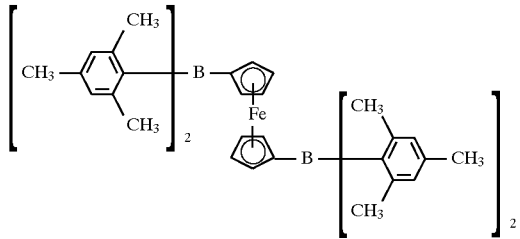

The compound is obtained in a yield of 10% by Method D described above, using the appropriate starting materials.

EXAMPLE 22

1,4-Bis[bis(dinitromesityl)boryl]benzene $R_1$–$R_4$=dinitromesityl; n=1; X=1,4-phenylene 2.87 g (0.005 mol) of 1,4-bis(dimesitylboryl)benzene (=compound from Example 1) are added in portions over the course of 25 minutes at −78° C. to a mixture of 13.9 ml (25.5 g, 0.26 mol) of concentrated sulfuric acid and 24.9 ml (37.8 g, 0.6 mol) of nitric acid. The mixture is warmed to −40° C. over the course of 30 minutes, and then water is added carefully until reaction is no longer exothermic. The precipitated solid is isolated by filtration, washed with water and dried. Recrystallization from ethyl acetate gives 0.55 g (0.0006 mol, i.e. 13% of theory) of a white solid. Physical data are given in Table 1.

EXAMPLE 23

1,7-Bis[bis(chloromesityl)boryl]naphthyl $R_1$–$R_4$=chloromesityl; n=1; X=1,7-naphthylene The compound is prepared in analogy to Method B described above and obtained in a yield of 57%. Physical data are given in Table 1.

EXAMPLE 24

1,4-Bis[bis(dichloromesityl)boryl]benzene $R_1$–$R_4$=dichloromesityl; n=1; X=1,4-phenylene The compound is prepared in analogy to Method B described above using bis(dichloromesityl)fluoroborane and is obtained in a yield of 13%. Physical data are given in Table 1.

EXAMPLE 25

1,6- and 1,8-bis(dimesitylboryl)pyrene (mixture of the 1,6- and 1,8-compounds)

$R_1$–$R_4$=mesityl; n=1; X=1,6- und 1,8-pyrenyl

The mixture of compounds is prepared in analogy to Method C described above in THF at −78° C. and is obtained in a yield of 74%. Physical data are given in Table 1.

EXAMPLE 26

1,6- and 1,8-Bis[bis(chloromesityl)boryl]pyrene (mixture of the 1,6- and 1,8 compounds)

$R_1$–$R_4$=chloromesityl; n=1; X=1,6- und 1,8-pyrenyl

The mixture of compounds is prepared in analogy to Method C described above in THF at −78° C. and is obtained in a yield of 56%. Physical data are given in Table 1.

EXAMPLE 27

Poly(4-butylphenyl)durylborane $R_1$, $R_3$=4-butylphenyl; $R_2$, $R_4$=duryl; n=2-22, X=1,4-durene The compound is prepared in analogy to the method described for compound 20, using diiododurene and potassium p-tert-butylphenyltrifluoroborate, and is obtained in a yield of 33%. Physical data are given in Table 1.

EXAMPLE 28

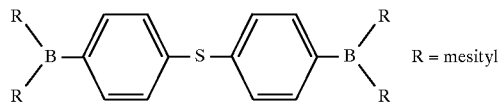

The compound is prepared by Method C described above using 4 equivalents of t-butyllithium in THF at −78° C. and is obtained in a yield of 77%. Physical data are given in Table 1.

EXAMPLE 29

3,5-Bis(dimesitylboryl)-1-trimethylsilylbenzene $R_1$–$R_4$=mesityl; n=1; X=1-trimethylsilyl-phen-3-yl-5-yl a) 1-bromo-3,5-bis(dimesitylboryl)benzene 6.25 ml (0.01 mol) of 1.6M butyllithium in hexane are added over 5 minutes at −78° C. to a suspension of 3.14 g (0.01 mol) of 1,3,5-tribromobenzene in 50 ml of diethyl ether. The reaction mixture is stirred at −78° C. for 2 hours, during which a yellow-orange suspension is produced. 2.68 g (0.01 mol) of solid dimesitylfluoroborane are added, and the reaction mixure is warmed to room temperature over about one hour. The mixture is then diluted with 50 ml of hexane and cooled to 0° C. The solid produced is filtered, washed several times with cold hexane and then washed with water and, finally, with methanol, until the solid is colourless. Drying gives 3.54 g (0.0073 mol; i.e. 73% of theory) of a white solid (1,3-dibromo-5-dimesitylborylbenzene). Following purification by chromatography (hexane; SiO$_2$) a melting point of 190°–191° C. is obtained.

Elemental analysis for $C_{24}H_{25}BBr_2$ gives: C calc.: 59.55%; found: 59.52% H calc.: 5.21%; found: 5,12%

To prepare 1-bromo-3,5-bis(dimesitylboryl)benzene, 1,3-dibromo-5-dimesitylborylbenzene is again reacted by the above-described method with butyllithium and dimesitylfluoroborane. The yield of 1-bromo-3,5-bis (dimesitylboryl)benzene is 76% of theory (for physical data see Example 32).

b) 3,5-bis(dimesitylboryl)-1-trimethylsilylbenzene 6.25 ml (0.01 mol) of a 1.6M solution of butyllithium in hexane are added at −78° C. to a solution of 6.53 g of (0.01 mol) of 1-bromo-3,5-bis(dimesitylboryl)benzene in 50 ml of THF. The mixture is stirred at −78° C. for 1.5 h, and then 2.0 ml (3.0 g; 0.015 mol) of trimethylsilyl iodide are added over the course of 10 minutes. After the mixture has been stirred again at −78° C. for one hour, it is allowed to warm up to room temperature and stirred for about 12 hours. It is then diluted with water and subjected twice to extraction with 50 ml of ethyl acetate each time. Drying over magnesium sulfate and concentration gives 7.15 g of a viscous oil. Following purification by chromatography (hexane, SiO$_2$), 3.7 g ( 0.0058 mol, i.e. 58% of theory) of the title compound are obtained as a white solid. Physical data are given in Table 1.

EXAMPLE 30

3,5-Bis(dimesitylboryl)-1-diisopropylaminocarbonyl-benzene $R_1$–$R_4$=mesityl; n=1; X=1-diisopropylaminocarbonyl-phen-3-yl-5-yl The compound is prepared in analogy to Method b) described in Example 29, using Cl(CO)N(i-C$_3$H$_7$)$_2$ as electrophile. Recrystallization from hexane gives the product in a yield of 46%. Physical data are given in Table 1.

EXAMPLE 31

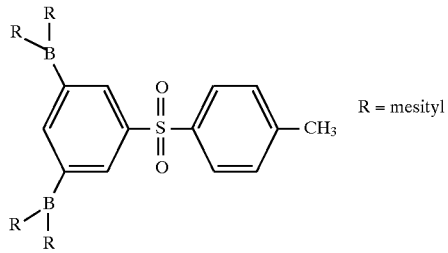

R = mesityl

The compound is prepared in analogy to Method b) described in Example 29, using

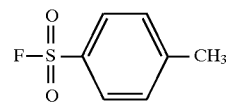

as electrophile. Purification by washing in boiling hexane gives a yield of 62%. Physical data are given in Table 1.

EXAMPLE 32

1-Bromo-3,5-bis(dimesitylboryl)benzene $R_1$–$R_4$=mesityl; n=1; X=1-bromophen-3-yl-5-yl The preparation of this borane is described in Example 29 stage a). Physical data are given in Table 1.

EXAMPLE 33

1-Bromo-3,5-bis[bis(chloromesityl)boryl]benzene $R_1$–$R_4$=chloromesityl; n=1; X=1-bromophen-3-yl-5-yl This compound is prepared similarly to the compound described in Example 32, using bis(chloromesityl)fluoroborane as electrophile. Physical data are given in Table 1.

EXAMPLE 34

1,3,5-Tris[bis(chloromesityl)boryl]benzene $R_1$–$R_4$=chloromesityl; n=1; X=1-bis(chloromesityl)borylphen-3-yl-5-yl The compound is prepared similarly to the compound from Example 29, using (dichloromesityl)fluoroborane as electrophile both in stage a) and in stage b). Physical data are given in Table 1.

EXAMPLE 35

Bis[3-(dimesitylboryl)-2,4,6-(trimethyl)phenyl]-phenylborane

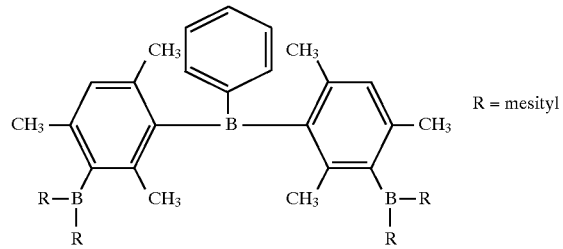

R = mesityl a) (1-Bromo-2,4,6-trimethylphenyl)dimesitylborane 67 ml (0.1 mol) of a 1.5M solution of t-butyllithium in pentane are added dropwise through a syringe over the course of 2.5 h and at −78° C. to a suspension of 13.9 g (0.05 mol) of dibromomesitylene in 100 ml THF. The mixture is stirred at −78° C. for 1.5 hours more and then solid dimesitylfluoroborane is added, and the reaction mixture is allowed to warm to room temperature over the course of 2 hours and then diluted with 200 ml of water. Extraction is subsequently carried out twice with 50 ml of ethyl acetate each time. Drying over magnesium sulfate and concentration give a beige-white solid. Washing with boiling acetonitrile gives 15.62 g (i.e. 70% of theory) of the desired borane. Elemental analysis for $C_{27}H_{32}BBr$ gives: C calc.: 72.51%; C found, 72.78%; H calc.: 7.21%; H found: 7.30%.

b) Title compound

A solution of 8.94 g (0.02 mol) of the compound from stage a) in 50 ml of THF is treated at −78° C. with 12.5 ml (0.02 mol) of a 1.6M solution of butyllithium in hexane. After stirring at −78° C. for 1 hour, the red solution is treated with 1.3 ml (1.39 g; 0.011 mol) of phenyidifluoroborane and allowed to warm to room temperature over the course of one hour. The reaction mixture is diluted with 100 ml of water and subjected to extraction with ethyl acetate. Drying over magnesium sulfate and concentration give a white solid. Chromatography (hexane, $SiO_2$) gives 4.14 g (0.0112 mol, i.e. 56% of theory) of the desired product. Physical data are given in Table 1.

EXAMPLE 36

1,4-Bis[bis(chloromesityl)boryl]naphthalene $R_1$–$R_4$=chloromesityl; n=1; X=1,4-naphthylene The compound is obtained in a yield of 71% by Method B described above using bis(chloromesityl)fluoroborane. Physical data are given in Table 1.

EXAMPLE 37

1,4-Bis(dimesitylboryl)naphthalene $R_1$–$R_4$=mesityl; n=1; X=1,4-naphthylene

The compound is obtained in a yield of 71% by Method B described above. Physical data are given in Table 1.

EXAMPLE 38

1,4,7-Tris(dimesitylboryl)naphthalene $R_1$–$R_4$=mesityl; n=1; X=7-dimesitylborylnaphth-1-yl-4-yl The compound is prepared by method B described above but with three successive additions of butyllithium and dimesitylfluoroborane. It is obtained in a yield of 63%. Physical data are given in Table 1.

EXAMPLE 39

4,4'-Bis[bis(chloromesityl)boryl]biphenyl $R_1$–$R_4$=dichloromesityl; n=1; X=4,4'-biphenylene The compound is obtained in a yield of 22% by Method B described above using bis(chloromesityl)fluoroborane. The physical data are given in Table 1.

EXAMPLE 40

1,3,5-Tris(dimesitylboryl)benzene $R_1$–$R_4$=mesityl; n=1; X=dimesitylborylphen-3-yl-5-yl The compound of Example 40 is prepared similarly to the compound from Example 29 by threefold treatment with dimesitylfluoroborane. The yield is 73%. Physical data are given in Table 1.

TABLE 1

Boranes

| Compd. from Ex. | Melting point [°C.] | $^1$H-NMR in $CDCl_3$ at 300 Hz δ[ppm] J [Hz] |
|---|---|---|
| 1 | 253–255 | 7.43(s, 4); 6.79(8); 2.28(s, 12); 1.98(s, 24) |
| 2 | * | 7.63–7.18(m, 14); 6,83(s, 4); 2.30(s, 6); 2.05(s, 12) |
| 3 | 232–233 | 7.45(d, 2, J=7.8); 7.39(d, 2, j=7.8); 6.89(s, 2); 6.80 (s, 4); 2.37(s, 6); 2.29(s, 6); 2.06(s, 6); 1.97(s, 18) |
| 4 | 248–250 | 7.40(s, 4); 6.90(s, 4); 2.37(s, 12); 2.06 (s, 12); 1.97(s, 12) |
| 5 | 172–173 | 7.54(d, 2, J=7.4); 7.52(s, 1); 7.29(t, 1, J=7.4); 6.78(s, 8); 2.27(s, 12); 1.94(s, 24) |
| 6 | 143–145 | 7.29(s, 1); 7.19(d, 2, J=9.1); 6.75(s, 8); 2.27(s, 12); 1.94(s, 24) |
| 7 | 68–70 | 7.60(d, 1, J=7.4); 7.52(d, 1, J=7.4); 7.33(s, 1); 7.31(t, 1, J=7.4);p 6.83(m, 2); 6.75(s, 4); 2.35(m, 6); 2.26(s, 6); 2.05(s, 3); 2.02(s, 3); 1.96(s, 3); 1.95(s, 12); 1.92(s, 3) |
| 8 | 254–255 | 7.64(d, 4, J=8.1); 7.58(d, 4, J=8.1); 6.83(s, 8); 2.31(s, 12); 2.03(s, 24) |
| 9 | 228–232 | 7.67–7.53(m, 8); 6.93(s, 2); 6.83(s, 4); 2.39(s, 6); 2.31(s, 6); 2.12(s, 6); 2.03(s, 12); 2.03(s, 6) |
| 10 | 234–236 | 7.46(s, 8); 6.80(s, 8), 4.07(s, 4); 2.29(s, 12); 1.96(s, 24) |
| 11 | 208–209 | 7.73(d, 4, J=7.8); 7.53(d, 4, J=7.8); 6.80(s, 8); 2.30(s, 12); 2.00(s, 24) |
| 12 | >250 | 7.74(s, 4); 7.63(d, 4, J=8.2); 7.60(d, 4, J=8.2); 6.84(s, 8); 2.32(s, 12); 2.04(s, 24) |
| 13 | 192–197 | 7.44(s, 4); 7.64(d, 4, J=8.2); 7.56(d, 4, J=8.2); 6.93(s, 4); 2.40(s, 12); 2.13(s, 12); 2.03(s, 12) |
| 14 | 210–220 | 7.40–7.41(m, 4); 7.30(d, 4, J=11.0); 7.08(d, 4, J=11.0); 6.80(s, 8); 2.30(s, 12); 1.97(s, 24) |
| 15 | >250 | 7.95(d, 2, J=8.3); 7.42(d, 2, J=6.5); 7.15(dd, 2, J=8.3 und 6.5), 6,77(br s, 8) 2.29(s, 12); 1.93(br s, 24) |
| 16 | >250 | 7.92(br d, 2, J=8.3); 7.41(br d, 2, J=6.6); 7.18(br dd, 2, J=8.3 and 6.6); 6.89(br s, 2); 6.87(br s, 2); 2.37(s, 12); 2.10(br s, 12; 1.94(br s, 12) |
| 17 | 248–250 | 8.00(s, 1); 7.88(m, 1); 7.75(d, 1, J=8.2); 7.49–7.41(m, 3); 6.74(s, 4); 6.62(br s, 4); 2.31(s, 6); 2.25(s, 6); 1.80(s, 12); 1.76(br s, 12) |
| 18 | 247–250 | 8.06(m, 2); 7.67(m, 2); 7.41–7.25(m, 4); 7.18–7.10(m, 8); 6.86(br s, 2); 6.66(br s, 2); 2.27(s, 6); 2.17(br s, 6); 2.08(s, 6); 1.67(br s, 6) |
| 19 | 259–260 | 7.97(m, 4); 7.02(m, 4); 6.74(br s, 8); 2.19(s, 12); 2.08(br s, 12); 1.63(br s, 12) |
| 20 | 184–185 | 7.51–7.24(m, 5); 6.80(m, 1); 2.00(br s, 6); 1.83(br s, 3) |
| 21 | >250 | 6.75(s, 8); 4.74(br s, 4); 4.42(br s, 4); 2.28(s, 36) |
| 22 | >230 | 7.66(s, 4); 2.33(s, 12); 2.08(s, 24) |
| 23 | 224–227 | 7.94(d, 1, J=8); 7.90(br s, 1); 7,77(d, 1, J=8); 7.55–7.40(m, 3); 6.87(s, 4); 2.40(s, 6); 2.35(s, 6); 2.10–1.40(br m, 24) |
| 24 | * | 7.30(s, 4); 2.50(s, 12); 2.00(s, 24) |
| 25 | >230 | ** |
| 26 | >230 | ** |
| 27 | 145–150 | 7.50–7.40(m, 2); 7.30–7.10(m, 2); 2.67(br t, 2); 2.07(br s, 12); 1.65(br q, 2); 1.36(br q, 2); 0.93(t, 3, J=7) |
| 28 | 210–211 | 7.44(d, 4, J=8); 7.28(d, 4, J=8); 6.81(s, 8); 2.29(s, 12); 2.00(s, 24) |
| 29 | 151–155 | 7.81(s, 2); 7.50(s, 1); 6.80(s, 8); 2.34(s, 12); 2.01(s, 24); 0.19(s, 9) |
| 30 | 210–211 | 7.47(s, 3); 6.72(s, 8); 3.79(br s, 1) 3.39(br s, 1); 2,26(s, 12); 1.93(s, 24); 1.45(br s, 6); 0.98(br s, 6) |
| 31 | 212–213 | 8.03(s, 2); 7.64(d, 2, J=8); 7.53(s, 1); 7.25(d, 2, J=8); 6.71(s, 8); 2.44(s, 3); 2.28(s, 12); 1.82(s, 24) |
| 32 | 207–208 | 7.65(s, 2); 7.38(s, 1); 6.74(s, 8); 2.27(s, 12); 1.93(s, 24) |
| 33 | 167–169 | 7.65(s, 2); 7.16(s, 1); 6.85(2s, 4); 2.35(2s, 12); 2.03(s, 6); 2.02(s, 6); 1.95(s, 6); 1.94(s, 6) |
| 34 | 178–184 | 7.40(s, 3); 6.79(s, 6); 2.33(s, 18); 1.98(s, 18); 1.89(s, 18) |
| 35 | 210–211 | 7.45–7.35(m, 3); 7.28(d, 2, J=7.5); 6.72(s, 8); 6.66(s, 2); 2,57(s, 6); 2,24(s, 6); 2.06–1.87(numerous s, 42) |
| 36 | >230 | 7.79(br m, 2); 7.35(s, 2); 7.24–7.20(m, 2); |

TABLE 1-continued

Boranes

| Compd. from Ex. | Melting point [°C.] | ¹H-NMR in CDCl₃ at 300 Hz δ[ppm] J [Hz] |
|---|---|---|
| 37 | 210–212 | 6.86(br d, 4); 2.36(s, 12); 2.30–1.70(br d, 24) 7.87–7.84(m, 2); 7.37(s, 2); 7.20–7.15(m, 2); 6.75(s, 8); 2.27(s, 12); 1.95(br s, 24) |
| 38 | 158–165 | 7.90(d, 1, J=2); 7.68(d, 1, J=9); 7.40(d, 1, J=7); 7.37(d, 1, J=7); 7.24(dd, 1, J=9); 6.77(2s, 12); 2.28(2s, 18); 1.95(br s, 36) |
| 39 | >250 | 7.64(d, 4, J=8); 7.55(d, 4, J=8); 6.92(s, 4); 2.39(s, 12); 2.12(s, 12); 2.02(s, 12) |
| 40 | 220–225 | 7.50(s, 3); 6.65(s, 12); 2.23(s, 18); 1.89(s, 36) |

*the value was not determined
**not measured since compounds insoluble

II. Preparation of the Borates

EXAMPLE 1b
Preparation of the tetramethylammonium butyl borate of the compound from Example 1

Method F: 1 equivalent of butyllithium (0.015 mol) in hexane is added at 0° C. over the course of 15 minutes to a stirred solution of 8.6 g (0.015 mol) of 1,4-bis (dimesitylboryl)benzene in 80 ml of THF. The reaction mixture is allowed to warm to room temperature and is then concentrated in vacuo. The residue is treated with 80 ml of a mixture of methanol and water in a ratio of 4:1 and is filtered in order to remove unreacted bisborane. An excess of tetramethylammonium chloride is added, whereupon a white solid precipitates. Filtration and drying give 5.0 g (47% of theory) of the title product. Method G: The borate can also be obtained directly from the 1,4-dibromobenzene without isolating the intermediates, by method B. In this case, following the second warming to room temperature, the reaction mixture is diluted with additional THF so as to give a homogeneous solution. The tetramethylammonium borate is then obtained in a yield of 78% of theory accordance with method F.

Further Examples

The compounds of Examples 1a–h, 2a–f, 3a–d, 4a–h, 5a–c, 6a,7a–d, 8a–l, 9a–b, 10a, 12a–d, 13a, 14a–b, 15a–f, 16a–c, 17a–b, 18a–b, 20a,23a, 24a, 28a, 29a, 34a–b, 35a, 36a, 37a, 38a, 39a–d and 40a are given in Table 2, which also lists the respective preparation method and physical data.

TABLE 2

Borates

| Ex. | Borane Compd from Ex. | Type of borate | Counterion | Equivalents of base | Preparation method | Melting range [°C.] | Yield [%] | ¹¹B-NMR 160 Hz δ [ppm] |
|---|---|---|---|---|---|---|---|---|
| 1a | 1 | Methyl | N(CH₃)₄⁺ | 1 CH₃Li | F | # | 78 | −9.61 |
| 1b | 1 | Butyl | N(CH₃)₄⁺ | 1 C₄H₉Li | F, G | 215–219 | 47;78 | −8.35 |
| 1c | 1 | Dibutyl | 2 N(CH₃)₄⁺ | 2 C₄H₉Li | F | 229–231 | 91 | −8.71 |
| 1d | 1 | Butyl | Cyanin* | 1 C₄H₉Li | F | 102–111 | 87 | −8.25 |
| 1e | 1 | Butyl | QTX** | 1 C₄H₉Li | F | 160–170 | 82 | −8.52 |
| 1f | 1 | Phenyl | N(CH₃)₄⁺ | 1 C₆H₄Li | F | >230 | 81 | −5.96 |
| 1g | 1 | Phenyl | Cyanine* | 1 C₆H₄Li | F | 120–123 | 33 | # |
| 1h | 1 | Diphenyl | 2 N(CH₃)₄⁺ | LiC₆H₄Li | F | >230 | 59 | −1.96 |
| 2a | 2 | (CH₃)₃Si—CH₂ | N(CH₃)₄⁺ | 1 (CH₃)₃Si—CH₂ Li | F | 130–170 | 80 | −9.50 |
| 2b | 2 | Butyl | N(CH₃)₄⁺ | 1 C₄H₉Li | F | 128–132 | 77 | −9.45 |
| 2c | 2 | s-Butyl | N(CH₃)₄⁺ | 1 s-C₄H₉Li | F | 136–152 | 29 | −6.57 |
| 2d | 2 | Benzyl | N(CH₃)₄⁺ | 1 BenzylLi | F | >250 | 89 | −8.03 |
| 2e | 2 | 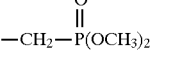 | Li⁺ | 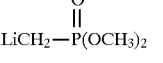 | F | 192–195 | 69 | −10.21 |
| 2f | 2 | 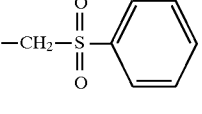 | N(CH₃)₄⁺ | 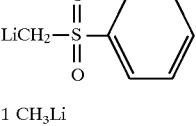 | F | 140–142 | 85 | −9.62 |
| 3a | 3 | Methyl | N(CH₃)₄⁺ | 1 CH₃Li | F | 170–172 | 100 | −8.92 −9.76 |
| 3b | 3 | Butyl | N(CH₃)₄⁺ | 1 C₄H₉Li | F | 172–182 | 86 | −7.38 −8.18 |
| 3c | 3 | Dimethyl | 2 N(CH₃)₄⁺ | 2 CH₃Li | F | 180–184 | 87 | −8.72 −9.77 |
| 3d | 3 | Dibutyl | 2 N(CH₃)₄⁺ | 2 C₄H₉Li | F | 224–225 | 22 | −7.59 −8.61 |
| 4a | 4 | Methyl | N(CH₃)₄⁺ | 1 CH₃Li | F | 180–188 | 82 | −8.60 |
| 4b | 4 | Butyl | N(CH₃)₄⁺ | 1 C₄H₉Li | F | 162–172 | 80 | −7.40 |
| 4c | 4 | Dimethyl | 2 N(CH₃)₄⁺ | 2 CH₃Li | F | 179–180 | 98 | −8.84 |
| 4d | 4 | Dibutyl | 2 N(CH₃)₄⁺ | 2 C₄H₉Li | F | 230–232 | 61 | −7.64 |
| 4e | 4 | Butyl | Cyanine* | 1 C₄H₉Li | F | 110–124 | 89 | −7.64 |
| 4f | 4 | Butyl | QTX** | 1 C₄H₉Li | F | 154–161 | 84 | −7.67 |
| 4g | 4 | Phenyl | N(CH₃)₄⁺ | 1 C₆H₅Li | F | 200–205 | 75 | −5.20 |
| 4h | 4 | Phenyl | Cyanine* | 1 C₆H₅Li | F | 138–140 | 72 | −5.23 |

TABLE 2-continued

Borates

| Ex. | Borane Compd from Ex. | Type of borate | Counterion | Equivalents of base | Preparation method | Melting range [°C.] | Yield [%] | $^{11}$B-NMR 160 Hz δ [ppm] |
|---|---|---|---|---|---|---|---|---|
| 5a | 5 | Methyl | N(CH$_3$)$_4$$^+$ | 1 CH$_3$Li | F | 210–220 | 100 | −9.62 |
| 5b | 5 | Butyl | N(CH$_3$)$_4$$^+$ | 1 C$_4$H$_9$Li | F | 150–160 | 36 | −8.73 |
| 5c | 5 | Dibutyl | 2 N(CH$_3$)$_4$$^+$ | 2 C$_4$H$_9$Li | F | 185–187 | 52 | −8.16 |
| 6a | 6 | Methyl | N(CH$_3$)$_4$$^+$ | 1 CH$_3$Li | F | >230 | 86 | −9.91 |
| 7a | 7 | Methyl | N(CH$_3$)$_4$$^+$ | 1 CH$_3$Li | F | 138–140 | 25 | −8.77 −9.72 |
| 7b | 7 | Butyl | N(CH$_3$)$_4$$^+$ | 1 C$_4$H$_9$Li | F | 138–149 | 82 | # |
| 7c | 7 | Dimethyl | 2 N(CH$_3$)$_4$$^+$ | 2 CH$_3$Li | F | 223–233 | 69 | −8.18 −9.28 |
| 7d | 7 | Dibutyl | 2 N(CH$_3$)$_4$$^+$ | 2 C$_4$H$_9$Li | F | 139–145 | 66 | # |
| 8a | 8 | Methyl | N(CH$_3$)$_4$$^+$ | 1 CH$_3$Li | F | 210–215 | 100 | −9.63 |
| 8b | 8 | Butyl | N(CH$_3$)$_4$$^+$ | 1 C$_4$H$_9$Li | F | 172–184 | 65 | −8.74 |
| 8c | 8 | Butyl | N(C$_4$H$_9$)$_4$$^+$ | 1 C$_4$H$_9$Li | F | 78–80 | 53 | −8.71 |
| 8d | 8 | Dimethyl | 2 N(CH$_3$)$_4$$^+$ | 2 CH$_3$Li | F | >270 | 71 | −9.67 |
| 8e | 8 | Dimethyl | 2 N(C$_4$H$_9$)$^+$ | 2 CH$_3$Li | F | 159–160 | 69 | −9.68 |
| 8f | 8 | Dibutyl | 2 N(CH$_3$)$_4$$^+$ | 2 C$_4$H$_9$Li | F | 265–267 | 63 | −8.46 |
| 8g | 8 | Dibutyl | 2 N(C$_4$H$_9$)$^+$ | 2 C$_4$H$_9$Li | F | 225–227 | 52 | −8.82 |
| 8h | 8 | Butyl | Cyanine* | 1 C$_4$H$_9$Li | F | 105–109 | 60 | −8.30 |
| 8i | 8 | Butyl | QTX** | 1 C$_4$H$_9$Li | F | 153–165 | 75 | −8.30 |
| 8j | 8 | Phenyl | N(CH$_3$)$_4$$^+$ | 1 C$_6$H$_5$Li | F | >250 | 74 | −6.23 |
| 8h | 8 | Butyl | Cyanine* | 1 C$_4$H$_9$Li | F | 105–109 | 60 | −8.30 |
| 8k | 8 | Phenyl | Cyanine* | 1 C$_6$H$_5$Li | F | 147–157 | 63 | −6.23 |
| 8l | 8 | Diphenyl | 2 N(CH$_3$)$_4$$^+$ | LiC$_6$H$_5$Li | F | >230 | 39 | −2.52 |
| 9a | 9 | Methyl | N(CH$_3$)$_4$$^+$ | 1 CH$_3$Li | F | 150–170 | 55 | −9.06 −9.96 |
| 9b | 9 | Dimethyl | 2 N(CH$_3$)$_4$$^+$ | 2 CH$_3$Li | F | # | 81 | −9.08 −10.01 |
| 10a | 10 | Dimethyl | 2 N(CH$_3$)$_4$$^+$ | 2 CH$_3$Li | F | # | # | # |
| 12a | 12 | Methyl | N(C$_4$H$_9$)$_4$$^+$ | 1 CH$_3$Li | F | 165–167 | 58 | −9.99 |
| 12b | 12 | Butyl | N(CH$_3$)$_4$$^+$ | 1 C$_4$H$_9$Li | F | >230 | 58 | −8.41 |
| 12c | 12 | Dibutyl | 2 N(CH$_3$)$_4$$^+$ | 2 C$_4$H$_9$Li | F | 205–210 | 66 | −8.77 |
| 12d | 12 | Butyl | Cyanine* | C$_4$H$_9$Li | F | 103–110 | 41 | −8.35 |
| 13a | 13 | Butyl | N(CH$_3$)$_4$$^+$ | 1 C$_4$H$_9$Li | F | # | 26 | # |
| 14a | 14 | Methyl | N(CH$_3$)$_4$$^+$ | CH$_3$Li | F | 160–180 | 62 | −10.09 |
| 14b | 14 | Butyl | N(CH$_3$)$_4$$^+$ | C$_4$H$_9$Li | F | 160–180 | 63 | −8.84 |
| 15a | 15 | Methyl | N(CH$_3$)$_4$$^+$ | CH$_3$Li | F | 230–235 | 86 | −9.23 |
| 15b | 15 | Butyl | N(CH$_3$)$_4$$^+$ | C$_4$H$_9$Li | F | 152–165 | 62 | −7.35 |
| 15c | 15 | Dimethyl | 2 N(CH$_3$)$_4$$^+$ | 2 CH$_3$Li | F | >230 | 37 | −8.82 |
| 15d | 15 | Dibutyl | 2 N(CH$_3$)$_4$$^+$ | 2 C$_4$H$_9$Li | F | 168–173 | 23 | −7.28 |
| 15e | 15 | Butyl | Cyanine* | 1 C$_4$H$_9$Li | F | 125–157 | 48 | −7.40 |
| 15f | 15 | Butyl | QTX** | 1 C$_4$H$_9$Li | F | 146–156 | 38 | −7.42 |
| 16a | 16 | Butyl | N(CH$_3$)$_4$$^+$ | 1 C$_4$H$_9$Li | F | 149–157 | 80 | −6.03 |
| 16b | 16 | Butyl | Cyanine* | 1 C$_4$H$_9$Li | F | 120–129 | 78 | −6.23 |
| 16c | 16 | Butyl | QTX** | 1 C$_4$H$_9$Li | F | 146–152 | 81 | −6.42 |
| 17a | 17 | Methyl | N(CH$_3$)$_4$$^+$ | 1 CH$_3$Li | F | >230 | 26 | −9.91 |
| 17b | 17 | Butyl | N(CH$_3$)$_4$$^+$ | 1 C$_4$H$_9$Li | F | 230–232 | 47 | −7.35 |
| 18a | 18 | Methyl | N(CH$_3$)$_4$$^+$ | 1 CH$_3$Li | F | 199–200 | 74 | −7.83 |
| 18b | 18 | Butyl | N(CH$_3$)$_4$$^+$ | 1 C$_4$H$_9$Li | F | 115–120 | 81 | −7.18 |
| 20a | 20 | Butyl | N(CH$_3$)$_4$$^+$ | 0.5 C$_4$H$_9$Li per eq. of boron | F | 179–180 | 40 | −8.62 |
| ... | | | | | | | | |
| 23a | 23 | Butyl | N(CH$_3$)$_4$$^+$ | 1 C$_4$H$_9$Li | F | >220 | 57 | # |
| 24a | 24 | Butyl | N(CH$_3$)$_4$$^+$ | 1 C$_4$H$_9$Li | F | 141–142 | 15 | # |
| 28a | 28 | Butyl | N(CH$_3$)$_4$ | 1 C$_4$H$_9$Li | F | >250 | 81 | −8.45 |
| 29a | 29 | Butyl | N(CH$_3$)$_4$$^+$ | 1 C$_4$H$_9$Li | F | 125–130 | 74 | −8.38 |
| 34a | 34 | Methyl | N(CH$_3$)$_4$$^+$ | 1 CH$_3$Li | F | 130–160 | 81 | −9.16 |
| 34b | 34 | Butyl | N(CH$_3$)$_4$$^+$ | 1 C$_4$H$_9$Li | F | 150–157 | 82 | −7.69 |
| 35a | 35 | Butyl | N(CH$_3$)$_4$$^+$ | 1 C$_4$H$_9$Li | F | 170–185 | 62 | −8.55 |
| 36a | 36 | Methyl | N(CH$_3$)$_4$$^+$ | 1 CH$_3$Li | F | 186–190 | 35 | −7.91 |
| 37a | 37 | Butyl | N(CH$_3$)$_4$$^+$ | 1 C$_4$H$_9$Li | F | 152–155 | 31 | # |
| 38a | 38 | Butyl | N(CH$_3$)$_4$$^+$ | 1 C$_4$H$_9$Li | F | 145–150 | 43 | −7.06 |
| 39a | 39 | Methyl | N(CH$_3$)$_4$$^+$ | 1 CH$_3$Li | F | 184–199 | 52 | −8.72 |
| 39b | 39 | Butyl | N(CH$_3$)$_4$$^+$ | 1 C$_4$H$_9$Li | F | 185–195 | 53 | −7.55 |
| 39c | 39 | Phenyl | N(CH$_3$)$_4$$^+$ | 1 C$_6$H$_5$Li | F | 227–230 | 64 | # |
| 39d | 39 | Phenyl | Cyanine* | 1 C$_6$H$_4$Li | F | 153–167 | 52 | −5.45 |
| 40a | 40 | Butyl | N(CH$_3$)$_4$$^+$ | 1 C$_4$H$_9$Li | F | 198–199 | 75 | −8.82 |

TABLE 2-continued

Borates

| Ex. | Borane Compd from Ex. | Type of borate | Counterion | Equivalents of base | Preparation method | Melting range [°C.] | Yield [%] | $^{11}$B-NMR 160 Hz δ [ppm] |
|---|---|---|---|---|---|---|---|---|

*Cyanine is: [structure: bis(3,3-dimethyl-1-butylindoline) connected by –CH=CH–CH= bridge, one N⁺, one N, each with C₄H₉]

**QTX is: [structure: thioxanthone-type with –O–CH₂–CH(OH)–CH₂–N⁺(CH₃)₃, and two CH₃ substituents]

... the precise position of the butyl groups in the polyborate has not been determined.

the values were not determined

Ill. Use Examples

EXAMPLE 41

Reactivity of the polyborates in a resist formulation

A photocurable formulation is prepared by mixing the following components:

- 10.0 g of dipentaerythritol monohydroxypentaacrylate, ®SR 399, Sartomer Co., Berkshire, GB
- 15.0 g of tripropylene glycol diacrylate, Sartomer Co., Berkshire, GB
- 15.0 g of N-vinylpyrrolidone, Fluka
- 10.0 g of trimethylolpropane triacrylate, Degussa
- 50,0 g of urethane acrylate ®ACTYLAN AJ20, Societe Nationale des Poudres et Explosifs
- 0.3 g of levelling assistant ®BYK 300, BYK-Mallinckrodt Portions of this composition are mixed with 0.4 or 1.6%, based on the overall quantity of the formulation, of the novel polyborate photoinitiator. All operations are carried out under red light. The samples to which polyborate has been added are applied to a 300 μm aluminium foil. The thickness of the dry film is 60 μm. To this film there is applied a 76 μm thick polyester film, over which a standardized test negative having 21 steps of different optical density (Stouffer wedge) is placed. The sample is covered with a second UV-transparent film and compressed on a metal plate by means of vacuum. Exposure is carried out in a first test series for 5 seconds, in a second series for 10 seconds and in a third series for 20 seconds, using a 4 kW xenon lamp at a distance of 30 cm. Following exposure, the cover films and the mask are removed and the exposed film is developed in ethanol for 10 seconds at 23° C. in an ultrasound bath. Drying is carried out at 40° C. in a convection oven for 5 minutes. The sensitivity of the initiator system used is characterized by indicating the last wedge step which was reproduced (i.e. polymerized) without tack. The higher the number of steps, the more sensitive the system tested. The results are summarized in Table 3.

TABLE 3

| Compound from Example | Concentration [%] | Number of steps reproduced after exposure times of | | |
|---|---|---|---|---|
| | | 5 s | 10 s | 20 s |
| 1a | 0.4 | 2 | 4 | 7 |
| 1b | 0.4 | 4 | 6 | 9 |
| 1c | 0.4 | 3 | 5 | 8 |
| 3a | 1.6 | 4 | 6 | 9 |
| 3b | 1.6 | 5 | 7 | 10 |
| 4a | 1.6 | 5 | 7 | 10 |
| 4b | 0.4 | 5 | 7 | 9 |
| 4b | 1.6 | 5 | 7 | 10 |
| 6a | 1.6 | 2 | 4 | 7 |
| 8a | 1.6 | 5 | 7 | 10 |
| 8b | 1.6 | 7 | 9 | 12 |
| 8d | 1.6 | 3 | 5 | 8 |
| 8f | 1.6 | 6 | 8 | 11 |
| 8g | 1.6 | 3 | 5 | 8 |
| 9a | 1.6 | 6 | 8 | 11 |
| 9b | 1.6 | 3 | 5 | 8 |
| 12b | 1.6 | 3 | 5 | 8 |
| 12c | 1.6 | 4 | 6 | 9 |
| 14a | 1.6 | 2 | 5 | 8 |
| 14b | 1.6 | 4 | 6 | 9 |
| 15a | 1.6 | 5 | 7 | 9 |
| 15b | 1.6 | 7 | 9 | 12 |
| 16a | 1.6 | 8 | 10 | 13 |
| 17a | 1.6 | 4 | 6 | 9 |
| 17b | 1.6 | 6 | 9 | 12 |
| 18a | 1.6 | 3 | 5 | 7 |

EXAMPLE 42

Reactivity of the polyborates in a resist formulation 1.6%, based on the total quantity of the formulation, of each photoinitiator to be tested was incorporated into a formulation as described in Example 41. Sample preparation, exposure and development were likewise carried out by a method similar to that described in Example 41, but exposure was for 20 seconds in each case. The results are listed in Table 4.

TABLE 4

| Compound from Example | Concentration [%] | Number of steps reproduced after exposure for 20 s |
|---|---|---|
| 8j | 1.6 | 7 |
| 13a | 1.6 | 10 |
| 20a | 1.6 | 8 |
| 28a | 1.6 | 11 |
| 34a | 1.6 | 8 |
| 36a | 1.6 | 15 |
| 38a | 1.6 | 15 |
| 39a | 1.6 | 12 |
| 39b | 1.6 | 12 |
| 39c | 1.6 | 7 |
| 23a | 1.6 | 13 |

EXAMPLE 43

Reactivity of the polyborates in combination with a dye in a resist formulation

A photocurable formulation is prepared by mixing the following components:

10.0 g of dipentaerythritol monohydroxypentaacrylate, ®SR 399, Sartomer Co., Berkshire, GB 15.0 g of tripropylene glycol diacrylate, Sartomer Co., Berkshire, GB 15.0 g of N-vinylpyrrolidone, Fluka 10.0 g of trimethylolpropane triacrylate, Degussa 50.0 g of urethane acrylate ®ACTYLAN AJ20, Société Nationale des Poudres et Explosifs 0.3 g of levelling assistant ®BYK 300, Byk-Mallinckrodt Portions of this composition are mixed with 0.4%, based on the overall quantity of the formulation, of the novel polyborate photoinitiator and 0.3% of the dye of the following structure:

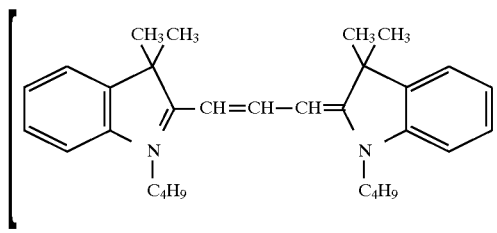

All operations are carried out under red light. The samples to which polyborate has been added are applied to a 300 μm aluminium foil. The thickness of the dry film is 60 μm. To this film there is applied a 76 μm thick polyester film, over which a standardized test negative having 21 steps of different optical density (Stouffer wedge) is placed. The sample is covered with a second UV-transparent film and compressed on a metal plate by means of vacuum. Exposure is carried out in a first test series for 5 seconds, in a second series for 10 seconds and in a third series for 20 seconds, using a 4 kW xenon lamp at a distance of 30 cm. Following exposure, the cover films and the mask are removed and the exposed film is developed in ethanol for 10 seconds at 23° C. in an ultrasound bath. Drying is carried out at 40° C. in a convection oven for 5 minutes. The sensitivity of the initiator system used is characterized by indicating the last wedge step which was reproduced (i.e. polymerized) without tack. The higher the number of steps, the more sensitive the system tested. The results are summarized in Table 5.

TABLE 5

| Compound from Example | Number of steps reproduced after exposure times of | | |
|---|---|---|---|
|  | 5s | 10s | 20s |
| 1a | 11 | 13 | 16 |
| 1b | 11 | 13 | 17 |
| 3a | 10 | 12 | 15 |
| 3b | 11 | 13 | 16 |
| 4a | 9 | 11 | 14 |
| 4b | 10 | 12 | 15 |
| 6a | 7 | 13 | 17 |
| 8b | 13 | 16 | 19 |
| 8f | 12 | 14 | 17 |
| 8g | 13 | 15 | 21 |
| 9a | 11 | 13 | 16 |
| 9b | 10 | 15 | 16 |
| 12b | 9 | 12 | 15 |
| 12c | 16 | 18 | 20 |
| 14a | 9 | 14 | 17 |
| 14b | 4 | 7 | 20 |
| 15a | 14 | 17 | 20 |
| 15b | 14 | 17 | 20 |
| 17a | 11 | 16 | 18 |
| 17b | 14 | 17 | 20 |

EXAMPLE 44

Reactivity of the polyborates in combination with a dye in a resist formulation 0.4%, based on the total quantity of the formulation, of each photoinitiator to be tested and 0.3% of the dye described in Example 43 was incorporated into a formulation as described in Example 43. Sample preparation, exposure and development were likewise carried out by a method similar to that described in Example 43, but exposure was for 20 seconds in each case. The results are listed in Table 6.

TABLE 6

| Compound from Example | Number of steps reproduced after 20 s | Bleaching behaviour |
|---|---|---|
| 2b | 13 | — |
| 2c | 14 | — |
| 2d | 14 | — |
| 13a | 17 | b |
| 20a | 17 | b |
| 28a | 17 | b |
| 29a | 17 | b |
| 34a | 12 | — |
| 34b | 12 | — |
| 35a | 15 | b |
| 36a | 17 | b |
| 38a | 18 | b |
| 39a | 17 | b |
| 39b | 17 | b |
| 40a | 16 | b |
| 23a | 18 | b |

*b = bleaches out (visual examination)
— = bleaching out is not observed; however, this does not mean that it does not occur, but denotes only that it is not noted in the course of visual examination

EXAMPLE 45

Reactivity of dye-polyborate salts in a resist formulation

The novel dye-polyborate salts are incorporated in a concentration of 0.3%, based on the overall quantity of the formulation, into a formulation as described in Example 41. In these compounds the dye functions as a countercation to the polyborate anion. The compounds contain the dye cations $F^+$ or $Q^+$:

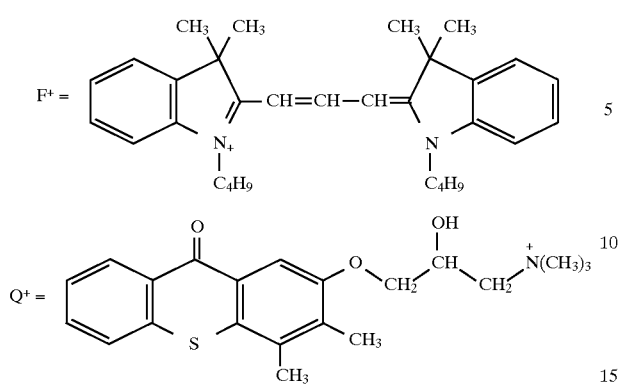

Preparation and curing of the samples are likewise carried out as described in Example 41. The results are listed in Table 7.

TABLE 7

| Compound from Example | Cation | Number of steps reproduced after exposure times of | | | Bleaching behaviour |
|---|---|---|---|---|---|
| | | 5 s | 10 s | 20 s | |
| 1d | F+ | 12 | 15 | 16 | b |
| 4e | F+ | 9 | 12 | 15 | — |
| 8h | F+ | 12 | 14 | 17 | — |
| 12d | F+ | 11 | 14 | 17 | b |
| 15e | F+ | 13 | 15 | 18 | b |
| 16b | F+ | 11 | 13 | 16 | — |
| 1e | Q+ | 8 | 10 | 12 | — |
| 4f | Q+ | 7 | 9 | 12 | — |
| 8i | Q+ | 8 | 10 | 12 | — |
| 15f | Q+ | 8 | 10 | 12 | — |
| 16c | Q+ | 7 | 9 | 11 | — |

*b = bleaches out (visual examination)
*= bleaching out is not observed; however, this does not mean that it does not occur, but denotes only that it is not noted in the course of visual examination

EXAMPLE 46

Reactivity of dye-polyborate salts in a resist formulation

The procedure of Example 45 is repeated but the exposure time is 20 seconds. The results are given in Table 8.

TABLE 8

| Compound from Example | Number of steps reproduced |
|---|---|
| 1g | 11 |
| 4h | 9 |
| 8k | 12 |
| 39d | 8 |

EXAMPLE 47

Reactivity of polyborates in combination with electron acceptors

A formulation is prepared as described in Example 43. Portions of the composition are mixed with 0.4% of the photoinitiator to be tested and with 0.3% of a substance A, B, C, D or E.

A: ® QUANTACURE ITX, International Bio-Synthetics Mixture of

B: ® QUANTACURE QTX, International Bio-Synthetics

C: Benzophenone

D: ® QUANTACURE BTC, International Bio-Synthetics

E: Thioxanthone derivative

The samples are prepared and cured likewise in a manner similar to that described in Example 43. The results are given in Table 9.

TABLE 9

| Compound from Example | Electron acceptor | Number of steps reproduced after exposure times of | | |
|---|---|---|---|---|
| | | 5 s | 10 s | 20 s |
| 4b | A | 5 | 7 | 10 |
| 15a | A | 5 | 7 | 9 |
| 4b | B | 6 | 8 | 10 |
| 15a | B | 4 | 6 | 9 |
| 4b | C | 5 | 7 | 10 |
| 15a | C | 4 | 6 | 8 |
| 4b | D | 5 | 7 | 10 |
| 15a | D | 5 | 7 | 10 |

TABLE 9-continued

| Compound from Example | Electron acceptor | Number of steps reproduced after exposure times of | | |
|---|---|---|---|---|
| | | 5 s | 10 s | 20 s |
| 4b | E | 7 | 9 | 12 |
| 15a | E | 7 | 9 | 11 |

EXAMPLE 48

Polyboranes as electron acceptors in a resist formulation

A formulation is prepared as described in Example 43. Portions of the composition are mixed with 0.4% of tetramethylammonium triphenyl butyl borate and 0.3% of a polyborane of the present application. The samples are prepared and cured likewise in a manner similar to that described in Example 43. The results are given in Table 10.

TABLE 10

| Compound from Example | Number of steps reproduced after exposure times of | | |
|---|---|---|---|
| | 5 s | 10 s | 20 s |
| 1 | 1 | 3 | 7 |
| 8 | 3 | 6 | 9 |

EXAMPLE 49

Polyboranes as electron acceptors in a resist formulation

A formulation is prepared as described in Example 43. Portions of the composition are mixed with 2% of the compound from Example 1 and with 1.5% of an electron donor. The samples are prepared and cured likewise in a manner similar to that described in Example 43. The results are given in Table 11.

TABLE 11

| Electron donor | Number of steps reproduced after exposure for 20 s |
|---|---|
| N-Methyldiethanolamine | 5 |
| Triphenylphosphine | 3 |
| 2,5-Diisopropyldimethylaniline | 2 |

EXAMPLE 50

Combinations of polyborates with monoborates

A photocurable composition is prepared by mixing the following components:

| 37.64 g | of ® Sartomer SR 444, pentaerythritol triacrylate, (Sartomer Company, Westchester) |
| 10.76 g | of ® CYMEL 301, hexamethoxymethylmelamine (American Cyanamid, USA) |
| 47.30 g | of ® CARBOSET 525, thermoplastic polyacrylate containing carboxyl groups (B.F. Goodrich) |
| 4.30 g | of polyvinylpyrrolidone PVP (GAF, USA) |
| 100.00 g | of this composition are mixed with |
| 319.00 g | of methylene chloride and |
| 30.00 g | of methanol. |

Samples of this composition are mixed with in each case 0.68% of a novel polyborate and 0.68% of tetramethylammonium N-butyl triphenyl borate, based on the solids content, by stirring at room temperature for one hour. All operations are carried out under red light. The samples to which initiator has been added are applied to a 300 μm aluminium foil (10×15 cm). The solvent is removed by first drying at room temperature for 5 minutes and then heating at 60° C. for 15 minutes in a convection oven, to give a dry film thickness of 35 μm. A 76 μm thick polyester film is placed on the liquid film, and a standardized test negative with 21 steps of different optical density (Stouffer wedge) is placed over this. The sample is covered with a second UV-transparent film and is compressed on a metal plate by means of vacuum. The sample is then exposed for 40 seconds using a 4 kW xenon lamp at a distance of 30 cm. After exposure, the cover films and the mask are removed and the exposed film is developed for 240 seconds with 1% strength aqueous sodium carbonate solution in an ultrasound bath and then dried at 60° C. in a convection oven for 15 minutes. The sensitivity of the initiator system used is characterized by indicating the last wedge step reproduced without tack. The higher the number of steps, the more sensitive the system. An increase by two steps denotes an approximate doubling of the curing rate. The results are given in Table 12.

TABLE 12

| Compound from Example | Number of steps reproduced |
|---|---|
| 39a | 11 |
| 8b | 8 |

EXAMPLE 51

Combinations of dye-borate salts with polyboranes

A photocurable composition is prepared by mixing the following components:

| 37.64 g | of ® Sartomer SR 444, pentaerythritol triacrylate, (Sartomer Company, Westchester) |
| 10.76 g | of ® CYMEL 301, hexamethoxymethylmelamine (American Cyanamid, USA) |
| 47.30 g | of ® CARBOSET 525, thermoplastic polyacrylate containing carboxyl groups (B.F. Goodrich) |
| 4.30 g | of polyvinylpyrrolidone PVP (GAF, USA) |
| 100.00 g | of this composition are mixed with |
| 319.00 g | of methylene chloride and |
| 30.00 g | of methanol. |

Samples of this composition are mixed with in each case 0.3% of a novel polyborane and 0.3% of the following dye-borate salt, based on the solids content, by stirring at room temperature for one hour.

Dye-borate salt:
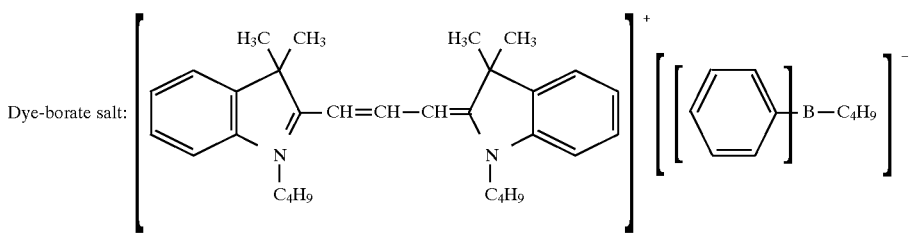

All operations are carried out under red light. The samples to which initiator has been added are applied to a 300 μm aluminium foil (10×15 cm). The solvent is removed by first drying at room temperature for 5 minutes and then heating at 60° C. for 15 minutes in a convection oven, to give a dry film thickness of 35 μm. A 76 μm thick polyester film is placed on the liquid film, and a standardized test negative with 21 steps of different optical density (Stouffer wedge) is placed over this. The sample is covered with a second UV-transparent film and is compressed on a metal plate by means of vacuum. The sample is then exposed for 40 seconds using a 4 kW xenon lamp at a distance of 30 cm. After exposure, the cover films and the mask are removed and the exposed film is developed for 240 seconds with 1% strength aqueous sodium carbonate solution in an ultrasound bath and then dried at 60° C. in a convection oven for 15 minutes. The sensitivity of the initiator system used is characterized by indicating the last wedge step reproduced without tack. The higher the number of steps, the more sensitive the system. An increase by two steps denotes an approximate doubling of the curing rate. The results are given in Table 13.

TABLE 13

| Compound from Example | Number of steps reproduced |
| --- | --- |
| 8 | 17 |

EXAMPLE 52

Dye-polyborate salts in a resist formulation with a Ar⁺laser as light source

The novel dye-polyborate salts are incorporated in a concentration of 0.3%, based on the overall quantity of the formulation, into a formulation as described in Example 41. The dye functions as a counterion to the polyborate anion and corresponds to the dye cation F (see Example 45). Sample preparation and development are as described in Example 41, but exposure is carried out using a Ar⁺laser (UNIPHASE 1583, beam diameter 0.65 mm, divergence 0.95 mrad) with monochromatic light of wavelength 488 nm and an output of 20 mW. The laser beam, with a diameter of about 2.5 mm, is moved at a rate of 24 mm/s over a 21-step Stouffer wedge which is fixed to the sample. After development, a line varying in width and length is left. For evaluation, the number of steps is indicated at which a cured line can still be seen. The results are given in Table 14.

TABLE 14

| Compound from Example | Number of steps reproduced | Bleaching behaviour* |
| --- | --- | --- |
| 15e | 8 | b |
| 8h | 9 | — |

TABLE 14-continued

| Compound from Example | Number of steps reproduced | Bleaching behaviour* |
| --- | --- | --- |
| 1d | 9 | b |
| 12d | 10 | b |

*b = bleaches out (visual examination)
- = bleaching out is not observed; however, this does not mean that it does not occur, but denotes only that it is not noted in the course of visual examination

EXAMPLE 53

Combinations of dyes with polyborates in a resist formulation using a Ar⁺ laser as light source 0.4% of the novel polyborate salt and 0.3% of the dye from Example 43, based on the overall quantity of the formulation, are incorporated into a formulation as described in Example 41. Sample preparation, exposure, development and evaluation are as described in Example 52. The results are given in Table 15.

TABLE 15

| Compound from Example | Number of steps reproduced | Bleaching behaviour* |
| --- | --- | --- |
| 12c | 11 | b |

*b = bleaches out (visual examination)

EXAMPLE 54

Combinations of dyes with polyborates in a resist formulation with a frequency-doubled Nd/YAG laser as light source The novel dye-polyborate salts are incorporated in a concentration of 0.3%, based on the overall quantity of the formulation, into a formulation as described in Example 41. The dye functions as a counterion to the polyborate anion and corresponds to the dye cation F (see Example 45). Sample preparation and development are as described in Example 41, but exposure is carried out using a frequency-doubled Nd/YAG laser (COHERENT DPSS 532-50, beam diameter 0.7 mm, divergence <1.3 mrad) with monochromatic light of wavelength 532 nm and an output of 50 mW. The laser beam, with a diameter of about 3.3 mm, is moved at a rate of 6 mm/s over a 21-step Stouffer wedge which is fixed to the sample. After development, a line varying in width and length is left. For evaluation, the number of steps is indicated at which a cured line can still be seen. The results are given in Table 16.

TABLE 16

| Compound from Example | Number of steps reproduced | Bleaching behaviour* |
|---|---|---|
| 15e | 13 | b |
| 8h | 13 | — |
| 1d | 12 | b |
| 12d | 12 | b |

*b = bleaches out (visual examination)
— = bleaching out is not observed; however, this does not mean that it does not occur, but denotes only that it is not noted in the course of visual examination

EXAMPLE 55

Combinations of dyes with polyborates in a resist formulation using a frequency-doubled Nd/YAG laser as light source The novel polyborate salt from Example 12c in a concentration of 0.4%, and 0.3% of the dye from Example 43, based on the overall quantity of the formulation, are incorporated into a formulation as described In Example 41. Sample preparation, exposure, development and evaluation are as described in Example 53. The results are given in Table 17.

TABLE 17

| Compound from Example | Number of steps reproduced |
|---|---|
| 12c | 12 |

EXAMPLE 56

Polyborates as thermal initiators 0.3% of the novel polyborates was added to the formulation described in Example 41, and about 15 mg thereof were weighed into DSC boats (under red light). The exothermy of the curing reaction was then determined at a heating rate of 10 degrees per minute using a Mettler DSC 30. The initial temperature ($T_A$) and peak temperature ($T_P$) of the exotherms were determined. Those initiators for which the initial or peak temperature lies below the values for the pure formulation are thermal initiators. The results are summarized in Table 18.

TABLE 18

| Compound | $T_A[°C.]$ | $T_P[°C.]$ |
|---|---|---|
| Formulation | 135 | 145 |
| 38a | 110 | 120 |

EXAMPLE 57

Polyborates in combination with electron acceptors as thermal initiators 0.3% of the novel polyborates and 0.4% of the electron acceptor A of example 47 were added to the formulation described in Example 41, and about 10 mg thereof were weighed into DSC boats (under red light). The exothermy of the curing reaction was then determined at a heating rate of 10 degrees per minute using a Mettler DSC 30. The initial temperature ($T_A$) and peak temperature ($T_P$) of the exotherms were determined. Those initiators for which the initial or peak temperature lies below the values for the pure formulation are thermal initiators. The results are summarized in Table 19.

TABLE 19

| Compound | Electron acceptors | $T_A[°C.]$ | $T_P[°C.]$ |
|---|---|---|---|
| Formulation | — | 135 | 145 |
| 38a | A | 113 | 127 |
| 36a | A | 110 | — |

What is claimed is:

1. A compound of the formula I

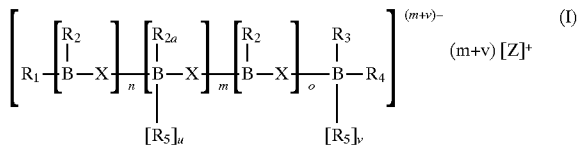

in which n and o are each a number from 0 to 50;
m is a number from 1 to 50;
u and v are 0 or 1, and at least one of the indices u and v is 1;
$R_1$, $R_2$, $R_{2a}$, $R_3$ and $R_4$ independently of one another are phenyl or another aromatic hydrocarbon, which radicals are unsubstituted or are substituted by unsubstituted or halo-, $OR_6$- and/or $NR_8R_9$-substituted $C_1$–$C_6$alkyl, $OR_6$, $S(O)_pR_7$, $OS(O)_2R_7$, $NR_8R_9$, $C(O)OR_6$, $C(O)NR_8R_9$, $C(O)R_{10}$, $SiR_{11}R_{12}R_{13}$, $BR_{14}R_{15}$, $P(O)_qR_{16}R_{17}$ or halogen;
p is 0, 1 or 2;
q is 0 or 1;
$R_5$ is $C_1$–$C_{12}$alkyl, $C_3$–$C_{12}$cycloalkyl, $C_2$–$C_8$alkenyl, phenyl-$C_1$–$C_6$alkyl or naphthyl-$C_1$–$C_3$ the radicals $C_1$–$C_{12}$alkyl, $C_3$–$C_{12}$cycloalkyl, $C_2$–$C_8$alkenyl, phenyl-$C_1$–$C_6$alkyl or naphthyl being unsubstituted or substituted by $OR_6$, $S(O)_pR_7$, $OS(O)_2R_7$, $NR_8R_9$, $C(O)OR_6$, $C(O)NR_8R_9$, $C(O)R_{10}$,

$SiR_{11}R_{12}R_{13}$, $BR_{14}R_{15}$ or halogen, or $R_5$ is phenyl or another aromatic hydrocarbon radical, which radicals are unsubstituted or substituted by $C_1$–$C_6$alkyl, $OR_6$, $S(O)_pR_7$, $OS(O)_2R_7$, $NR_8R_9$, $C(O)OR_6$, $C(O)NR_8R_9$, $C(O)R_{10}$, $SiR_{11}R_{12}R_{13}$, $BR_{14}R_{15}$ or halogen, at least one of the radicals $R_1$, $R_2$, $R_{2a}$, $R_3$, $R_4$ and $R_5$ being a phenyl radical which is substituted ortho to the bond to the boron atom, or being another aromatic hydrocarbon radical which is sterically hindered ortho to the boron atom;
$R_6$ and $R_7$ are unsubstituted or $COOR_{7a}$, OH, $C_1$–$C_{12}$alkoxy- or halo-substituted $C_1$–$C_{12}$alkyl, unsubstituted or mono- to penta-$C_1$–$C_6$alkyl-, —$C_1$–$C_{12}$alkoxy- or -halo-substituted phenyl, or unsubstituted or mono- to penta-$C_1$–$C_6$alkyl-, —$C_1$–$C_{12}$alkoxy- or -halo-substituted phenyl-$C_1$–$C_6$alkyl;
$R_{7a}$ is $C_1$–$C_{12}$alkyl
$R_8$, $R_9$, $R_{10}$, $R_{11}$, $R_{12}$, $R_{13}$, $R_{14}$ and $R_{15}$ independently of one another are as defined for $R_6$ or are $C_3$–$C_{12}$ cycloalkyl, or $R_8$ and $R_9$, together with the N atom to which they are attached, form a 5- or 6-membered ring which may additionally contain O or S atoms, or $R_{14}$ and $R_{15}$, together with the B atom to which they are attached, form a 5- or 6-membered ring;

X is $C_1$–$C_{20}$alkylene which is unsubstituted or substituted by $OR_6$, $S(O)_pR_7$, $OS(O)_2R_7$, $NR_8R_9$, $C(O)OR_6$, $C(O)NR_8R_9$, $C(O)R_{10}$, $SiR_{11}R_{12}R_{13}$, $BR_{14}R_{15}$, halogen or $P(O)_qR_{16}R_{17}$, or X is $C_3$–$C_{12}$cycloalkylene or $C_2$–$C_8$alkenylene, each of which is unsubstituted or substituted by $OR_6$, $S(O)_pR_7$, $OS(O)_2R_7$, $NR_8R_9$, $C(O)OR_6$, $C(O)NR_8R_9$, $C(O)R_{10}$, $SiR_{11}R_{12}R_{13}$, $BR_{14}R_{15}$ or halogen, or where these radicals are interrupted by one or more groups —O—, —S(O)$_p$— or —NR$_{18}$—, or X is a divalent aromatic hydrocarbon radical which is unsubstituted or substituted by $C_1$–$C_6$alkyl, $OR_6$, $S(O)_pR_7$, $OS(O)_2R_7$, $NR_8R_9$, $C(O)OR_6$, $C(O)NR_8R_9$, $C(O)R_{10}$, $SiR_{11}R_{12}R_{13}$, $BR_{14}R_{15}$ or halogen, or X is $C_1$–$C_{20}$alkylene which is interrupted by one or more groups —O—, —S(O)$_p$— or —NR$_{18}$—, or X is a radical of the formula II or III

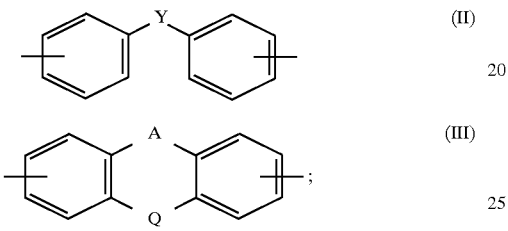

$R_{16}$ and $R_{17}$ independently of one another are as defined for $R_6$ or are $C_3$–$C_{12}$cycloalkyl, $R_{18}$ is as defined for $R_6$ or is hydrogen;

Y is —(CH$_2$)$_r$—, —C(O)—, —NR$_{18}$—, —O—, —S(O)$_p$—, —CR$_{19}$R$_{20}$—,

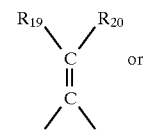

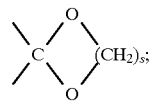

r is 1, 2 or 3;

s is 2 or 3;

$R_{19}$ and $R_{20}$ are $C_1$–$C_6$alkyl or phenyl, or $R_{19}$ and $R_{20}$, together with the C atom to which they are attached, form a 5- or 6-membered ring;

A and Q independently of one another are a direct bond, —(CH$_2$)$_r$—, —CH=CH—, —C(O)—, —NR$_{18}$—, —S(O)$_p$—, —CR$_{19}$R$_{20}$—,

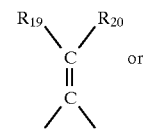

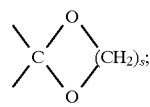

or the radicals $R_1$, $R_2$, $R_3$, $R_4$ and X form bridges to produce radicals of the formula (IV) or (V)

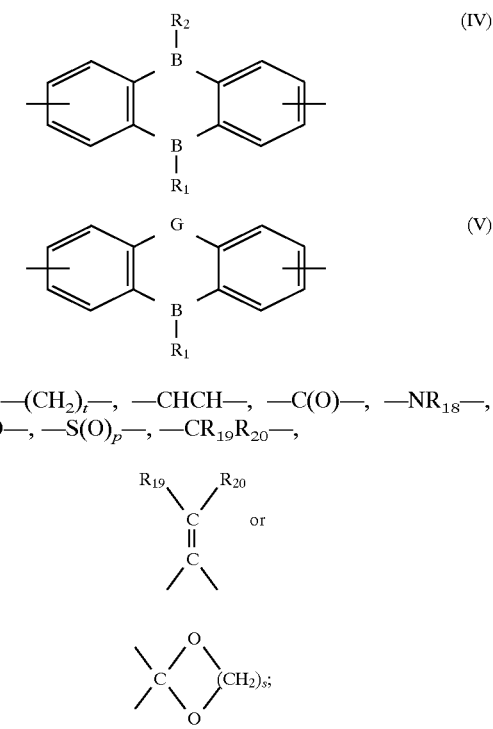

G is —(CH$_2$)$_t$—, —CHCH—, —C(O)—, —NR$_{18}$—, —O—, —S(O)$_p$—, —CR$_{19}$R$_{20}$—, t is 0, 1 or 2;

the radicals of the formulae (II), (III), (IV) and (V) being unsubstituted or being substituted on the aromatic rings by $OR_6$, $S(O)_pR_7$, $OS(O)_2R_7$, $NR_8R_9$, $C(O)OR_6$, $C(O)NR_8R_9$, $C(O)R_{10}$, $SiR_{11}R_{12}R_{13}$, $BR_{14}R_{15}$ or halogen and where additional phenyl rings may be fused to the phenyl rings of the formulae (II), (III), (IV) and (V); provided that $R_1$, $R_{2a}$, $R_3$ and $R_4$ are not simultaneously α-naphthyl, if X is phenylene or 4,4'-biphenylene; and Z is a radical which is able to form positive ions.

2. A compound according to claim 1, in which n and o are zero.

3. A compound according to claim 2, in which m is 1.

4. A compound according to claim 1, in which $R_1$, $R_{2a}$, $R_3$ and $R_4$ are identical.

5. A compound according to claim 1, in which $R_1$, $R_{2a}$, $R_2$, $R_3$, $R_4$, $R_{14}$ and $R_{15}$ independently of one another are 2-, 2,6- or 2,4,6-substituted phenyl or are naphthyl or anthracyl.

6. A compound according to claim 5, in which $R_1$, $R_{2a}$, $R_2$, $R_3$, $R_4$, $R_{14}$ and $R_{15}$ are $C_1$–$C_6$alkyl-, halo-, OR$_6$- or trifluoromethyl-substituted phenyl, 1-naphthyl, 1- or 9-anthracyl.

7. A compound according to claim 1, in which X is $C_1$–$C_{18}$alkylene which is unsubstituted or substituted by $OR_6$, $NR_8R_9$, $SiR_{11}R_{12}R_{13}$, $BR_{14}R_{15}$ or halogen, or in which X is $C_1$–$C_{20}$alkylene which is interrupted by one or more groups —O—, or in which X is phenylene, biphenylene, o-, m- or p-terphenylene, naphthylene, phenanthrylene or ferrocenylene, where the radicals phenylene, biphenylene, o-, m- or p-terphenylene, naphthylene, phenanthrylene or ferrocenylene are unsubstituted or substituted by $C_1$–$C_6$alkyl, $OR_6$, $NR_8R_9$, $C(O)OR_6$, $C(O)NR_8R_9$, $C(O)R_{10}$, $SiR_{11}R_{12}R_{13}$, $BR_{14}R_{15}$ or halogen, or in which X is a radical o formula II in which Y is —(CH$_2$)$_r$—, —C(O)—, —N—, —O—, —S(O)$_p$—, —CR$_{19}$R$_{20}$—,

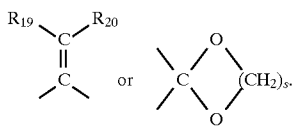

8. A compound according to claim 1, in which n and o are both 0, m is the number 1, $R_1$, $R_{2a}$, $R_2$, $R_3$ and $R_4$ are phenyl substituted by $C_1$–$C_6$alkyl and/or halogen, $R_5$ is $C_1$–$C_{12}$alkyl, $(C_1$–$C_4$alkyl$)_3$Si—$CH_2$— or phenyl, X is unsubstituted phenylene, halo-substituted, biphenylene, o- or p-terphenylene, naphthylene, phenanthrylene, ferrocenylene or a radical of the formula II in which Y is —C(O)— or

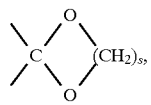

s is 2, and

Z is tetraalkylammonium, a cyanine-dye cation or a thioxanthon cation.

9. A composition comprising (a) at least one ethylenically unsaturated photopolymerizable compound and (b) at least one compound of the formula I as defined in claim 1.

10. A composition according to claim 9 comprising in addition to components (a) and (b) at least one coinitiator or electron acceptor (c).

11. A composition according to claim 10, in which the electron acceptor (c) is a dye.

12. A composition according to claim 10, in which the electron acceptor (c) is an ultraviolet absorber.

13. A composition according to claim 12, in which the ultraviolet absorber is a thioxanthone derivative, coumarine, benzophenone, a benzophenone derivative or a hexaarylbisimidazole derivative.

14. A composition according to claim 9, comprising in addition to components (a) and (b) at least one compound of the formula XI

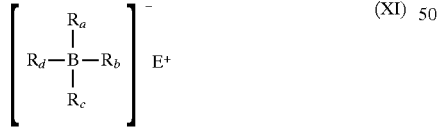

in which $R_a$, $R_b$, $R_c$ and $R_d$ independently of one another are $C_1$–$C_{12}$alkyl, trimethylsilylmethyl, phenyl, another aromatic hydrocarbon, $C_1$–$C_6$alkylphenyl, allyl, phenyl-$C_1$–$C_6$alkyl, $C_2$–$C_8$alkenyl, $C_2$–$C_8$alkynyl, $C_3$–$C_{12}$cycloalkyl or saturated or unsaturated heterocyclic radicals, wherein the radicals phenyl, another aromatic hydrocarbon, phenyl-$C_1$–$C_6$alkyl and saturated or unsaturated heterocyclic radical ar unsubstituted or substituted by unsubstituted or halo-, $OR_6$- and/or $NR_8R_9$-substituted $C_1$–$C_6$alkyl, $OR_6$, $S(O)_pR_7$, $OS(O)_2R_7$, $NR_8R_9$, $C(O)OR_6$, $C(O)NR_8R_9$, $C(O)R_{10}$, $SiR_{11}R_{12}R_{13}$, $BR_{14}R_{15}$, $P(O)_qR_{16}R_{17}$ or halogen;

p is 0, 1 or 2;

q is 0 or 1;

$R_6$ and $R_7$ are unsubstituted or $COOR_{7a}$, OH, $C_1$–$C_{12}$alkoxy- or halo-substituted $C_1$–$C_{12}$alkyl, unsubstituted or mono- to penta-$C_1$–$C_6$alkyl-, —$C_1$–$C_{12}$alkoxy- or -halo-substituted phenyl, or unsubstituted or mono- to penta-$C_1$–$C_6$alkyl-, —$C_1$–$C_{12}$alkoxy- or -halo-substituted phenyl-$C_1$–$C_6$alkyl;

$R_{7a}$ is $C_1$–$C_{12}$alkyl;

$R_8$, $R_9$, $R_{10}$, $R_{11}$, $R_{12}$, $R_{13}$, $R_{14}$ and $R_{15}$ independently of one another are as defined for $R_6$ or are $C_3$–$C_{12}$cycloalkyl, or $R_8$ and $R_9$, together with the N atom to which they are attached, form a 5- or 6-membered ring which may additionally contain O or S atoms, or $R_{14}$ and $R_{15}$, together with the B atom to which they are attached, form a 5- or 6-membered ring;

$R_{16}$ and $R_{17}$ independently of one another are as defined for $R_6$ or are $C_3$–$C_{12}$cycloalkyl; and E is a radical which is able to form positive ions.

15. A composition according to 9, comprising in addition to component (b) a further photoinitiator (d) and/or other additives.

16. A composition according to claim 9, comprising in addition to components (a) and (b) at least one neutral, anionic or cationic dye or a thioxanthone compound and an onium compound.

17. A composition according to claim 16, additionally comprising a free-radical photoinitiator.

18. A composition according to claim 16, additionally comprising an α-amino ketone compound.

19. A composition according to claim 9, comprising at least one borate of the formula I and at least one dye which changes or loses its colour during or after irradiation, which dye may also, as a cation, be part of the compound of the formula I.

20. A composition according to claim 9, containing from 0.05 to 15% by weight, of component (b), based on the composition.

21. A coated substrate which is coated on at least one surface with a composition according to claim 9.

22. A composition comprising (a) at least one ethylenically unsaturated photopolymerizable compound and (b) at least one polyborate anion of the formula Ia

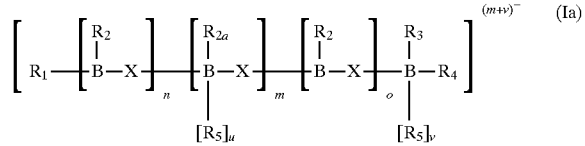

in which the radicals $R_1$, $R_2$, $R_{2a}$, $R_3$, $R_4$, $R_5$ and X, and also n, m, o, u and v, are as defined in claim 1, and (c) a dye cation, sulfonium- or iodonium cation.

23. A composition according to claim 22, additionally comprising at least one further borate compound of the formula XI

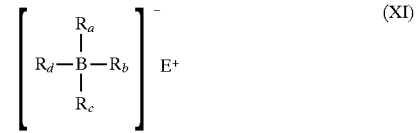

in which $R_a$, $R_b$, $R_c$ and $R_d$ independently of one another are $C_1$–$C_{12}$alkyl, trimethylsilylmethyl, phenyl, another aromatic hydrocarbon, $C_1$–$C_6$alkylphenyl, allyl, phenyl-$C_1$–$C_6$alkyl, $C_2$–$C_8$alkenyl, $C_2$–$C_8$alkynyl, $C_3$–$C_{12}$cycloalkyl or saturated or unsaturated heterocyclic radicals, wherein the radicals phenyl, another aromatic hydrocarbon, phenyl-$C_1$–$C_6$alkyl and saturated or unsaturated heterocyclic radical ar unsubstituted or substituted by unsubstituted or halo-, $OR_6$- and/or $NR_8R_9$-substituted $C_1$–$C_6$alkyl, $OR_6$, $S(O)_pR_7$, $OS(O)_2R_7$, $NR_8R_9$, $C(O)OR_6$, $C(O)NR_8R_9$, $C(O)R_{10}$, $SiR_{11}R_{12}R_{13}$, $BR_{14}R_{15}$, $P(O)_qR_{16}R_{17}$ or halogen;

p is 0, 1 or 2;

q is 0 or 1;

$R_6$ and $R_7$ are unsubstituted or $COOR_{7a}$, OH, $C_1$–$C_{12}$alkoxy- or halo-substituted $C_1$–$C_{12}$alkyl, unsubstituted or mono- to penta-$C_1$–$C_6$alkyl-, —$C_1$–$C_{12}$alkoxy- or -halo-substituted phenyl, or unsubstituted or mono- to penta-$C_1$–$C_6$alkyl-, —$C_1$–$C_{12}$alkoxy- or -halo-substituted phenyl-$C_1$–$C_6$alkyl;

$R_{7a}$ is $C_1$–$C_{12}$alkyl;

$R_8$, $R_9$, $R_{10}$, $R_{11}$, $R_{12}$, $R_{13}$, $R_{14}$ and $R_{15}$ independently of one another are as defined for $R_6$ or are $C_3$–$C_{12}$ cycloalkyl, or $R_8$ and $R_9$, together with the N atom to which they are attached, form a 5- or 6-membered ring which may additionally contain O or S atoms, or $R_{14}$ and $R_{15}$, together with the B atom to which they are attached, form a 5- or 6-membered ring;

$R_{16}$ and $R_{17}$ independently of one another are as defined for $R_6$ or are $C_3$–$C_{12}$cycloalkyl; and E is a radical which is able to form positive ions.

24. A photoinitiator comprising at least one compound of the formula I according to claim 1 and at least one electron acceptor compound.

25. A process for the photopolymerization of nonvolatile monomeric, oligomeric or polymeric compounds containing at least one ethylenically unsaturated double bond, which comprises adding at least one compound of the formula I according to claim 1 to said compounds and irradiating the resulting composition with light having a wavelength ranging from 200 nm up to and including the infrared region.

26. A process according to claim 25 wherein the composition to be irradiated is a pigmented or nonpigmented paint or varnish, a powder coating, a printing ink, a printing plate, an adhesive, a dental composition, a color proofing system, a glass fiber cable coating, a screen printing stencil, a resist material, a composite composition, an encapsulation for electrical and electronic components, a magnetic recording material, an image recording material, a waveguide, an optical switch for photographic reproduction or a three-dimensional object.

27. A process for the thermal polymerization of compounds containing ethylenically unsaturated double bonds, which comprises adding as polymerization initiator at least one compound of the formula 1 according to claim 1 and heating the resulting composition to effect a thermal polymerization.

* * * * *

UNITED STATES PATENT AND TRADEMARK OFFICE
CERTIFICATE OF CORRECTION

PATENT NO. : 5,807,905

DATED : September 15, 1998

INVENTOR(S) : ALLAN FRANCIS CUNNINGHAM ET AL.

It is certified that error appears in the above-identified patent and that said Letters Patent is hereby corrected as shown below:

Title page, left column, section [75], should read:

-- Inventors: Allan Francis Cunningham, Marly, Switzerland; Martin Kunz, Efringen-Kirchen, Germany; Hisatoshi Kura, Hyogo, Japan --

Signed and Sealed this

Sixteenth Day of February, 1999

Attest:

Attesting Officer

*Acting Commissioner of Patents and Trademarks*